US009790517B2

(12) United States Patent
Otte et al.

(10) Patent No.: US 9,790,517 B2
(45) Date of Patent: Oct. 17, 2017

(54) INTERGENIC ELEMENTS FOR ENHANCING GENE EXPRESSION

(75) Inventors: Arie Pieter Otte, Amersfoort (NL); Michel Siep, Rotterdam (NL); John Antonius Verhees, Wageningen (NL); Femke Hoeksema, Duivendrecht (NL); Henricus Johannes Maria Van Blokland, Wijde Wormer (NL)

(73) Assignee: CellaGenics B.V., Amsterdam (NL)

( * ) Notice: Subject to any disclaimer, the term of this patent is extended or adjusted under 35 U.S.C. 154(b) by 474 days.

(21) Appl. No.: 13/704,590

(22) PCT Filed: Jun. 15, 2011

(86) PCT No.: PCT/NL2011/050433

§ 371 (c)(1), (2), (4) Date: Mar. 1, 2013

(87) PCT Pub. No.: WO2011/159157

PCT Pub. Date: Dec. 22, 2011

(65) Prior Publication Data

US 2013/0157312 A1 Jun. 20, 2013

Related U.S. Application Data

(60) Provisional application No. 61/354,822, filed on Jun. 15, 2010.

(51) Int. Cl.
*C12N 15/85* (2006.01)
*C12N 15/67* (2006.01)

(52) U.S. Cl.
CPC ............. *C12N 15/85* (2013.01); *C12N 15/67* (2013.01)

(58) Field of Classification Search
None
See application file for complete search history.

(56) References Cited

U.S. PATENT DOCUMENTS

2007/0212755 A1* 9/2007 Otte et al. .................... 435/69.1

FOREIGN PATENT DOCUMENTS

| | | | |
|---|---|---|---|
| WO | WO-97/25420 | A1 | 7/1997 |
| WO | WO-01/32901 | A1 | 5/2001 |
| WO | WO-03/106684 | A2 | 12/2003 |
| WO | WO-2006/005718 | A2 | 1/2006 |
| WO | WO-2006/048459 | A2 | 5/2006 |
| WO | WO 2007096399 | A2 * | 8/2007 |
| WO | WO-2010/147462 | A2 | 12/2010 |
| WO | WO-2010/147464 | A1 | 12/2010 |

OTHER PUBLICATIONS

Database EMBL [Online] ,2000, Database accession No. AL 139322.*

Wray et al. (2007) The evolutionary significance of cis-regulatory mutations. Nature, 8:206-216.*

AL139322, NCBI GenBank Reference Sequence, GI:14018248, priority to Jan. 13, 2009, 29 pages.*

Vector pBACe3.6 Information/Map, obtained from BacPac Resources webpage accessed at <http://bacpac.chori.org/pbace36.htm> Jan. 23, 2015, 2 pages.*

Rees, et al. "Bicistronic Vector for the Creation of Stable Mammalian Cell Lines that Predisposes All Antibiotic-Resistant Cells to Express Recombinant Protein", Short Technical Reports, BioTechniques (Jan. 1996), vol. 20, pp. 102-110.

"*Homo sapiens* Chromosome 9p21 Cosmid Clone c86, complete sequence," Database EMBL [Online] XP002659826—Nov. 4, 1996.

"Human DNA sequence from clone RP11-145E5 on chromosome 9 Contains the 5' end of the CDKN2B gene for cycline-dependent kinase inhibitor 2B (p15, inhibits CDK4), a ubiquitin A-5s residue ribosomal protein fusion product 1 (UBA52) (RPL40) pseudogene, the 3' end of a variant of the MTAP gene for methylth," Database EMBL [Online] XP002659827—dated May 3, 2000.

"Human DNA Sequence from clone RP11-196P14 on chromosome 13 Contains the ITM2B gene for integral membrane protein 2B (BRI FBD E25B E3-16) and a CpG island," Database EMBL [Online] XP002659825—dated Feb. 15 2000.

"Mus musculus BAC clone RP24-370612 from 14, complete sequence," Database EMBL [Online] XP002659828—Dec. 31, 2004.

Babak, T. et al., "A systematic search for new mammalian noncoding RNAs indicates little conserved intergenic transcription," BMC Genomics, vol. 6, No. 1, Aug. 5, 2005, pp. 104-113.

Hoeksema et al., "The Use of a Stringent Selection System Allows the Identification of DNA Elements that Augment Gene Expression," Molecular Biotechnology, vol. 48, No. 1, Oct. 29, 2010, pp. 19-29.

International Search Report mailed Oct. 7, 2001 in International Application No. PCT/NL2011/050433.

Running Deer et al., "High-Level Expression of Proteins in Mammalian Cells Using Transcription Regulatory Sequences from the Chinese Hamster EF-1α Gene," Biotechnology Progress, vol. 20, No. 3, Mar. 10, 2004, pp. 880-889.

* cited by examiner

*Primary Examiner* — Neil P Hammell

(74) *Attorney, Agent, or Firm* — Gilberto M. Villacorta; Sunit Talapatra; Foley & Lardner LLP

(57) ABSTRACT

The present invention relates to nucleic acid fragments and constructs comprising genomic nucleotide sequences, which are present upstream of Rb1 and p15C that are associated with intergenic transcription, for the production of a gene product of interest in a eukaryotic, preferably mammalian, host cell in the presence of a stringent selectable marker. The invention further relates to host cells comprising the nucleic acid constructs, to methods for generating the host cells and to methods for producing a gene product of interest using the host cells.

15 Claims, 19 Drawing Sheets

A

B

A

B

| DNA element | Cell survival and growth |
|---|---|
| STAR 7 | ++ |
| Rb1E (1-3498) | - |
| Rb1E (1450-3498) | - |
| Rb1E (1-2018) | |
| Rb1F (2425-3424) | - |
| Rb1E (1-2018)/F(2425-3424) | - |
| P15C (1-3352) | - |
| P15C (1-1500) | - |
| P15C (850-3352) | - |

SEQUENCE LISTING

<160> NUMBER OF SEQ ID NOS: 83

<210> SEQ ID NO 1
<211> LENGTH: 6969
<212> TYPE: DNA
<213> ORGANISM: Homo sapiens

<400> SEQUENCE: 1
ctatgtcatt tttgctaaca tgtaatgggc ttactattgt tattttaatt aaattgataa 60
atatatattt aaaatgttct tagtttaaat ttctaatata gtaaatattg atagatacaa 120
cctacataaa caaaagctat atggagtcct caataatttt taagaatgta aagggattct 180
gaggccaaaa tgtttgagaa ttgctgggct aggattgttc aagcctctct ggggcatatg 240
ctaattatct taaagccacc caatcatcac ccaccttccc accaatgtct tcgtactcac 300
ttcttgtgag ccaatcctca cagtcaggag gcagtagtgt taggatggtt gaaagtaaaa 360
gcacaaagag attgagttca aattctttct tggctacctg tgaagtttgt aactttgact 420
aatttactgg gcccttcaaa agtctcagtt ttctcatcta taaaaggggt ataatggtag 480
tacctacctt atacgtttgt gagaattaag aaagaaggca cataatttat gttagctata 540
atagatgaaa ttctttagag ttttatttgt ggttatctaa tcataaggat tggaaagaag 600
taaagtccat gccaacttgt tttacttctt tgaaaaagag aaacaagagg tatagtaacg 660
tttaatgttt ggtttaacat gtacagtgga tgagagggca ttctatattg atctcctcaa 720
tctggccaga aaagtgttgt gatttctaac agtttatttt cacattttgt ttccctaagt 780
tcaatgagcc ctccacttct aatgaggtgg ctttagggta gagaaatcaa aaggcagttg 840
gctttgttgt gacgggcaga tctggatgga gcattataag ggtgaggctg ctgagtttcc 900
catcttgctt atacatatga tgctttgaaa cctacgctga cctgttttaa ctctggccta 960
aagacaggcc aggtgaacag aaatagagcc agcgtctcca ctggcaacac agccatcctg 1020
aagaggaatg tctgtgtgtg catctgccac cagaagtggg atgctagaga ggcattgatc 1080 tctttttga tattgagttt tatccaagta ctcattaagt agatcccttt tattttcaaa 1140
atatctgggg ttaatgtgct taatttggtt agacctagtg agtgagctat ggagaactgg 1200
aatcatttta tatcagttcc tcatctttgc tcagattcat tctgtactgc ctgtctcttc 1260
tgcttcttag acaaagattg aacttgcagg ccaggtgcag tggctcatgc ctgtaattcc 1320
aacactttgg gaggccgagg cgggcagatc acttgaggtc gggaattcga aaccagcctg 1380
accaacatgg agaaaccccg cctctactaa aaatacaaag ttagctgggt gtggtggtgc 1440
atgcctgtaa tcccagctac tcaggaggct gaggcaggag aattgcttca acccaggaga 1500
cggagattgt ggtgagccga ggtgacgcca ttgcactcca gcctgggcaa caagagtgaa 1560
actccatctc aaaataaata aataaaaaga ttgaacttgc tacatgcttc tatctctatc 1620
tgccttctgt gctgccagct cctgcttcta gcaagaagca agagaactta tgttttttca 1680
acccctagtt ctctcctggt aaaactgtga agaatctatt tgcatatcta gccattctac 1740

```
atgcataaaa atgctatatc gacacaaaga aaagacttgt tcataggctc atagttctga   1800
tacaaggctt accagctgaa ttgcccacag tcaggcccta cagagaactc tgctagtttg   1860
atactcctat taatatacag ctaataggtg gtcctgtatc ctacagctgt ggccaaggtc   1920
ccacacacaa tcaattttcc attccgttag actgggaggg agattgttag ctttctatga   1980
acataagaag atcccctgat ggagccatct acataggata ggtttttgta taggtttaat   2040
gacccttcag agttggtaaa tggtccacaa tttctctaac cttcacttcc tggacccaaa   2100
gagagattgg caccaacttt actgtgtcat taatttcagg agtcattcac tgaccttctc   2160
cagcagtggc agcaactccc caagtcaatc aggcaataaa accagctgta ccaaaaatgt   2220
aacaacagtt caagtttact ttatccaggg gcctcaagta ttcaagattg acgtccctac   2280
ctccccatct ccaaggatgc ccccccctcc ccgccatgat gatacccaag agtgagtcag   2340
tgtagccagg taccattgcc cacaggaggc tcagctttgt ccctttcaaa tgatcctccc   2400
caagggcttc tgtttctctt acttctagcc atttggtctt agccattgtg tttcctgtga   2460
tccatatgcc aagcccccac atcttacata ggccattgga aatttgggtg ctctgggaaa   2520
cctcattaat caaaccatgt cctgcaaggc tgactgccaa ccagcccaaa gactgacctg   2580
gtgtcacaga gatgtcctga aggccttctc ctcctggtga agcccatcat caagaagatg   2640
ttggacttgc agatccagac aagagaatat gaggatgttc ttaccacatc aggcagtaat   2700
acaatggcct cctaactggt gtccttgtgc ccgtgctttt cctcttctcc attccccata   2760
cagcagtcag gaaatctgat tgtgttcttc ctttgtttaa aaccctttcc tgtgtcccac   2820
atgatggcct gcatgatcct tcatgccctt gaccttgcca acctctcagg tctcatctca   2880
tgccaccttc ttcctccctg ctgtgctcag gccacatggc cttcctctag ctcctcaagt   2940
gcctagaggc ccttccagag gctggtccct ttgactcttc aactcattaa tttccactca   3000
tccttcagag ctcagctcaa atgtcacttc ctcgaggcga ctgtccttga gtccccactc   3060
gctcatcata cttttgctag ctctgcgtcc cgttccatca taggttgtaa ttacaagtct   3120
gagtaatgtg tgcctccttt agtggcttgt aaggttcatg aaggcaggat ctatatctat   3180
caaagttccc cctgaattct gagtacctac acagtaggag tctgataaat atttattgga   3240
caaataaatc aacaaaaata aatatggaaa agttgctatt gtgggcttca ccagttggtg   3300
agtacagatg tagtcctata acttcataca ctttcaattg ctctatcaca tttgtgatag   3360
ctatgaagtt tttccttcta tgcaacatgc tgctattaga cagctacagg aatgagtgaa   3420
tagcttctcc tctagtttct tgtcctcaat ctctctcttt cctcccctct ggcccaccct   3480
aaatacttat acaggcgagt gtggacacac acacacacac acatcctgtg aagaggaatg   3540
agagcacaaa aagttatata caattcattg taatatgaat caggaaaaag cttcctgact   3600
tcagcctaaa gattccctgg gctgagggga aagggaatgt ccagatggca aatggagtga   3660
ggagagaact tatcctggtg ggtcactgaa aagagtgcta agcctgctcc agtggggaag   3720
aggaagatga cagaaatgtc aggtaagttt gtgggaactg aaaggggagg caatctagaa   3780
gtgttctcag gcaaaggccc aaggagaccc aagatctcag agactaaggt gctatgtggc   3840
agatatgagt ctgggacagc ttacagagtc ccatacgtca cagtgtggcc tggaagcaga   3900
tggatggttc tggggcctga gagtgccgca ggagtccatg ggtcttgggt cacagcctgc   3960
agtttccatg actcagcctg gcagtggaat gacttcctgg gcaccccaaa ggctttatag   4020
aagttgaaag gatagttgtc aaacgtgcag gagcctttta aatgggatca tagggacaag   4080
gtagcaatca tctgcatgtc aggaaacgaa cactaaacag gatgatggat ggcccagtga   4140
```

-continued

```
aggcccaggt gatagcagtc tagaaccagg taccccatct ccccacatgt tgacatgcca   4200
caagcacccc agaaattagt tatttccctg cagttacata ttgactaatt ttaaattgtt   4260
actgcttaca ggatggaggc tctaaataga aaaaaagtta gagagaaaca taaatttgtt   4320
atgtttttat acagctgggt ttgtgggctg caaattgaaa ccattataca attctctttt   4380
aaaatgcaaa tatccctcat acgcatatca tgtggacaaa gtgtttgttt tattaatagc   4440
atcccctaac ctagtttcac tattaaaagg taggtctgag tgggatgtgg gtccctagtg   4500
acctagtgtg agaatagagg gtgttttgtt ttgttttgtt tttgagactg agtctcgctc   4560
tgttgcccag gctggagtgc agtggcatga tctcggctca ctgcaacctc tgcctcctgg   4620
gttcaagtga ttctcatgcc tcagcctctt gagtagctgg gattagatgt gcccaacacc   4680
acgcctgact aatttttgta tttttagtag ggatggggtt tcaccatgtt ggccaggctg   4740
gtctcaaact cctgacctca agtaatccac ccactttggt ctcccaaagt gctgggatta   4800
caggcgtgag ccaccacgtc cggccttaga gggcatttta agggaagaag agaggagttg   4860
ggaaaggatc ttctttctaa tgggaagaga aagaagagac aatagaaaaa ggaagaagga   4920
aaagggccca atgaatgtcc aatattcctt ttgttttcat tgtgattctc atacagaatt   4980
cataaatact tcaacctaaa ccattgaaat tggaatttaa tctgaggtat gaaaaaaatg   5040
ctaggtttaa aatcacaacc caggttgaat ttcttacttt gcccattaat agatgtgtga   5100
ccttgagcat tctcttaact tctctgagcc tcagttactt cagttgtaaa aagggtctaa   5160
taaaacacat cccactgaat tactgagagg attgatccaa ttacatgaaa gagctctgaa   5220
acaataaaaa gttgcaccat ctggggtatc agtttgcggt cgaggagaca atggggagaa   5280
ataatgtaag tgttgagcac atctgcggtc tttaaacaga gagctcaaca caaggacatg   5340
ggcatattgg aaaaaactat ttcagaagag gggaaaaggg agaaaggggg atatgtgggt   5400
attagaggca aacccagata tcctgccttg aggtcaaata attataacat taaatcctgt   5460
ttactgatgc ttagctgtca ggctcttgct catttacctt ggagatccat ttagaattag   5520
tgtaaggtgt aattgacctg tacttagagt tccagaatag gacaatcact tccaaatgcc   5580
ctcagtataa gaaattaaca gtacttgggg ctttagaaat caatgttcaa cctttcaact   5640
actagaaagc ctttttagtt attgtgctta ctatgaaagc ccttggctgt cagttcaaca   5700
agtcgttctt gctttgtgac atctctggaa gtttaatagt tctgtgagaa agtccttgtc   5760
agtgttctga aaactgggaa ttaggaagtc gacttccaat caagcttcag atgacatgcg   5820
acatgcgtta agtttagaaa taacgttagt gtttctaatt tagcatcgtg ttggagtcct   5880
aattatgaaa tgacattaag aaaattccat tcctcagaat tcttgtgcag tagcattggg   5940
tagaaacacc attgtgttct gtgacctggg gtagggatga tatctcaaaa acgcatgctc   6000
aggttgccca tggtgatagc taaactgtct tctcaggaga ggagcaggct ttattaactg   6060
gaactcacca gatttcacag aacattttga agggcttagg attgtgagtt tggaggtaga   6120
tgccaagcag aggtaaacat tttgtataac agaagaaaca tatttgatat gggagagaga   6180
cagaaatctt gtggaaaact ccagagccat caaagctggg acagtgttaa agacgagcac   6240
cctggaagtg aggagccaag tgtgggtttt gaggaacaga tatattaagg gggattctca   6300
caaatgtttt attttgacaa atatcaataa tttagaaaag ttgcaagaat agtatagcaa   6360
ttattcatat accccttcca tatagtacac agaaaaagag ggtatatatt ttaataaata   6420
tttgtgtata cacattttgt gtatagatag gcagataaat agataaagag acaaatgtgc   6480
```

```
acctgtgtat aattttctga actgtttgag aattggttgt aagcatcacg acacttcacc   6540
accaaatact tcagcatgtg tctcctaaga acaaggctgt tctctacatg accacaacat   6600
agttatttca cccagaaact taaacttgat acaatacaat atctaatatt cagtccatat   6660
tcaaatttct cctatcatcc aaataatatc attactaatc tccaatataa agagatttaa   6720
aacatgtttt ccatgttcaa cataaatgtc ttctccattt ttcttacaaa atcatcaaaa   6780
acaactacgt ttcccattta tacttttaca ccagtagttt ctttggagga acttgcactt   6840
gtcccacatc cagattggca ggggataaaa tagaaataat aagagctggc agaagagagg   6900
ctggttgatg ctgattacat tcaaaataac tatttggagg aaaaagcact gattctgttc   6960
ctggggtgt                                                            6969
```

<210> SEQ ID NO 2
<211> LENGTH: 7384
<212> TYPE: DNA
<213> ORGANISM: Mus musculus

<400> SEQUENCE: 2

```
atgtactctg tatgaaaatc tcaatgaaaa ccaaagcctt actggacatt cagttggctc     60
ttgtttgttt gtttggttgg ttggttggtt ggttttttc ctcttaatta tcttttcctt    120
ctaatattaa aaaagtcact tcttaccccc acttttttc cagtaagact ccatattctt    180
cctctaggtc actaagaccc acatctatgt atcactaaga attgtttttc cagagctggg    240
gaaatggctc catggttaag agcactcatt gctcttgtag aggacctggg tttcactccc    300
agcacctatg tggcagctca caatcacaca cacatacaca catacacaca cacacacaca    360
caaaacctaa aatctttttt taaatgcttt ttaacaccaa tagaactagg atagtgagat    420
gactgataaa aggcatactt tgatatgtac tatgggacac acgttaatat gggaaattag    480
cattctgaaa caaaggtttg tgtggtgatt tcaaatttca accctcaaat caccctgtgt    540
aaaaaaaatt gtaactgttt ttctctatat atttttcct gtttacagac ttagtccctt    600
aaccagcaac aagtgaaatt tagttaacat ccatcagaga gatatactgg attcatgtga    660
tatcaatact gggggtgggg cccctggtcc ccaggagtct ggatttacct cagctgttat    720
tcggttacca tcttcttatt cagtacccat ttactgagtt tcaagaatcc attccactag    780
gtcagggaaa ttgtggggtg ctatcgggga ccccatgtga ccctgactta ccacagaacc    840
atcaacgtgt cttcaaacca cactgtggca tgcagaactc tgtaagctgt cacagcctca    900
tgtccatcac acacaatgtt cttcactgag gtgtgtgaag gctcttggtg tggtttgtct    960
gcaactggga ggctagagag aaaaggggaa gctagcttca gggacatgta gcctgtaaac   1020
cctatctcag aattcaaaaa tctggtatct ccttgagttc caacttgaaa acattctaga   1080
ttctagatgg cttctccacc cagttccaca aacagctgct atttctgtta tgtccctttc   1140
cccacgggac atactgagtg tccctctcag cagcttgtac ttttgctcct cacttctgtt   1200
ggccagtcct tcttttgccc tctgaaggca cgaatcttct tactggctcg tattacaaca   1260
agcctgcatg accatgctga gtcctcctca gggtttacga gaaaaagaga taattacaaa   1320
gatgctgctc tcgtgtgagc taaagttaga catcacacaa aggcttctaa agccacagaa   1380
gtttgtgaaa gtaatttttcc attacaaaga tcatttctga gtcatttctc tgatagaaag   1440
gtaatttttc tttcgtagtt aaggttttta ccttaagcag gcaaaataca ggtttatctt   1500
gtttaagggc atcaaatgat gactttctcg taggagctga agtataatta cagaatatac   1560
tggagtgggc ctggagctat acctcagtga tagagcactt gcctaacaga gagaaagccc   1620
```

-continued

```
taggttcact ccacagttct atagaaagta aaaagaacaa tatcaactaa ccagaccccc   1680
ccaaagtccc cagggactaa accaccaacc acagagtaca catggaggga cccatggctc   1740
cagctgcaca tgtagcagag gatggtctta tctggaatca atgagagggg agccccttgg   1800
tcctattgga ggatagatga cccagggtag gggaatgcta gggtgctgag gcagcagtgg   1860
gcagggaggg gggagcaccc tcattgaggg aggggtgggg ctaggggggtt tgtggaggag   1920
aaaatgggaa gggggataaa attgaaataa ccaataaaaa atatgggaaa aatgtaaaaa   1980
tgaataggaa acgatgtaga attgtggaat aacttctcta agagttaacc cgtttctttt   2040
tttggtttgt tttacttctc tttatgaaaa caataaaaat tgacaattgt ttcctttttt   2100
atccccaggt atctgtatag gggaggagac atagccagac ccacaggctt tctccccagg   2160
catccaaggg tctttttaga aaacaaattc taggggctgc gatgactcag tggttaagag   2220
cactcttcca gagaacccgg atttgattcc cagcacccac agaagactca atgcactctc   2280
tggcctctgc aggcaataca cataaatagt gcacagacat acatacaggg aaaatatcca   2340
tacacacaga agtaaataaa tctttaaaaa gaaaagaaac tctagatatt aaagtgaaaa   2400
gttaaatagt aaaatgtgag tgtggttaga aaactgctcc aaggaatggg tagttttcgt   2460
cagtgtgctc tctttctctg tttctgtctc tctgtctctg cccttctccc tgcctacccc   2520
cacagtcctt ctacttgctg agtgaatgct ccatctctga gctctatccc tcagcctgat   2580
acagagtttt aaagacgttg agggttctaa gcatgatggc actgcctgta accctggcac   2640
tcaggagaga aacgagagaa tggctagttg aaggtcagcc tgaatttcat agtgagactt   2700
tgcctctaaa acacataaac aaaaacaaag tgtggaattc aaggagaaag agtaccaagc   2760
cctctttagc catttacata gtatgtacca ggtgtctgtc tgtccatctg tatccatcta   2820
cccatctgtc tgtctcttcc tctctctccc tctctctgca ccccctgaac tccccccccc   2880
ccagtgtgtg tgtgtgtgtg tgtgtgtgtg tgtgtgtgtg tgtgtgtgtg ttgcctatgt   2940
atctattttg ggtgggtcag aaaggaggag agactgaggt gacagaacaa gagaagtcag   3000
ccacccactc cagcagctgt ctaatatctg catgtcacac agaaggggaa aaaaacagct   3060
agtgtcacaa attttgaaag tgtctgatgt tatagaacta catttttact cattggtggg   3120
cacaacctgt gctaataact cttctggatt tattcttggt gatttagtca tctaataaat   3180
atttatcaat tccctatcct ttgggtactt aggatctaga aggagtgtgt gtgtgtgtgt   3240
gtgtgtgtct ctgtctctgt ctctgtctct gtctctgtct gtgttttgcc aggaatcaaa   3300
ggcatgagct agggaatggt tgatcactga gctacattcc cagcccccaa aggaacctac   3360
atccatgaag actataagca aatagggcag gcagacatga taactactcg aattcatcat   3420
tataaacagt gaaggaatat ctattgaact aagagaggca taatctgggc gtgttctact   3480
atggaagctc tgcagataaa atcactttgc cgcctggcag tggtggcgca cgcctttaat   3540
cccagcactc gggaggcaga ggcaggcaga tttctgagtt ctgggacagc ctggcctaca   3600
gagtgagttc caggacagcc agggctacac agagaaaccc tgtctcaaaa aaacaaaaac   3660
aaaaacaaaa aaaaaacccc aaactcaaaa aacaacaaac aaacaaatcc actttgccac   3720
caagcctggt gacctggatc caagctctgg ggggtccaca tagcatgctc tggaacacac   3780
acacacacac acacacacac acacacacac acctaaataa gtgaaaattt tgaaaatatt   3840
caataagaga tggggacctc ctcgggtttg gaatcaaagc catgcaatag agatgaggtg   3900
tcctttgagc catagtatta ggccaaactg actttaggat gaggtgtaga atccttggat   3960
```

-continued

```
atgagatggc aacctcaaac acttgagacc cctggatgaa agaaacttgg attgatgtca   4020
atgtccactc tggaagcttt tatagtctaa gttggggagc aagcaactgc ggctgctagc   4080
caggggtcag tgagtgactc tagaaattag tcacacagaa aagcttttgc ccacctccag   4140
ctgaatccag gaggtgagag ttccagaact atggtgaatg aaagaacaga ctgcttctgg   4200
caggtccctg aacccctgca aaagcctatg caaaggtagt aaaggactcc actggggtat   4260
cctcccatgt tcactagaag ataaagagct tcctctttcc atgagaggat taattgatgg   4320
tatgtgtaac ttgggccaca gctaaatgat ggaatcgggg aatagcaaat aacttgtgtc   4380
cctatgtagg gcttgaatgt tggcagttta agcagtaagc cttgtgttag aagtacagga   4440
cctatataga taagtgtgtt ctttgtgctg acacaggact tcttgtgtgt agtttagatg   4500
tgctagtagg ccctttgtgg tttttaccca ggtgaggctc aggggttgga aggtaacata   4560
tgtttttgac aaaaaaaatg tgatctggta tcacaaaaac cagatgtaaa tagaggtaag   4620
cggcaaaggc agtctgctgt ccaagaagca gaagaaacgg gttcttggaa tgcttctgca   4680
cgaagacaga aatcgacaga attacagttc tcccgggaca ctgaggcaga aggataacta   4740
gtttgatccc agcacaggct tcgaagtgac ttcaaggcca ggttgtggct acacagtgag   4800
tccatttcca aaagaaaaac attctaattt tccataaccc acccattagt ttttatcgaa   4860
ttaaactcct taataccgga cattctgaaa agaaatctat ttagtgggta tttggatcaa   4920
acccaacagt gagaaaagag accactgtct tccaaacttc ccattttcag gcagcaggct   4980
tgcaacatgg ccttccatcc gcatctgtta tcaggcagga gctgcacagg gtaagactgg   5040
gtcccaaagc atctcataca tagtcaagat gggaacctcc aaagccccac taggtgtgtc   5100
caccatgaca cactgcttcc ttttgattct cctaccctaa agctacctca ttccatgtgg   5160
gggaactatt caacttaggg aagcaaggtt tattatgaac gatgagaagc caacacactt   5220
tgctgataag actcaagtga tcaagacaaa attccctctc ccttactgta ctttaaacca   5280
aatgttagct catctgtagg gtgtcatttt ctcaaggaag ttgaacaagc tagttttcac   5340
ttttccaaac tttataatta ggtcatatcg gttatccaac aaagacatct agaatagaaa   5400
aaaaatctaa tcttgtaagt ttgtgcttgc ttcctagata acaaatgagt tcaagtgcat   5460
tcaggatagc atgactatag actgctttca gtatcacata tctgttattt agaataagtc   5520
ctaacaaaga taccacatgc ttttccgact tttaatgtga agaaaactgg ctgtgttttc   5580
ctaaaacttc aagtctaaat gacaatcata agaattatac gtattatagg tattttgtct   5640
gcatatatgt gtctgtgtac catgtgagtg agtacctggt gccctacaaa tcagaagagg   5700
gtgtcgggtc ccttggaatt ggagttacac atgcttgtgc gatgccatgt ggattctggg   5760
aatcaaacct gacacatctc aaagagtagt cagtgatctc agtggctgag gcctctctcc   5820
agctcatatg gtaagttttc ttctgttgtt gttgttttgt ttttttttc agtcactgta   5880
tagccctggc tagctcaaga tcagtggttc ccaaccttcc taatgctgca aacttctaat   5940
acagttagtt cttcatgttg tggtgatccc aaccataatt taaaaagttc ttaaattctc   6000
aaagagtaaa tgaaaatatt ttatatttta cacacacaca cacacacaca cacacacaca   6060
cacacacaca cacatatata tatatatata tatatatata tatatatata tggagacaca   6120
cacatggcac gggttgggga gactgaatca gaaacttcaa gcatactaca tagtttttgt   6180
caacatgaca cagccagggt cactggtaag agaacttaga gatgcctcca tcagattgga   6240
tgggaggcaa atctggagga atttccttga tggataatta atattggagg tggtatactg   6300
ggatggtgcc atcctgggca ggtggtcctg ggagatataa gaaagcagac tgaattagtc   6360
```

```
atggggagca agccagtaag cagcatcctt ctatggcctc tgcttcagtt ccagtcccca   6420

ggttcatgcc tagatttcct gccctggcct ccctcaataa actataattt gagatacata   6480

aaccaaagtc agctctctcc tccccaagtt gcttttagtc atcatggtta tcacagcaat   6540

agaaatccaa ctaagatacc aagatagtct gtgttttaac aaaacaaacc ttccaagtag   6600

ttctcacttg ctggcctaaa taaatcctaa atcatacagc attcgtggat tacaagacta   6660

aatagcctaa cgatattaat tgtctcaaat gtctatcgat agatgaatga ataagcaaga   6720

tatggtaatt catacaatcg aatattatcc acataggtac actctgatta gactgttaag   6780

tgcaatgagg caggcataaa aagacaaata atgtgtgact gccctcaaat gaggtgtgag   6840

aattcataca gagaggagaa agtgatggtg tgtgaagtgg ttcagcagct taagatacct   6900

gctgccaagc ctgatgatcg agttccgtcc ctcgtaccca cagagtaaaa gaagagagct   6960

gactcccact agtggtcctc tgtggcatgt gcacctccct gtctacacac aaataaacat   7020

gtacacacat gcctgcacac gataagcaaa catatacacc tatatgcctt tacacaataa   7080

ctttacttat tattaatttt attttattgt taattgaaaa aggaaaggaa gtagttgcca   7140

gtgtctgggg aaaacaggga atagaaatag gttattaaat agactcaggc tctctgtttt   7200

gcaggagaaa aggtttctaa agactggttg cacaatatga gtgtacttca tagcaccaaa   7260

atgctgaaat tgtcagcttt aagttttgtg tattatacaa ttaaatttca tttaaagagt   7320

atcagtaaat tttactgtat ggatcatatt ggatactgac tcaaatatac agaggtctag   7380

aacc                                                                7384
```

<210> SEQ ID NO 3
<211> LENGTH: 7096
<212> TYPE: DNA
<213> ORGANISM: Bos taurus

<400> SEQUENCE: 3

```
gtgggatatt agaaaggttt tgatctcttg tctagatttt gagttttgtc taaataccca     60

ctaaatggat gtgttctatt ttttaaattt ttactcattt attacttatt tggctgggtc    120

aggtcttagt tgcatcatgc gggatttttt gctgcaggat cttctggact ccttaggtgt    180

ggagtgtagg ctccagagct caggttcaac agttaggctt agttactgca cggcatgtag    240

gatcttattt ctccaagcag ggatgaaact gtgtcctcta cattgcaagg gggagtctta    300

atcactggac caccagggag gccctgatgt gttttatttt tcaaaatgcc tactgttaaa    360

gcgcttaatt cagttgaact tggaatgact atggaaaatt ggaatagctc tgtgttgatt    420

attgaccttt gcccagagca ttctgcagta cttatctcct ctgcttcttg gacaatagac    480

tgaacttgct acttgcctct gtctgtgata gttgccttcc atgctgccag ctcctgcttc    540

ttcctaggct tacgctgcca actcctaggt ttcttcccac taaaataatg gagaaactaa    600

tcacatatct agccaccgta caggctggaa aaattccatg ttggcacaaa gaagagactt    660

gtccgcaggc cccacagttc tgatgcaaga cttcttggct gttctgccat cagccaaacc    720

ttatgtagag tcttgagcag tttgccactc ccagattcct ttatttagct gacaggtggc    780

cctgcatcct acagctgcgg tcaaagtctc acaatcagcc ttttgttgga gtgaaatgaa    840

gactgttggt ttcctatgaa ataactagag ttcccgatag agccctttac atagggtttt    900

caggagttta gtgatccacc agagctggta aacattccat gcttctattc accacagttc    960

tataactttc atctcccgga cacaaaaaga gattaccaca gactttacta tgtgagtagt   1020
```

```
ttcaagatta attcatgata gctgatccac gttgttgtac agcagaaact aaaacaacac   1080
tgtaaaacaa ttcttctcca attaaaataa tactaaaaaa gaaaggcaaa ggagtgattc   1140
atgaatctca cccacagcag tggcagcaac ttccctaatt gaacccggca ataaaaccag   1200
ctgcagtgaa agcctgacat cagttcaagt ttcctttatc cagatctcaa gtactcaagc   1260
ctgacatccc taccccctccg tctctgagga ttctttcccc taaatctgac acccaagagt   1320
gagtgaatgc agccctcatc cacaggaggc tcagtctgtc tctatcaaat ggccctagct   1380
ccaaaggcag agctccctgt ctctcttacc tcgacccatt ctgtctttgg cactgtgctt   1440
cctgcaatcc atttgcagaa ctcttgcccc acacagatca tcagaggtct gggtgcacta   1500
ggggcacttc actgtcttga aagacttgtg gacaaggact gacctgggga tggaaggatc   1560
ttctgaaagg cttctcctct ttcattcagg ccttgagctt ggaggcccag acaaaagaac   1620
agtaggatgc tcttatcaca tcaggcacta atgcaatgac ttcctaaatg acctcctcct   1680
gtctgttatt ttcctctttt caagtctcca cccagcagtc aggaaatttg actgtgtcct   1740
tcctttattt aaaatccctt cctgtctccc acactgtggc ctgcaaaggc cctgtacacc   1800
cgtgccaacc tctccaattc tatcccacgc caccttcctc ctgtgctgtg ctccaatttt   1860
cttttagttc ttcatatgcc atgctccctt ctgccttgag ggctttccac atgccattct   1920
ctttgattct ttaatttatt gattcccact catctttcag agctcagttc aaatgtgact   1980
ttctcaggga agctgccctt cagtccccca atgaattccc tcattttacc ttttacccta   2040
catcccattc cttcctagtc tgtaattata aatctgagta atttttaatg tcttcctccc   2100
aatcagctgg taagattcat gaaggcagaa tctcggccta taaaggctcc ccctctgagt   2160
atccacatgg taggggcttg gtaaatattt actggatgaa taaattaaca aaaaaaatgt   2220
gggaaagtta ctcttgaagg cctcaccagc tggtgaatac acagttctat cacatttgtg   2280
atgaatcttt tcttgcatat gacatgcaga tagtagacag ctgcaggagt gggtgcctgg   2340
cttctcctct agttctttct cttaagtctc tctcttttcc cctctggccc actcaaaata   2400
ccaaagcaag cgtggacaca cacacacaca catgtattca tacacacagc ttacagatgg   2460
caaaggtagg tttagaactt tggcttcttg aaatatacaa aaatactttt ccctccttat   2520
ttctttattt agtgagatct gttaactagc cccttctgtt aaaaaatgtc aatcaaaaaa   2580
taacgtagcc cttctttaag agttgtaaat ttctcaaaag tctaattcct agagattcta   2640
ataaaaactc agacaacttg gaacaatctt ctaaaggcat gtttttcact catacccttc   2700
tcttgctatt taactttcac ttatggattt tgctttatta aaagatcata ggctgcttga   2760
ggagagagtt tataggtttt cttctttata ttcttcccat acctgtgcat aaagagggac   2820
ttaacaaatt ttttctcaat tgctttcaga aagagaagtt aaattgaaaa gggaaagaaa   2880
atgaactaat ccttaggaga agttattaca aaattgtaca ttctaaaatt atatttcttg   2940
acatgacaaa ggaaaatgaa ggctgtaaca agaaggtaaa cctgtactct agctagtaga   3000
aataaaagcc atgctaactg tgactaaata gagtaataaa gtaaataaaa gttactattc   3060
agaatggaaa gatgacagat tcaggaagca ccttttttaat ggaaaattta ttttcgaaag   3120
cttctctgga ttaaaaagtc cgtgagggag tacttcctgg tagttaggac tctgcgcatc   3180
cactgcaagg agtacaagtc cacccctggg ccgtgaagta agatcccagg tgctgctcag   3240
ggcagctaaa ataaaataat acaattttta aaaaaattaa cattaatttt aaaaaagtcc   3300
ctatgactta accttctatt atggccaatt ttaactcatt cttaaaagaa ccttgtttgg   3360
ctgcattggg tcttagttgt ggctcatggg ctgtgctctg ccacacgtgg gacctccttc   3420
```

-continued

```
cacatgtaga atctttcagt ggtgaatgtg ggatctggtt ccctgcccag gttttgaacc   3480
caggcctctc acactgggag tgcagcgtct tagccgctga accaccaggg aagtcccaac   3540
tcatttcccc agttaatact tttgtacttg tctcatggaa tcttcataaa ccctgagagg   3600
actcagggca taagcaatta agtagaagaa gataatgaat cagagaaaag cttcagttaa   3660
tgaatcagag aaaattaaag atcgtttggg ttgagaggaa agggaaagtc cagatggcaa   3720
atagaacaag agaagaactt gctctatggg tcactgaaga cagactgatc ctgttcccag   3780
tggggaggag cagaatgaca gaaacatcgg gtaagtttat gggatccaag aggagaggca   3840
atctacatgt gttcttagaa agaggcccaa ggagacccaa gatttcagag gctgaagggc   3900
tgtgtgacaa gtctaaagtg tgggacagct tatagagtcc catctgatgc agtgtggtag   3960
atggctggtt ctgtggcctg agagtgccac aggagtggat ggggtttcag ggagcacccc   4020
agtttccgtg actcagcctg gcactgaaat gagttttttt gcaccctaga gtctgtatag   4080
aagttaaaag aataattgtc aaacctgcag ggccttttt aatgggctca tggggatgat    4140
gcagtgatcg ccttatatgt ccagtaaaca aagatgaaac cagatgatgg atggctaaat   4200
ggaagccaag ccaaagatgt cacaacaccc aatgctttga cactccacat gcaccccaga   4260
aattagatat atgtcttgga tgtatgttga ctaaatttaa atttttgcca cttagagggt   4320
ggggactcta agtagaaaat agttcagagg aaaataaagt tattatttct aacacagctg   4380
ggtttgggag ctaaaagtga aaccattact tttattaata gtatccccta acctagtttt   4440
gcagttgaga agcagatctg agtgagatgt gggtctctac tgaactagca ggagaataaa   4500
agatgtttgg gggaagaaaa aaggaaatag gaaagaaggg ttgagaaatc ctctttctaa   4560
ctggaagaga gagtcaagag gaaaaagaaa gaaaatagat gaaaatccaa catctctttt   4620
gttttcatta tgatattcat actgactcca tgggatttcc tgtttttcta gcatattcag   4680
gaaggacact ttatagacca ctgaaactgg aattttatct gaggtgagaa aacaagaatg   4740
ttagacatga aatcacaatc caggttgaat ttctggcttt gccataaata gatgtgtgac   4800
cctggacaat ctcttaacct cttcaaattc agtttcaaat caactgtaag tgttagtcac   4860
tcagtcttgt ctgactcttt gcaaccccat gcactgtagc ccattaggct cctctgtcca   4920
tggcattctc caggcaagaa tactatagtg ggttgccatt tccttcccca gaggatcttc   4980
ccaacccagg gatcaaaccc aggtcaccta tatcgcaggc agttttttga gccatcaggg   5040
gagccctcaa atcaactgta aaaagggttt aataaaacac atagcattga attattgaga   5100
gaagtgaatc actatacatg aaagagcttt gtggggcttc cctagtggtc cagtggctag   5160
gactctgcac taccaaagca gggggcccag gttcgatccc tccaagggga actagatccc   5220
acatgctgca accaagagtt cagatgatgc aactgaagat cctgcctgaa gcagctaaga   5280
cctgggaaag caaataaaca aacaaacaca aataaaacat ttttaaaaga gctttgtaag   5340
tggtaaaaac tggaccccat ggggtatgat tttgcagggg aggtgacaat ggggaaagaa   5400
gtgtacaggt gtagacgaca catgggggtg aacactgcta ttttggagtc tctgaacaga   5460
tagttcaaca tgaagaaatc aggtttactg gaaaaacatg gtccagaaga ggagaaaaaa   5520
ggagaggagt tatatgggca tcagaggcaa acccaggtat cctgacttga agttcagtaa   5580
ttacatcaaa ctctttactt aggagtacct gtcagagtct cttgcccatt catttttagag  5640
atctactgac agttaatata tggtacattg tcctatctta tagttttgaa ataggacaat   5700
cacttctcaa gctttcagtg taagaaattt aataggaatt ggggctttag aaaccaagag   5760
```

```
ttaatctttt caaccactgg aaatccttct tagttacagt ctttagcatg aaagcccctg   5820

ctattagctc aactagttgt tcttcctttg agacatctct ggaagctcag cacttatatg   5880

tgaaaacttt tgttcttact ctgaaagctg aacatgaggt tggatgacat gccgtaagtt   5940

tagaaacaga tgcggtcttc ctaatttggt gcagtgttgg aatcctctag ttgcgacatg   6000

agatgaaaat tccattcccc agatttcttt caaagtagca tttggtggga ctgtttcatt   6060

gtgctaccta gggtagggag gacagctcaa aaacacatgc tcagttgcat atgatggttg   6120

ctagactgtc ttttagggaa ggtaggcctt atcaactaga gacccctagg tttcactgga   6180

aattgtgatg ggtttaggat tgtgaatttg agaatagaag ccaagcagag gtaagaaaga   6240

ggaaacatat ttgaagtggg agggagaaag aaatcttgga taaaacacta gagccatcaa   6300

aaggataggg caggactggg gaaagagtat gcgagagaga tccattgaag tggggagcca   6360

agtgtggatt ttggagaaca gatatattaa aggaaattcc caccaatgtt ttattttgaa   6420

aaagaccaaa cttttagaaa agttacaaaa atagtacaat gtagtatatc cactgcattt   6480

acatgtatag agacaaagag tacattttat aaatgtatgt attcacaaat tttgtatata   6540

gttagataaa aagtagatac agagtgaaat atatatatat atatatatat gtatatactt   6600

ttctgaaaca tttgaaagtt gtaggtagac agcatgaaac ttcaccacga aatacttctg   6660

tatgtgtctc ctaagaatga aaccattctc ctatatgacc acagtataat ttttccactc   6720

gggaatttaa acttgataca ataaaatatc taatattcag tacacacaaa cactttcccc   6780

attatcccaa aaacatcctt ctaaatctcc aatataaagg ggatttaaaa actgtttgct   6840

gtgttcaaca taagtgcctt ctccattttc cctatgaaat caccaaaaac aaccacattt   6900

cttgttaata attttatgcc agtaatttat ttgggggaac atgcagatgt tgcatatcca   6960

gattggcagg ggataaaaac agaaatcaca gcgggtgcta gagaagaggc tggttgacgc   7020

tgactacaac cgaagcaaca atttggagga aaggaaatgt aacagactca aaaccactgt   7080

tctattcctg gggtgc                                                   7096
```

```
<210> SEQ ID NO 4
<211> LENGTH: 8819
<212> TYPE: DNA
<213> ORGANISM: Cavia porcellus

<400> SEQUENCE: 4

taaagggtaa tcataagcag tgattttttt ttgttaacat gtattgggct tattttattt     60

caaataaatt aataagtata tattgaaaaa tttcctaatt tcttttttta ttattttttt    120

aattttaatt ttaattttaa agggggtaaa attaaacaca acaaaacaga acaaaatagg    180

acataagaaa gcaatgtaag agatataaat ttcaaagcta gacgacctga gatcttcaca    240

atctatcata ttatctcttg ttttgttcca acaactagtc catgtctttg catacagaga    300

attcatccaa acaacatagt ataaaactga tccgaacaga atgaggaagg agttttaggt    360

cttcaaaacc agacaatagt gaagtcacta atggctatca tagggtctct tgttctcttc    420

aaaatagctt tcattcatat tgaagttcaa caaaacaaaa caggcggggc tgaggggttg    480

cttggtttcc cagtgctcca catcccagcc tgactcaggt cccagtaaac accgggggct    540

cctgtcctgg ccactgtagc ctgccatgct cacagccttt caccacgcgg tggggactgc    600

ttggtttccg catgctccag gtcccaccat ggcacgggtc ccagtaaact ctgctggctc    660

cagccaggaa gctgccggcc ttgattcagg gccagtaatt ttaatttgta agagtaaatg    720

ctgatagaga tgggtaagca aaagctgtat ggagtcctcc gtaatgttca aggatgtgaa    780
```

-continued

```
aagcttatgg tgaagtcttt gagaagtgcc tggctgggat tcaagtcctc gtagggcata    840
tacggattac ctccaagtca tccagtcgtg actcacttcc tccaaaacct gcactcactt    900
cttgttttaa ccaatcttca ttactgggaa acggtcttgt tagaacggtt aagaattagg    960
cacacaagct gggtgtggtg gctcacgcct gcaaccccag cacttaggag gctgcggaag   1020
gaggattgtt gcaagtttga gaccaaccct gagctcaagc tcagcctaac tgcatagcaa   1080
gaccctgtct caaaaaaaaa aaaaaaaaaa aattatgcac aaagagttga agttcaaatt   1140
ctgtcttagc cacttactaa ttttataact gagcaattat tctgcccctc aaaagtcaga   1200
tttctcattt ataaaatagg tgtatagtaa tgattaattt acaaatttgt gggaattaaa   1260
ggagaagtca tatgttaaat ttatcatagg agatgattgt gatcatctaa tataaagatt   1320
gaaaagaaaa aatacagtga atgccacatg tctaacttct tggaaaaaga aatgagagat   1380
cctaagatta gtcaacatct agtttaaaag gtaaaatgag taagaaacag ttttgtacag   1440
gtcagctcat cttgccagga atgttttgat ttctcacagt ttaatgtcag atctggtttc   1500
cctgtgctca ctgagccctc tacggctact gaggtggctg tgaggtcagg agtccaaagg   1560
aagttggttt tctggtgatg gacacagctg gaggagtgct ggagaagcag gacccccgaa   1620
taacagacaa cagacggggc caaggaaggt ggggcccagc ccccgcattg gcagccacag   1680
ccatcccgaa gaggaacatc cgtgctgtga gcgtctgcca ccagcagtgg gatgtgacaa   1740
agatgctgat ctcttttctc aactatgggc tttacacaaa taaaacccag taaataggtc   1800
acttttattt gcaaaatgct ggtgtgatca tgcttagctt gatagatctt ggtgagtgga   1860
gtatagagaa gtggaatgct tttacgtcaa ttcttacttt gcacggaagc tttctgttgt   1920
acctgcctcg tgcttcctgg aaagtaggct gaactttcca cttgcttcta tctgtagctg   1980
tctgcctggt tttttgtttt ttgggggttt tttttgctgc cagatgttgc ttctttttag   2040
gatcgacatt attttccaac tctatgtgtc ttgtagataa aattgtagaa aatccaatag   2100
catatctatc tatcctacat gcagagaaac ttcagtattg gacaaagaaa agacatgtcc   2160
ataggtcctg ttgtcctgac atgaggctga ttgcctgcag tgttaacagc caagccacat   2220
attgaaccct gaacagttag tcccagattt cattatttag ttatgccagc gtctcacata   2280
tgatcactct tccaactggg aggaaggtca ttagctttct gtgaacttca gcagatctcc   2340
caatgcaggc taatacatgc catttcatag atttctgcaa cccattggaa ctggtaaaca   2400
gtcctcaatt tcactcaaca gcattctaat cttcatctcc tggactcaca aactttactg   2460
tgtgactaat ttcaggagtc attaagtgat cctttcctag aaaagcagca actgcccaac   2520
tgaatcagac aaaaccagct ggactgaaag tctgacatca gctcgttttc tttctgaagt   2580
gggcttgagt actgaagatt gatatcgcta ccttaaacac ccaagaattt tatcctccat   2640
ccttgacaga acacaaccta tacaatttcc cagacacagc cctgctctgt cactatggaa   2700
tgatcttgat tcctgaagag attcctgtct ctttttcttt tagtcatttg gtcttagaca   2760
ccatttcttg caacaactct gcagaatcct tgcatcctac agggctctca gagatttggg   2820
tgctccaaag gacttcattt taaccaaact gtgcccttca agattgatca ccagcccgag   2880
gactggcctt gtttcataga gctttcttgt agggctcctg ctgcagccca tcatgcagaa   2940
gaccttgggc ttggaggtcc agacaagaaa gcttgaagag cctggggatt tagctcagta   3000
gcataaacac ttgcctggca agtgcaaggt cacaagtttg acccccagtt caaaaaaaag   3060
aaaaaagatc acgaggttgt gttttgatgc agtgtcctcc taactggtct actcatggcc   3120
```

-continued

```
attgctgtcc ttttttccat tatccacaca gcaatgagga aatcttcccc ttgtcccaca   3180
ctgtacctgc atgatcttgt ccttgccgac ttctctggtt tcgtcacttt ttccttgctc   3240
actgaattcc aatgtcatga ccttttaagt tcctgcatgc ctcagggcat ttccgcagac   3300
cagtcactgt gactcactaa ccccacgcgt ccatgagctc agctgcagtg ctgctctgca   3360
gggggactgg ctcggagctc ccagtgcgga tcacgccctc atgacaccgt tattagctct   3420
acatcctttt ccttcacaat ttgtaatgat gaattagagt aattttcatg tctcaaattg   3480
tatgtttcat gaaataaggt ctacggctat caggttcccc ttgggggctg cgaatacagc   3540
ccagtagtgg agcgttagtc cggaacacct gaaactctgg tttcatccat agatacaaag   3600
agaaaaaaag gttctctctc agactttgaa tagccacatg gttaggggag tcaataaaca   3660
tttgttacat gaatacatca acaaaaataa atagaaaagt tactatcaga ggatgcacta   3720
gctgatgggt atggatatag ttctataatc tgacgcactt tcaatagcac atttgcaaca   3780
gctagacatt gttccttctg tatgacatgt ggatactgga cagctgcagg agtgggtggc   3840
tagattctcc cccagttgct tcatctcagt ctttcttctt cctcacctct aaatagatct   3900
acaggcaagt cctctctctc tatctctctc tctctctcac ccccccccct acttcatata   3960
caacatataa attgcaaagg caggtttggc accctgactt cttgaattcc ataaattttc   4020
tttttctgtt ctgtttgttt cgtgggatcc attgattggc atcagtcttt tttttttttt   4080
tttaaatgtt tttaacatta aagagaaaat agtctaacca ttctttaaaa ttcacaaatt   4140
tcaacaggca tggtggagca tgcctataaa cctagcagcc gggtggctga ggccaaaggg   4200
ttgccagaag ttcaaggcca gcctggtata aaacagcgag ctcaagatca gcctgaacta   4260
catagtgaga accagtctta aaaaatcttt aaaaatgtat aaatttcttg aaagtccaat   4320
ttcttagaaa ccttaatcaa aaacgttcac actgggctgt gggtataact cagttgtata   4380
gcacttgcct agcatgctca gtttcctggg ttcaaacccc aaacaccaca aaatcaagca   4440
acaacaaata caaaacaaaa agctttgcat cacttgtaat aattttctag cagcacattt   4500
ttcagccaca ctcttatctg attgcttaac ttttcacata catctagagt ttattttcta   4560
aaaagactgt aagccatgtg agggaggttt atggatattc tgctttatat ccactgcaca   4620
cctctacata aaaagtgcct atccaaagtt ttctgattgt tttaagaaag caaaattaaa   4680
aagaaaaaaa tgaactaatc tttataaaaa ggtgctacac aattgtacat cctataattt   4740
tgtttcagat cctgtaacaa agggaaataa tgactgcaga caagataaag ctttatcaac   4800
ttgaagtaaa agcgatgtta actgtgaaaa agaaaatgtt aattgtgaaa agttgcctct   4860
cgtgccagaa agatgataca ttcagaaatc atcttcttaa cagaaagtta ttttcacaaa   4920
gtgctcttga ttgaaaagtt cccgtggcat ccaagcgcgg gggcacaggc ctgtgatccc   4980
agtactctgg taggctgccc aggaggctct taaatgtgag cccagcctga gcagcccagc   5040
aacctaatat gattctatct caaagtagaa aaataaaaga agacggaggt gtagctcagg   5100
gtgaaggacc tggtttcaat tcccagttct acaaaaagat aaaaactatg atttagaaat   5160
tctttgacgg tcaattttag ccgtacatgt acaacacttt tttgttatta aactctctta   5220
agaaccccat gcggaggact cagaatacaa tttaatatga atcagagaaa agcttcttga   5280
ctggaaacca aggattccct gagctacgga gaaaggaaag tgcagatggc agacaggcaa   5340
tgtcaccggg aggagcacag cctgcactgt agccttgaca agagagagca ccgagcgtgt   5400
ggacctgaaa ggacaggcca tttcgggtac tctcgggccg aagcacaagg tgaccccaaa   5460
gctcaaaaaa gaagggcttg tgtggtagat acgaatctgg gacagttcgc agtcccctgt   5520
```

-continued

```
gtcacagcgt tagctgggag ccaatggcct gaaccttagg tagtgcccca gtttctctga   5580

ctcagcctag tagtagaatg aagtcttgtg cactctagag tatcaggaag tcaaaaggat   5640

agcttggaaa ctccagaggc ctctttaaat aggattgtgg gacagtgcag caatcaccag   5700

caactggggt gctaaagtaa tgaatggcat catggacagc tgacgtggtg gcaggccctc   5760

aaggactagt ggccaggtct cccagggctc tggcactcca tgaagcagat ccgcccctct   5820

ggttatttat ccaccaaact taaattgtta ccacatgcaa gtgtcaaggc ttgcatgaga   5880

aaaatataga gaaaagcaaa tttcctgctt cttacacagc tggattctag atttgaagcc   5940

attgcataaa cttctctttt agtaagtcaa tgtccccatg catatatatg tcacatatta   6000

tgtggataaa gcatttctta ttgtcaatag catcccctaa tctagttcta ctgttattga   6060

aaagcaagtc tgactgagta gaacatgggt ctctagtaat ggaaaagaag gaaaaaaaga   6120

aggaaagtgg ccagtaaaat tcctatattg ctttttttaaa aatcatgatt cttatgcaga   6180

gttcatgaga gttcctattt tctaccatat tcattgtgac cactttaacc aaatttactg   6240

aatctggaat gttatccaaa ccatggaaaa cagaatgata ggctcaaaat cacagccata   6300

gctggatatg atgatgcatg cccataatct tggtattctg ggaagctgag gcagaaagat   6360

tacaagttca aacgcagcct ggggaattta gtgatttagc aagactcttc cttaaaataa   6420

aacaaacaaa gggcagagaa tgtagctcag tgatgcaaca taagataaat cacaatccag   6480

atagaatttt tggcgttgct gattagtaga tgtgtgacct tgagcaacct cttaactttg   6540

aatctgtttc ttgaattata aaaagtatat aataaaatat atctcactgc attattgaga   6600

gaattaaacc atatacctaa aaagctttgt aagtggataa aaaaccattg catgtggtct   6660

tattttgtgg tgaggaagac aatggagaaa gaaatattct aagtgtgaag gacatgtggg   6720

gtctaacaac agacagctca acataaaaat attaggcatg gtagtaaaag tgcttcagaa   6780

taggaaaaaa gaaattattt gggcattaga agcaaatcca aatatcctgc cttgatgtct   6840

agtacagaca acattttttt tatcagtact agggattgaa ctcatgactc cctgcttgca   6900

atgcaggtgc ttatgccact gagctaaatc cccagcccta gtacattgaa caccgacaac   6960

actgaactct ctacttttcc atcattctct tatattgaag gcatttggaa gtgattgtct   7020

attcagaaaa gatatttgag atctccttag aattcataca aggtgcattg ccctgccctt   7080

acattttctg aataatcact tccaaatgcc ttcaaataag aaattaataa ttgaggagtt   7140

ataaatcaat agctaatctt ttaattatta gatacccttc ttagttgttg ctcttactgt   7200

gaaagagctg ggctcccggt tcagctagtg cctgttgctt tgtgccatct ctagaagatt   7260

aacatgcgtg tgtgaaaacc tctgtccatg tttgaaaact gagaattagg gagcaggttt   7320

tgaatcaagc ctctgatgac actcattaag gttagaaaat aacaacagac ttaaacttag   7380

tgcagtatta gaaattctct aattgaaatg aggtgaaaac aattccatcc ctcagcattc   7440

ttgtgaagtc atgcttggtt ggaatattgt gttatcgtac ctgggatggt aggaattaca   7500

tttcaaaaca cattcaggtt gtatgtgata gtcactaaac tgtgttctca ggagggtggt   7560

agaccttatt atctaaagtc ctctagatgt cactgaagtt aggtccaagc ctcatttagc   7620

ccccacccga gttcctggag tggctgctcg actgcctgag cttcaggatc aagcacggca   7680

cagctcccac cctgcctgct ctgctaggac ccaccatccc tggggacagc tgtctcacag   7740

caaaacctca gcatccagcc gctgctacac aactgttctt gcctccccaa tctcatgctc   7800

cccttcatct caccccacca aacccatccc accaacttcc cataaaaact cagtttaata   7860
```

```
aacgcccaga agattcttct ttgcaattac tcctagaagt ctctctcgga accctgaata   7920
caggttggtt gtgttatttt gatgaataga caccatttta tctaacaatt gaaaattttg   7980
attggtttgg ggttgttagt ttaggggtag aagccaacta gaggtaaata tttgtacaat   8040
agtaaggaaa cgtaagtttg gtggcagaga aagagaaatc ttgtggaaga ctccagagcc   8100
atcaaggcag agcaagactg agggacggca gactcccagt agtgggaagc caagcgtgga   8160
tctgaaaata aatacatcaa ggggaattgc cactgatttt tttattttga aaaaattcag   8220
atatttagag aagaatatag ataaatactt gtatacottt atatacagta gaggaaggaa   8280
aggaagaagg aggagaggag agggagagac gggtcttttg cgtatgaata gaatttctca   8340
ttagagataa atgcacacac atgtatatat ttttgagcca tttgagagct ggttgtagcc   8400
atcatgacac ctcaactact aatacttcag tatgtgtctt ttaagaacaa ggccactctt   8460
ctatagacca caatgtaatt attccactta ggatgtaatg tggtataata taataagtaa   8520
tatccagtcc gtatccaaat ttccccactc tcccaataag aaccttgtaa ttctccaatt   8580
taaaagaatt aaagcatata catgcttttt ccatttttcc taccaaatcg tcaaaaataa   8640
ctagatttcc taagaacatt tttatgcctg taatttcttt ggagaaattt tcacatgccc   8700
cgttcagata ggggaggcta aaatagaaat aaccagagct ggcaggagga ggtctggtgg   8760
atgcttctat ctgaagcaac tatttggaga aaaaagcacc tgttctgttt ctgggatgc    8819
```

<210> SEQ ID NO 5
<211> LENGTH: 3498
<212> TYPE: DNA
<213> ORGANISM: Homo sapiens

<400> SEQUENCE: 5

```
gcccacccta aatacttata caggcgagtg tggacacaca cacacacaca catcctgtga     60
agaggaatga gagcacaaaa agttatatac aattcattgt aatatgaatc aggaaaaagc    120
ttcctgactt cagcctaaag attccctggg ctgaggggaa agggaatgtc cagatggcaa    180
atggagtgag gagagaactt atcctggtgg gtcactgaaa agagtgctaa gcctgctcca    240
gtggggaaga ggaagatgac agaaatgtca ggtaagtttg tgggaactga aaggggaggc    300
aatctagaag tgttctcagg caaaggccca aggagaccca agatctcaga gactaaggtg    360
ctatgtggca gatatgagtc tgggacagct tacagagtcc catacgtcac agtgtggcct    420
ggaagcagat ggatggttct ggggcctgag agtgccgcag gagtccatgg gtcttgggtc    480
acagcctgca gtttccatga ctcagcctgg cagtggaatg acttcctggg caccccaaag    540
gctttataga agttgaaagg atagttgtca aacgtgcagg agccttttaa atgggatcat    600
agggacaagg tagcaatcat ctgcatgtca ggaaacgaac actaaacagg atgatggatg    660
gcccagtgaa ggcccaggtg atagcagtct agaaccaggt accccatctc cccacatgtt    720
gacatgccac aagcacccca gaaattagtt atttccctgc agttacatat tgactaattt    780
taaattgtta ctgcttacag gatggaggct ctaaatagaa aaaaagttag agagaaacat    840
aaatttgtta tgtttttata cagctgggtt tgtgggctgc aaattgaaac cattatacaa    900
ttctctttta aaatgcaaat atccctcata cgcatatcat gtggacaaag tgtttgtttt    960
attaatagca tcccctaacc tagtttcact attaaaaggt aggtctgagt gggatgtggg   1020
tccctagtga cctagtgtga gaatagaggg tgttttgttt tgttttgttt ttgagactga   1080
gtctcgctct gttgcccagg ctggagtgca gtggcatgat ctcggctcac tgcaacctct   1140
gcctcctggg ttcaagtgat tctcatgcct cagcctcttg agtagctggg attagatgtg   1200
```

```
cccaacacca cgcctgacta atttttgtat ttttagtagg gatggggttt caccatgttg   1260
gccaggctgg tctcaaactc ctgacctcaa gtaatccacc cactttggtc tcccaaagtg   1320
ctgggattac aggcgtgagc caccacgtcc ggccttagag ggcattttaa gggaagaaga   1380
gaggagttgg gaaaggatct tctttctaat gggaagagaa agaagagaca atagaaaaag   1440
gaagaaggaa aagggcccaa tgaatgtcca atattccttt tgttttcatt gtgattctca   1500
tacagaattc ataaatactt caacctaaac cattgaaatt ggaatttaat ctgaggtatg   1560
aaaaaaatgc taggtttaaa atcacaaccc aggttgaatt tcttactttg cccattaata   1620
gatgtgtgac cttgagcatt ctcttaactt ctctgagcct cagttacttc agttgtaaaa   1680
agggtctaat aaaacacatc ccactgaatt actgagagga ttgatccaat tacatgaaag   1740
agctctgaaa caataaaaag ttgcaccatc tggggtatca gtttgcggtc gaggagacaa   1800
tggggagaaa taatgtaagt gttgagcaca tctgcggtct ttaaacagag agctcaacac   1860
aaggacatgg gcatattgga aaaaactatt tcagaagagg ggaaaaggga gaaaggggga   1920
tatgtgggta ttagaggcaa acccagatat cctgccttga ggtcaaataa ttataacatt   1980
aaatcctgtt tactgatgct tagctgtcag gctcttgctc atttaccttg gagatccatt   2040
tagaattagt gtaaggtgta attgacctgt acttagagtt ccagaatagg acaatcactt   2100
ccaaatgccc tcagtataag aaattaacag tacttggggc tttagaaatc aatgttcaac   2160
ctttcaacta ctagaaagcc tttttagtta ttgtgcttac tatgaaagcc cttggctgtc   2220
agttcaacaa gtcgttcttg ctttgtgaca tctctggaag tttaatagtt ctgtgagaaa   2280
gtccttgtca gtgttctgaa aactgggaat taggaagtcg acttccaatc aagcttcaga   2340
tgacatgcga catgcgttaa gtttagaaat aacgttagtg tttctaattt agcatcgtgt   2400
tggagtccta attatgaaat gacattaaga aaattccatt cctcagaatt cttgtgcagt   2460
agcattgggt agaaacacca ttgtgttctg tgacctgggg tagggatgat atctcaaaaa   2520
cgcatgctca ggttgcccat ggtgatagct aaactgtctt ctcaggagag gagcaggctt   2580
tattaactgg aactcaccag atttcacaga acattttgaa gggcttagga ttgtgagttt   2640
ggaggtagat gccaagcaga ggtaaacatt ttgtataaca gaagaaacat atttgatatg   2700
ggagagagac agaaatcttg tggaaaactc cagagccatc aaagctggga cagtgttaaa   2760
gacgagcacc ctggaagtga ggagccaagt gtgggttttg aggaacagat atattaaggg   2820
ggattctcac aaatgtttta ttttgacaaa tatcaataat ttagaaaagt tgcaagaata   2880
gtatagcaat tattcatata ccccttccat atagtacaca gaaaaagagg gtatatattt   2940
taataaatat ttgtgtatac acattttgtg tatagatagg cagataaata gataaagaga   3000
caaatgtgca cctgtgtata attttctgaa ctgtttgaga attggttgta agcatcacga   3060
cacttcacca ccaaatactt cagcatgtgt ctcctaagaa caaggctgtt ctctacatga   3120
ccacaacata gttatttcac ccagaaactt aaacttgata caatacaata tctaatattc   3180
agtccatatt caaatttctc ctatcatcca aataatatca ttactaatct ccaatataaa   3240
gagatttaaa acatgttttc catgttcaac ataaatgtct tctccatttt tcttacaaaa   3300
tcatcaaaaa caactacgtt tcccatttat acttttacac cagtagtttc tttggaggaa   3360
cttgcacttg tcccacatcc agattggcag gggataaaat agaaataata agagctggca   3420
gaagagaggc tggttgatgc tgattacatt caaaataact atttggagga aaaagcactg   3480
attctgttcc tggggtgt                                                 3498
```

<210> SEQ ID NO 6
<211> LENGTH: 3424
<212> TYPE: DNA
<213> ORGANISM: Homo sapiens

<400> SEQUENCE: 6
ctatgtcatt tttgctaaca tgtaatgggc ttactattgt tattttaatt aaattgataa 60
atatatattt aaaatgttct tagtttaaat ttctaatata gtaaatattg atagatacaa 120
cctacataaa caaaagctat atggagtcct caataatttt taagaatgta aagggattct 180
gaggccaaaa tgtttgagaa ttgctgggct aggattgttc aagcctctct ggggcatatg 240
ctaattatct taaagccacc caatcatcac ccaccttccc accaatgtct tcgtactcac 300
ttcttgtgag ccaatcctca cagtcaggag gcagtagtgt taggatggtt gaaagtaaaa 360
gcacaaagag attgagttca aattctttct tggctacctg tgaagtttgt aactttgact 420
aatttactgg gcccttcaaa agtctcagtt ttctcatcta taaaaggggt ataatggtag 480
tacctacctt atacgtttgt gagaattaag aaagaaggca cataatttat gttagctata 540
atagatgaaa ttctttagag ttttatttgt ggttatctaa tcataaggat tggaaagaag 600
taaagtccat gccaacttgt tttacttctt tgaaaaagag aaacaagagg tatagtaacg 660
tttaatgttt ggtttaacat gtacagtgga tgagagggca ttctatattg atctcctcaa 720
tctggccaga aaagtgttgt gatttctaac agtttatttt cacattttgt ttccctaagt 780
tcaatgagcc ctccacttct aatgaggtgg ctttagggta gagaaatcaa aaggcagttg 840
gctttgttgt gacgggcaga tctggatgga gcattataag ggtgaggctg ctgagtttcc 900
catcttgctt atacatatga tgctttgaaa cctacgctga cctgttttaa ctctggccta 960
aagacaggcc aggtgaacag aaatagagcc agcgtctcca ctggcaacac agccatcctg 1020
aagaggaatg tctgtgtgtg catctgccac cagaagtggg atgctagaga ggcattgatc 1080
tctttttgga tattgagttt tatccaagta ctcattaagt agatcccttt tattttcaaa 1140
atatctgggg ttaatgtgct taatttggtt agacctagtg agtgagctat ggagaactgg 1200
aatcatttta tatcagttcc tcatctttgc tcagattcat tctgtactgc ctgtctcttc 1260
tgcttcttag acaaagattg aacttgcagg ccaggtgcag tggctcatgc ctgtaattcc 1320
aacactttgg gaggccgagg cgggcagatc acttgaggtc gggaattcga aaccagcctg 1380
accaacatgg agaaaccccg cctctactaa aaatacaaag ttagctgggt gtggtggtgc 1440
atgcctgtaa tcccagctac tcaggaggct gaggcaggag aattgcttca acccaggaga 1500
cggagattgt ggtgagccga ggtgacgcca ttgcactcca gcctgggcaa caagagtgaa 1560
actccatctc aaaataaata aataaaaaga ttgaacttgc tacatgcttc tatctctatc 1620
tgccttctgt gctgccagct cctgcttcta gcaagaagca agagaactta tgttttttca 1680
acccctagtt ctctcctggt aaaactgtga agaatctatt tgcatatcta gccattctac 1740
atgcataaaa atgctatatc gacacaaaga aaagacttgt tcataggctc atagttctga 1800
tacaaggctt accagctgaa ttgcccacag tcaggcccta cagagaactc tgctagtttg 1860
atactcctat taatatacag ctaataggtg gtcctgtatc ctacagctgt ggccaaggtc 1920
ccacacacaa tcaattttcc attccgttag actgggaggg agattgttag ctttctatga 1980
acataagaag atcccctgat ggagccatct acataggata ggtttttgta taggtttaat 2040
gacccttcag agttggtaaa tggtccacaa tttctctaac cttcacttcc tggacccaaa 2100
gagagattgg caccaacttt actgtgtcat taatttcagg agtcattcac tgaccttctc 2160

```
cagcagtggc agcaactccc caagtcaatc aggcaataaa accagctgta ccaaaaatgt   2220

aacaacagtt caagtttact ttatccaggg gcctcaagta ttcaagattg acgtccctac   2280

ctccccatct ccaaggatgc cccccctcc ccgccatgat gatacccaag agtgagtcag    2340

tgtagccagg taccattgcc cacaggaggc tcagctttgt ccctttcaaa tgatcctccc   2400

caagggcttc tgtttctctt acttctagcc atttggtctt agccattgtg tttcctgtga   2460

tccatatgcc aagcccccac atcttacata ggccattgga aatttgggtg ctctgggaaa   2520

cctcattaat caaaccatgt cctgcaaggc tgactgccaa ccagcccaaa gactgacctg   2580

gtgtcacaga gatgtcctga aggccttctc ctcctggtga agcccatcat caagaagatg   2640

ttggacttgc agatccagac aagagaatat gaggatgttc ttaccacatc aggcagtaat   2700

acaatggcct cctaactggt gtccttgtgc ccgtgctttt cctcttctcc attccccata   2760

cagcagtcag gaaatctgat tgtgttcttc ctttgtttaa aaccctttcc tgtgtcccac   2820

atgatggcct gcatgatcct tcatgccctt gaccttgcca acctctcagg tctcatctca   2880

tgccaccttc ttcctccctg ctgtgctcag gccacatggc cttcctctag ctcctcaagt   2940

gcctagaggc ccttccagag gctggtccct ttgactcttc aactcattaa tttccactca   3000

tccttcagag ctcagctcaa atgtcacttc ctcgaggcga ctgtccttga gtccccactc   3060

gctcatcata cttttgctag ctctgcgtcc cgttccatca taggttgtaa ttacaagtct   3120

gagtaatgtg tgcctccttt agtggcttgt aaggttcatg aaggcaggat ctatatctat   3180

caaagttccc cctgaattct gagtacctac acagtaggag tctgataaat atttattgga   3240

caaataaatc aacaaaaata aatatggaaa agttgctatt gtgggcttca ccagttggtg   3300

agtacagatg tagtcctata acttcataca ctttcaattg ctctatcaca tttgtgatag   3360

ctatgaagtt tttccttcta tgcaacatgc tgctattaga cagctacagg aatgagtgaa   3420

tagc                                                                3424
```

<210> SEQ ID NO 7
<211> LENGTH: 3064
<212> TYPE: DNA
<213> ORGANISM: Homo sapiens

<400> SEQUENCE: 7

```
tagccatttg gtcttagcca ttgtgtttcc tgtgatccat atgccaagcc cccacatctt     60

acataggcca ttggaaattt gggtgctctg ggaaacctca ttaatcaaac catgtcctgc    120

aaggctgact gccaaccagc ccaaagactg acctggtgtc acagagatgt cctgaaggcc    180

ttctcctcct ggtgaagccc atcatcaaga agatgttgga cttgcagatc cagacaagag    240

aatatgagga tgttcttacc acatcaggca gtaatacaat ggcctcctaa ctggtgtcct    300

tgtgcccgtg cttttcctct tctccattcc ccatacagca gtcaggaaat ctgattgtgt    360

tcttcctttg tttaaaaccc tttcctgtgt cccacatgat ggcctgcatg atccttcatg    420

cccttgacct tgccaacctc tcaggtctca tctcatgcca ccttcttcct ccctgctgtg    480

ctcaggccac atggccttcc tctagctcct caagtgccta gaggcccttc cagaggctgg    540

tccctttgac tcttcaactc attaatttcc actcatcctt cagagctcag ctcaaatgtc    600

acttcctcga ggcgactgtc cttgagtccc cactcgctca tcatactttt gctagctctg    660

cgtcccgttc catcataggt tgtaattaca agtctgagta atgtgtgcct cctttagtgg    720

cttgtaaggt tcatgaaggc aggatctata tctatcaaag ttccccctga attctgagta    780
```

```
cctacacagt aggagtctga taaatattta ttggacaaat aaatcaacaa aaataaatat    840

ggaaaagttg ctattgtggg cttcaccagt tggtgagtac agatgtagtc ctataacttc    900

atacactttc aattgctcta tcacatttgt gatagctatg aagtttttcc ttctatgcaa    960

catgctgcta ttagacagct acaggaatga gtgaatagct tctcctctag tttcttgtcc   1020

tcaatctctc tctttcctcc cctctggccc accctaaata cttatacagg cgagtgtgga   1080

cacacacaca cacacacatc ctgtgaagag gaatgagagc acaaaaagtt atatacaatt   1140

cattgtaata tgaatcagga aaaagcttcc tgacttcagc ctaaagattc cctgggctga   1200

ggggaaaggg aatgtccaga tggcaaatgg agtgaggaga gaacttatcc tggtgggtca   1260

ctgaaaagag tgctaagcct gctccagtgg ggaagaggaa gatgacagaa atgtcaggta   1320

agtttgtggg aactgaaagg ggaggcaatc tagaagtgtt ctcaggcaaa ggcccaagga   1380

gacccaagat ctcagagact aaggtgctat gtggcagata tgagtctggg acagcttaca   1440

gagtcccata cgtcacagtg tggcctggaa gcagatggat ggttctgggg cctgagagtg   1500

ccgcaggagt ccatgggtct tgggtcacag cctgcagttt ccatgactca gcctggcagt   1560

ggaatgactt cctgggcacc ccaaaggctt tatagaagtt gaaaggatag ttgtcaaacg   1620

tgcaggagcc ttttaaatgg gatcataggg acaaggtagc aatcatctgc atgtcaggaa   1680

acgaacacta aacaggatga tggatggccc agtgaaggcc caggtgatag cagtctagaa   1740

ccaggtaccc catctcccca catgttgaca tgccacaagc accccagaaa ttagttattt   1800

ccctgcagtt acatattgac taattttaaa ttgttactgc ttacaggatg gaggctctaa   1860

atagaaaaaa agttagagag aaacataaat ttgttatgtt tttatacagc tgggtttgtg   1920

ggctgcaaat tgaaaccatt atacaattct cttttaaaat gcaaatatcc ctcatacgca   1980

tatcatgtgg acaaagtgtt tgttttatta atagcatccc ctaacctagt ttcactatta   2040

aaaggtaggt ctgagtggga tgtgggtccc tagtgaccta gtgtgagaat agagggtgtt   2100

ttgttttgtt ttgtttttga gactgagtct cgctctgttg cccaggctgg agtgcagtgg   2160

catgatctcg gctcactgca acctctgcct cctgggttca agtgattctc atgcctcagc   2220

ctcttgagta gctgggatta gatgtgccca acaccacgcc tgactaattt ttgtattttt   2280

agtagggatg gggtttcacc atgttggcca ggctggtctc aaactcctga cctcaagtaa   2340

tccacccact ttggtctccc aaagtgctgg gattacaggc gtgagccacc acgtccggcc   2400

ttagagggca ttttaaggga agaagagagg agttgggaaa ggatcttctt tctaatggga   2460

agagaaagaa gagacaatag aaaaaggaag aaggaaaagg gcccaatgaa tgtccaatat   2520

tccttttgtt ttcattgtga ttctcataca gaattcataa atacttcaac ctaaaccatt   2580

gaaattggaa tttaatctga ggtatgaaaa aaatgctagg tttaaaatca caacccaggt   2640

tgaatttctt actttgccca ttaatagatg tgtgaccttg agcattctct taacttctct   2700

gagcctcagt tacttcagtt gtaaaaaggg tctaataaaa cacatcccac tgaattactg   2760

agaggattga tccaattaca tgaaagagct ctgaaacaat aaaaagttgc accatctggg   2820

gtatcagttt gcggtcgagg agacaatggg gagaaataat gtaagtgttg agcacatctg   2880

cggtctttaa acagagagct caacacaagg acatgggcat attggaaaaa actatttcag   2940

aagaggggaa aagggagaaa gggggatatg tgggtattag aggcaaaccc agatatcctg   3000

ccttgaggtc aaataattat aacattaaat cctgtttact gatgcttagc tgtcaggctc   3060

ttgc                                                                3064
```

<210> SEQ ID NO 8
<211> LENGTH: 3352
<212> TYPE: DNA
<213> ORGANISM: Homo sapiens

<400> SEQUENCE: 8

```
ttagtctaaa ttagggatac acactcctcc ctgagctcta gacccctctc tctaactttc     60

actggatatc tccaccttga tagttcacca tgtctcaagt tcagttttgc tgaacctgaa    120

ctcataatct tcaccttaaa ctgcatcctc atccagcatt ccctaccttg gtgaccatga    180

tcaccaacct ctctcattgt aaaaacctgc ctaacacctt cccttccctc atcttccatc    240

tccagttcat tgctaagtgc tgatgttatt ctttaaatat gtcttaaagc aatctacttc    300

tctccatctt ggctcaggca ctttagtcca agctaccata acctatcctc tgaactactg    360

gcccacagaa tccactcttg cctctcccct aaaccattct ccaaaatgca ttccaagtat    420

tttttaaatt taactgaaaa tctgatcaca tcatgtgtct ttataaacac atcaatggct    480

tatccttaag ataaagacaa aagtcctaac atggcctata cagctctaca acatttttcc    540

atgcttattt ctcagctagc tacaatgttt tcctccatcc ctatgctcca gtcacaattc    600

cttcaatatg tccttgcttt gtcccacctc agagcttgcc acatgcagtt tcttctgact    660

cacatcccct tccttggaat gactgcctct cttttgatta gttaattttc tataatactg    720

cagacctcaa ctcaaatatc tcttgattcc ctcaaccacc agaccagatc agctctctca    780

ctatgcactt accatgtttt gaaattaata ctctctgaat tgtttatcac ctgtacctag    840

aatatagtgt atgatattta ttggggggc tcaatatttt gagtggatga gtaaatatat    900

tacagatagc taattattca agatttcatg ttcacattat tgctaaaaat gtagatgaag    960

taaaagtaga ttgaaatagg aggatataaa catgttggcg ctctttacat cacatacatg   1020

gattatgttt ttctttgttt gtttttagat gaagtcttgc gctgtcaccc aggctggacg   1080

gcagtggccc gagtgcacag gcaacctctg cctcccaggt tcaagcgatt ctcctccctc   1140

agcctcccga gtagctggga ttacaggagc ccaccaccaa gcccagctaa tttttgtatt   1200

tttagtagag acggggtttc gccatgttgg ccaggctggt ctgaactgct gacctcaggt   1260

gatccacccg cctcggcctc ccaaagtgct gggattacag gcgtgagcca ccatgcgcgg   1320

cccatggcat atgttatcag taatatgtaa gtatggcttc agtcaaagca aggaagttga   1380

aagtaacaat taaaaaaaaa aaagtcatca ggatccaaag ctgtggagaa aactcaacct   1440

ctgcctcctg ggttcaagca attctcctgc ctcagcctcc ctggtagctg ggattacagg   1500

tgcctgacac cacccccagc taatttttgt atttttagta gagacatggt ttcaccatgt   1560

tggtcaggct ggtcttgaac tcctgacctc aggtgatcca cccacctcag cctcccaaag   1620

tgctgggatt acaggcgtga gccactttta gaaaatgttt tcatctatct caatacctca   1680

ctacccctcc tgatattcca tctataatag caacagttgt gaaatgcact agattctaac   1740

attaacacta gatccattaa gaacagagca gaagagagtc tggatacaca aatttcacaa   1800

ttattggctc ccatcaacat atctaactca agcataaagt tgtttcagca gtagtttaag   1860

gttggttact aatgcaacac ctctttgcat gcaatggccc attaaattat cttcaacttt   1920

aaaaggttcc tttgttttta aatgcttata atgaacaaat atataccaat accttggcag   1980

aattcattaa cttaataact tcaatatgtt gttcatataa aaatttctgg taaatgagaa   2040

ctgtacatta ctgatgtgac aaggtacaca agccaatgtt gacataatgt tttcaaaatg   2100

gggtgtctgc tgtaactgaa ctaaatataa taactttatt caagaatgag tttcaatgat   2160
```

```
aggacaaaac ttgataaaat gaataaataa ataattatat gccagagttc agtaaaccct   2220

gtgtgtacac ctgaaaaagc tcaaacttgc ctagcacata tagagtccga attcagttgg   2280

gtttgtgtga aacgggtagg ttgagcccta aaaaagaggt agataaccca tataggcaga   2340

cttccttatt ttatttattt ttttctgctt cagcctcctg agtagctggg actacaggtg   2400

tgtgccacca cgtctggcta attttgtttg tttttagtag agatggggtt tcaccatatt   2460

ggccaggctg gtctcgaact cctgaccttg tgatctgcgc gcctcggcct cccaaagtgc   2520

tgggattaca ggcgtgagcc actgcgcctc gccaacttcc ttattttaaa tgccatttcc   2580

cactaaaaat aaaaccagta attctttgaa aaaaagttaa tattatgtat aggactggaa   2640

gtatataaga taaaactgga atatattgtc ataccagaaa tcaaagattt tgtcaaagac   2700

taatagttcc atgtcaaaaa gattcactaa tcaatttgca gaggctccca ctggccaaag   2760

atagagcttg atcatcaaca ggaataataa ctataatggg ttaaaacata gcaattatgt   2820

ttaaatctat aggtttatag taataatgtt aaaatcatta gtcacctttg aaagatgcta   2880

cgactcttta atccatcttg aattaatttt tgtataaggt gtaaggaagg gatccagttt   2940

cagctttcta catatggcta gccagttttc ccagcaccat ttattcaata gggaatcctt   3000

tccccattgc ttgtttttct caggtttgtc aaagatcaga tagttgtaga tatgcggtgt   3060

tatttctgag ggctctgttc tgttccattg atctatatct ctgttttggt accagtacca   3120

tgctgttttg gttactgtag ccttgtagta tagtttgaag tcaggttgca tgatgcctcc   3180

agctttgttc ttttggctta ggattgactt ggcaatgcgg gctccttttt ggttccatat   3240

gaactttaaa gtagtttttt ccaattctgt gaagaaagtc attggcagct tgatggggat   3300

gacattgaat ctataaatta ccttgggcag tatggccatt ttcacgatat tg           3352
```

<210> SEQ ID NO 9
<211> LENGTH: 7927
<212> TYPE: DNA
<213> ORGANISM: Artificial
<220> FEATURE:
<223> OTHER INFORMATION: ppZeo expression cassette of Example 1

<400> SEQUENCE: 9

```
tgggtcctat gattatgtcc ggttaaggat ccaccatggc caagttgacc agtgccgttc     60

cggtgctcac cgcgcgcgac gtcgcaggag cggtcgggtt ctggaccgac cggctcgggt    120

tctcccggga cttcgtggag gacgacttcg ccggtgtggt ccgggacgac gtgaccctgt    180

tcatcagcgc ggtccaggac caggtggtgc cggacaacac cctggcctgg gtgtgtgtgc    240

gcggcctgga cgagctgtac accgagtggt cggaggtcgt gtccacgaac ttccgggacg    300

cctccgggcc ggccatgacc gagatcggcg agcagccgtg ggggcgggag ttcgccctgc    360

gcgacccggc cggcaactgc gtgcacttcg tggccgagga gcaggactga attcgcggcc    420

gcttcccttt agtgagggtt aatgcttcga gcagacatga taagatacat tgatgagttt    480

ggacaaacca caactagaat gcagtgaaaa aaatgcttta tttgtgaaat ttgtgatgct    540

attgctttat ttgtaaccat tataagctgc aataaacaag ttaacaacaa caattgcatt    600

cattttatgt ttcaggttca gggggagatg tgggaggttt tttaaagcaa gtaaaacctc    660

tacaaatgtg gtaaaatccg ataaggatcg atccgggctg gcgtaatagc gaagaggccc    720

gcaccgatcg cccttcccaa cagttgccct actagtcggc cgtacgatcg acaccgctag    780

cattaccctg ttatccctac tcgacctgca ggcatgcaag cttggcgtaa tcatggtcat    840

agctgtttcc tgtgtgaaat tgttatccgc tcacaattcc acacaacata cgagccggaa    900
```

```
gcataaagtg taaagcctgg ggtgcctaat gagtgagcta actcacatta attgcgttgc    960
gctcactgcc cgctttccag tcgggaaacc tgtcgtgcca gctgcattaa tgaatcggcc   1020
aacgcgcggg gagaggcggt ttgcgtattg ggcgctcttc cgcttcctcg ctcactgact   1080
cgctgcgctc ggtcgttcgg ctgcggcgag cggtatcagc tcactcaaag gcggtaatac   1140
ggttatccac agaatcaggg gataacgcag gaaagaacat gtgagcaaaa ggccagcaaa   1200
aggccaggaa ccgtaaaaag gccgcgttgc tggcgttttt ccataggctc cgcccccctg   1260
acgagcatca caaaaatcga cgctcaagtc agaggtggcg aaacccgaca ggactataaa   1320
gataccaggc gtttccccct ggaagctccc tcgtgcgctc tcctgttccg accctgccgc   1380
ttaccggata cctgtccgcc tttctccctt cgggaagcgt ggcgctttct catagctcac   1440
gctgtaggta tctcagttcg gtgtaggtcg ttcgctccaa gctgggctgt gtgcacgaac   1500
cccccgttca gcccgaccgc tgcgccttat ccggtaacta tcgtcttgag tccaacccgg   1560
taagacacga cttatcgcca ctggcagcag ccactggtaa caggattagc agagcgaggt   1620
atgtaggcgg tgctacagag ttcttgaagt ggtggcctaa ctacggctac actagaagga   1680
cagtatttgg tatctgcgct ctgctgaagc cagttacctt cggaaaaaga gttggtagct   1740
cttgatccgg caaacaaacc accgctggta gcggtggttt ttttgtttgc aagcagcaga   1800
ttacgcgcag aaaaaaagga tctcaagaag atcctttgat cttttctacg gggtctgacg   1860
ctcagtggaa cgaaaactca cgttaaggga ttttggtcat gagattatca aaaaggatct   1920
tcacctagat ccttttaaat taaaaatgaa gttttaaatc aatctaaagt atatatgagt   1980
aaacttggtc tgacagttac caatgcttaa tcagtgaggc acctatctca gcgatctgtc   2040
tatttcgttc atccatagtt gcctgactcc ccgtcgtgta gataactacg atacgggagg   2100
gcttaccatc tggccccagt gctgcaatga taccgcgaga cccacgctca ccggctccag   2160
atttatcagc aataaaccag ccagccggaa gggccgagcg cagaagtggt cctgcaactt   2220
tatccgcctc catccagtct attaattgtt gccgggaagc tagagtaagt agttcgccag   2280
ttaatagttt gcgcaacgtt gttgccattg ctacaggcat cgtggtgtca cgctcgtcgt   2340
ttggtatggc ttcattcagc tccggttccc aacgatcaag gcgagttaca tgatccccca   2400
tgttgtgcaa aaaagcggtt agctccttcg gtcctccgat cgttgtcaga agtaagttgg   2460
ccgcagtgtt atcactcatg gttatggcag cactgcataa ttctcttact gtcatgccat   2520
ccgtaagatg cttttctgtg actggtgagt actcaaccaa gtcattctga gaatagtgta   2580
tgcggcgacc gagttgctct tgcccggcgt caatacggga taataccgcg ccacatagca   2640
gaactttaaa agtgctcatc attggaaaac gttcttcggg gcgaaaactc tcaaggatct   2700
taccgctgtt gagatccagt tcgatgtaac ccactcgtgc acccaactga tcttcagcat   2760
cttttacttt caccagcgtt tctgggtgag caaaaacagg aaggcaaaat gccgcaaaaa   2820
agggaataag ggcgacacgg aaatgttgaa tactcatact cttccttttt caatattatt   2880
gaagcattta tcagggttat tgtctcatga gcggatacat atttgaatgt atttagaaaa   2940
ataaacaaat aggggttccg cgcacatttc cccgaaaagt gccacctgac gtctaagaaa   3000
ccattattat catgacatta acctataaaa ataggcgtat cacgaggccc ttaaggccgc   3060
ctgatgcggt attttctcct tacgcatctg tgcggtattt cacaccgcat atggtgcact   3120
ctcagtacaa tctgctctga tgccgcatag ttaagccagc cccgacaccc gccaacaccc   3180
gctgacgcgc cctgacgggc ttgtctgctc ccggcatccg cttacagaca agctgtgacc   3240
```

-continued

```
gtctccggga gctgcatgtg tcagaggttt tcaccgtcat caccgaaacg cgcgagacga   3300
aagggcccgt accttaatta aagatctgat aattcctttg cctaattttc gagttctata   3360
gtgtcgcggc cgctatggta ccggcgcgcc gggccagata tacgcgtcct gcagctgaaa   3420
gatacaaggc cagggacagg acagtcccat ccccaggagg cagggagtat acaggctggg   3480
gaagtttgcc cttgcgtggg gtggtgatgg aggaggctca gcaagtcttc tggactgtga   3540
acctgtgtct gccactgtgt gctgggtggt ggtcatcttt cccaccaggc tgtggcctct   3600
gcaaccttca agggaggagc aggtcccatt ggctgagcac agccttgtac cgtgaactgg   3660
aacaagcagc ctccttcctg gccacaggtt ccatgtcctt atatggactc atctttgcct   3720
attgcgacac acactcagtg aacacctact acgcgctgca aagagccccg caggcctgag   3780
gtgcccccac ctcaccactc ttcctatttt tgtgtaaaaa tccagcttct tgtcaccacc   3840
tccaaggagg gggaggagga ggaaggcagg ttcctctagg ctgagccgaa tgcccctctg   3900
tggtcccacg ccactgatcg ctgcatgccc accacctggg tacacacagt ctgtgattcc   3960
cggagcagaa cggaccctgc ccacccggtc ttgtgtgcta ctcagtggac agacccaagg   4020
caagaaaggg tgacaaggac agggtcttcc caggctggct ttgagttcct agcaccgccc   4080
cgcccccaat cctctgtggc acatggagtc ttggtcccca gagtccccca gcggcctcca   4140
gatggtctgg gagggcagtt cagctgtggc tgcgcatagc agacatacaa cggacggtgg   4200
gcccagaccc aggctgtgta gacccagccc ccccgccccg cagtgcctag gtcacccact   4260
aacgccccag gccttgtctt ggctgggcgt gactgttacc ctcaaaagca ggcagctcca   4320
gggtaaaagg tgccctgccc tgtagagccc accttccttc ccagggctgc ggctgggtag   4380
gtttgtagcc ttcatcacgg gccacctcca gccactggac cgctggcccc tgccctgtcc   4440
tggggagtgt ggtcctgcga cttctaagtg gccgcaagcc acctgactcc cccaacacca   4500
cactctacct ctcaagccca ggtctctccc tagtgaccca cccagcacat ttagctagct   4560
gagccccaca gccagaggtc ctcaggccct gctttcaggg cagttgctct gaagtcggca   4620
agggggagtg actgcctggc cactccatgc cctccaagag ctccttctgc aggagcgtac   4680
agaacccagg gccctggcac ccgtgcagac cctggcccac cccacctggg cgctcagtgc   4740
ccaagagatg tccacaccta ggatgtcccg cggtgggtgg ggggcccgag agacgggcag   4800
gccgggggca ggcctggcca tgcggggccg aaccgggcac tgcccagcgt ggggcgcggg   4860
ggccacggcg cgcgccccca gcccccgggc ccagcacccc aaggcggcca acgccaaaac   4920
tctccctcct cctcttcctc aatctcgctc tcgctctttt ttttttcgc aaaaggaggg   4980
gagagggggt aaaaaaatgc tgcactgtgc ggcgaagccg gtgagtgagc ggcgcggggc   5040
caatcagcgt gcgccgttcc gaaagttgcc ttttatggct cgagcggccg cggcggcgcc   5100
ctataaaacc cagcggcgcg acgcgccacc accgccgaga ccgcgtccgc cccgcgagca   5160
cagagcctcg cctttgccga tccgccgccc gtccacaccc gccgccaggt aagcccggcc   5220
agccgaccgg ggcaggcggc tcacggcccg gccgcaggcg gccgcggccc cttcgcccgt   5280
gcagagccgc cgtctgggcc gcagcggggg gcgcatgggg ggggaaccgg accgccgtgg   5340
ggggcgcggg agaagcccct gggcctccgg agatggggga caccccacgc cagttcggag   5400
gcgcgaggcc gcgctcggga ggcgcgctcc gggggtgccg ctctcggggc gggggcaacc   5460
ggcggggtct ttgtctgagc cgggctcttg ccaatgggga tcgcagggtg ggcgcggcgg   5520
agcccccgcc aggcccggtg gggctgggg cgccattgcg cgtgcgcgct ggtcctttgg   5580
gcgctaactg cgtgcgcgct gggaattggc gctaattgcg cgtgcgcgct gggactcaag   5640
```

```
gcgctaactg cgcgtgcgtt ctggggcccg gggtgccgcg gcctgggctg gggcgaaggc   5700
gggctcggcc ggaaggggtg gggtcgccgc ggctcccggg cgcttgcgcg cacttcctgc   5760
ccgagccgct ggccgcccga gggtgtggcc gctgcgtgcg cgcgcgccga cccggcgctg   5820
tttgaaccgg gcggaggcgg ggctggcgcc cggttgggag gggttgggg cctggcttcc   5880
tgccgcgcgc cgcggggacg cctccgacca gtgtttgcct tttatggtaa taacgcggcc   5940
ggcccggctt cctttgtccc caatctgggc gcgcgccggc gcccccctggc ggcctaagga   6000
ctcggcgcgc cggaagtggc cagggcgggg gcgacctcgg ctcacagcgc gcccggctat   6060
tctcgcagct caccaccggt gagctcgttt agtgaaccgt cagatcacta gaagctttat   6120
tgcggtagtt tatcacagtt aaattgctaa cgcagtcagt gcttctgaca caacagtctc   6180
gaacttaagc tgcagtgact ctcttaaggt agccttgcag aagttggtcg tgaggcactg   6240
ggcaggtaag tatcaaggtt acaagacagg tttaaggaga ccaatagaaa ctgggcttgt   6300
cgagacagag aagactcttg cgtttctgat aggcacctat tggtcttact gacatccact   6360
ttgcctttct ctccacaggt gtccactccc agttcaatta cagctcttaa ggctagagta   6420
cttaatacga ctcactatag gctagatccg gaatggtgag caagggcgag gagctgttca   6480
ccggggtggt gcccatcctg gtcgagctgg acggcgacgt aaacggccac aagttcagcg   6540
tgtccggcga gggcgagggc gatgccacct acggcaagct gaccctgaag ttcatctgca   6600
ccaccggcaa gctgcccgtg ccctggccca ccctcgtgac caccctgacc tacggcgtgc   6660
agtgcttcag ccgctacccc gaccacatga agcagcacga cttcttcaag tccgccatgc   6720
ccgaaggcta cgtccaggag cgcaccatct tcttcaagga cgacggcaac tacaagaccc   6780
gcgccgaggt gaagttcgag ggcgacaccc tggtgaaccg catcgagctg aagggcatcg   6840
acttcaagga ggacggcaac atcctggggc acaagctgga gtacaactac aacagccaca   6900
acgtctatat catggccgac aagcagaaga acggcatcaa ggtgaacttc aagatccgcc   6960
acaacatcga ggacggcagc gtgcagctcg ccgaccacta ccagcagaac acccccatcg   7020
gcgacggccc cgtgctgctg cccgacaacc actacctgag cacccagtcc gccctgagca   7080
aagaccccaa cgagaagcgc gatcacatgg tcctgctgga gttcgtgacc gccgccggga   7140
tcactctcgg catggacgag ctgtacaaga agcttagcca tggcttcccg ccggaggtgg   7200
aggagcagga tgatggcacg ctgcccatgt cttgtgccca ggagagcggg atggaccgtc   7260
accctgcagc ctgtgcttct gctaggatca atgtgtagtc cggaacgcgt cgagcatgca   7320
tctagggcgg ccaattccgc ccctctccct cccccccccc taacgttact ggccgaagcc   7380
gcttggaata aggccggtgt gcgtttgtct atatgtgatt ttccaccata ttgccgtctt   7440
ttggcaatgt gagggcccgg aaacctggcc ctgtcttctt gacgagcatt cctaggggtc   7500
tttcccctct cgccaaagga atgcaaggtc tgttgaatgt cgtgaaggaa gcagttcctc   7560
tggaagcttc ttgaagacaa acaacgtctg tagcgaccct ttgcaggcag cggaaccccc   7620
cacctggcga caggtgcctc tgcggccaaa agccacgtgt ataagataca cctgcaaagg   7680
cggcacaacc ccagtgccac gttgtgagtt ggatagttgt ggaaagagtc aaatggctct   7740
cctcaagcgt attcaacaag gggctgaagg atgcccagaa ggtaccccat tgtatgggat   7800
ctgatctggg gcctcggtgc acatgcttta catgtgttta gtcgaggtta aaaaaacgtc   7860
taggcccccc gaaccacggg gacgtggttt tcctttgaaa aacacgatga taatatggcc   7920
acaacca                                                             7927
```

<210> SEQ ID NO 10
<211> LENGTH: 14004
<212> TYPE: DNA
<213> ORGANISM: Artificial
<220> FEATURE:
<223> OTHER INFORMATION: ppZeo expression cassette of Example 1 including STAR elements

<400> SEQUENCE: 10

```
tgggtcctat gattatgtcc ggttaaggat ccaccatggc caagttgacc agtgccgttc     60

cggtgctcac cgcgcgcgac gtcgcaggag cggtcgggtt ctggaccgac cggctcgggt    120

tctcccggga cttcgtggag gacgacttcg ccggtgtggt ccgggacgac gtgaccctgt    180

tcatcagcgc ggtccaggac caggtggtgc cggacaacac cctggcctgg gtgtgtgtgc    240

gcggcctgga cgagctgtac accgagtggt cggaggtcgt gtccacgaac ttccgggacg    300

cctccgggcc ggccatgacc gagatcggcg agcagccgtg ggggcgggag ttcgccctgc    360

gcgacccggc cggcaactgc gtgcacttcg tggccgagga gcaggactga attcgcggcc    420

gcttcccttt agtgagggtt aatgcttcga gcagacatga taagatacat tgatgagttt    480

ggacaaacca caactagaat gcagtgaaaa aaatgcttta tttgtgaaat ttgtgatgct    540

attgctttat ttgtaaccat tataagctgc aataaacaag ttaacaacaa caattgcatt    600

cattttatgt ttcaggttca gggggagatg tgggaggttt tttaaagcaa gtaaaacctc    660

tacaaatgtg gtaaaatccg ataaggatcg atccgggctg gcgtaatagc gaagaggccc    720

gcaccgatcg cccttcccaa cagttgccct actagtcggc cgtacgggat ccgatcatgc    780

cagcttaggc gacagagtga gactggacat aataacaata ataataaaaa taaataaata    840

aaacaattat ctgagaggaa aaatttgatt cataataaag agaataaagg tttttggcgt    900

gtttgttttg ttttcaccta agaacagctg ttcccctcat tgggttagtt ttatttgcaa    960

gcagaaatca tctccgcatg atttccaggg tgatggaaaa ctgaatatga atccaccttc   1020

tgccatctat tcacttgtca catttaataa gacactcatg cctattttag catgttttct   1080

tccctaccaa atgagttagt aacatcaaga gattaaaata acacaaataa gaacattgaa   1140

ggtattcaaa tgttacatac aaatattaaa cacaatatta ttataattat tcctggaaat   1200

gacattgcct ctactctcaa ggtaaaggtc atttttcttg atttaaactt ttttctcaag   1260

tttgaaatct ctaagtttca acccgtaatc tatttgcaag tttgtgcaaa ttttagggat   1320

tgaatccata gtaattagtg atttattgtg gtgtagggag acaagtcaaa agaatcagga   1380

ctgctaggta gatgactaag gaaaggatgg ttcacgaggt gacataaagc actcagaaga   1440

aaaaggtcag gaaacggagg acagaaaaaa acctaagttc tgctgggtga tgctgaattt   1500

gtcatcacaa aatctgcatt gtggaagctt tagctattga ggagattgct caagtgtaga   1560

actgagaaca ataggcagtg aacccgagag aacatcaaga gactgagaga aaatgaacca   1620

gacttccagg tgctccatgt tccaaccaac attttgtatt gtcagaagga attgagaggc   1680

aaaaggaaac ccaataaaaa ataaaacagg aaagggcata catgattacc accccttttc   1740

tcaccagctg ctcatggacc agctttctcc tagtgctatt ttcttggtca ctgcatcact   1800

ctgctaacat agtttcccca ctagctctga ggctgtccca gaggggaagc cagctgtcat   1860

ctccttcttc cacactctgt tggaggaacc tgtcattagc agctccctac taaacgcatt   1920

tatgacaaac aggcaggaga taattaacta gaaagtgaac aaactcaaac ttcagagcct   1980

ctcatttgta tgaatgccct tgtaaggtct tgggcctatt ttaatattta taaatgtgtt   2040
```

```
atttcttct aaagaaaacc accaaattgt ataagctaca gaatctgcaa aactgaggtc   2100
catccatgca ctcaggatac attcatagca tctctgagct ggaaaatatc ttaaaggtca   2160
tatatgtcct ccaacactgc aagaatctct ctggcagcat tcttttaaaa tcatcatcta   2220
aaagagggaa atccccagct gtgtttggat tttgctctgt cacttgtcca gtttccccat   2280
ccataaaagg gcaacaatat gaatttcctg ataaggtagt tgttaatata aatacaaagt   2340
gcgtagccac ttccctaaga aaaatatggg gtttctgctt cacagtctag ggagaggaaa   2400
aaaaaggggg gtcagaagtg attattatta tcattctata ttggaatgtt ttcagacata   2460
aaaagctcac cacgtcttag gccagacaga tgcattatga aagttaagct aagtcttcct   2520
catcatgagc tgcacctata tccccattac ttcttctaga actgcataat ttatttattc   2580
tttcttcaaa agtttgagag agccattctt gtcctctaag attttttttt ttttttttgg   2640
agacagagtc tccgtctgtt gcccaggctg gagtgcaatg gcactatctc agctcactgc   2700
aacctctgcc tcccagattc aagtgattct cctgcctcag cctcccgagt agctgggatt   2760
acaagcacgc accaccacaa ccagctaatt tttcgtattt tttagtagag acgaggtttt   2820
accatgttgg ccaggctggt cttgaactcc tgacctcggg tgatcgcggc cgcatgcaag   2880
cttggcgtaa tcatggtcat agctgtttcc tgtgtgaaat tgttatccgc tcacaattcc   2940
acacaacata cgagccggaa gcataaagtg taaagcctgg ggtgcctaat gagtgagcta   3000
actcacatta attgcgttgc gctcactgcc cgctttccag tcgggaaacc tgtcgtgcca   3060
gctgcattaa tgaatcggcc aacgcgcggg gagaggcggt ttgcgtattg ggcgctcttc   3120
cgcttcctcg ctcactgact cgctgcgctc ggtcgttcgg ctgcggcgag cggtatcagc   3180
tcactcaaag gcggtaatac ggttatccac agaatcaggg gataacgcag gaaagaacat   3240
gtgagcaaaa ggccagcaaa aggccaggaa ccgtaaaaag gccgcgttgc tggcgttttt   3300
ccataggctc cgcccccctg acgagcatca caaaaatcga cgctcaagtc agaggtggcg   3360
aaacccgaca ggactataaa gataccaggc gtttccccct ggaagctccc tcgtgcgctc   3420
tcctgttccg accctgccgc ttaccggata cctgtccgcc tttctccctt cgggaagcgt   3480
ggcgctttct catagctcac gctgtaggta tctcagttcg gtgtaggtcg ttcgctccaa   3540
gctgggctgt gtgcacgaac cccccgttca gcccgaccgc tgcgccttat ccggtaacta   3600
tcgtcttgag tccaacccgg taagacacga cttatcgcca ctggcagcag ccactggtaa   3660
caggattagc agagcgaggt atgtaggcgg tgctacagag ttcttgaagt ggtggcctaa   3720
ctacggctac actagaagga cagtatttgg tatctgcgct ctgctgaagc cagttacctt   3780
cggaaaaaga gttggtagct cttgatccgg caaacaaacc accgctggta gcggtggttt   3840
ttttgtttgc aagcagcaga ttacgcgcag aaaaaaagga tctcaagaag atcctttgat   3900
cttttctacg gggtctgacg ctcagtggaa cgaaaactca cgttaaggga ttttggtcat   3960
gagattatca aaaaggatct tcacctagat ccttttaaat taaaaatgaa gttttaaatc   4020
aatctaaagt atatatgagt aaacttggtc tgacagttac caatgcttaa tcagtgaggc   4080
acctatctca gcgatctgtc tatttcgttc atccatagtt gcctgactcc ccgtcgtgta   4140
gataactacg atacgggagg gcttaccatc tggccccagt gctgcaatga taccgcgaga   4200
cccacgctca ccggctccag atttatcagc aataaaccag ccagccggaa gggccgagcg   4260
cagaagtggt cctgcaactt tatccgcctc catccagtct attaattgtt gccgggaagc   4320
tagagtaagt agttcgccag ttaatagttt gcgcaacgtt gttgccattg ctacaggcat   4380
cgtggtgtca cgctcgtcgt ttggtatggc ttcattcagc tccggttccc aacgatcaag   4440
```

```
gcgagttaca tgatccccca tgttgtgcaa aaaagcggtt agctccttcg gtcctccgat   4500
cgttgtcaga agtaagttgg ccgcagtgtt atcactcatg gttatggcag cactgcataa   4560
ttctcttact gtcatgccat ccgtaagatg cttttctgtg actggtgagt actcaaccaa   4620
gtcattctga gaatagtgta tgcggcgacc gagttgctct tgcccggcgt caatacggga   4680
taataccgcg ccacatagca gaactttaaa agtgctcatc attggaaaac gttcttcggg   4740
gcgaaaactc tcaaggatct taccgctgtt gagatccagt tcgatgtaac ccactcgtgc   4800
acccaactga tcttcagcat cttttacttt caccagcgtt tctgggtgag caaaaacagg   4860
aaggcaaaat gccgcaaaaa agggaataag ggcgacacgg aaatgttgaa tactcatact   4920
cttccttttt caatattatt gaagcattta tcagggttat tgtctcatga gcggatacat   4980
atttgaatgt atttagaaaa ataaacaaat aggggttccg cgcacatttc cccgaaaagt   5040
gccacctgac gtctaagaaa ccattattat catgacatta acctataaaa ataggcgtat   5100
cacgaggccc ttaaggccgc ctgatgcggt attttctcct tacgcatctg tgcggtattt   5160
cacaccgcat atggtgcact ctcagtacaa tctgctctga tgccgcatag ttaagccagc   5220
cccgacaccc gccaacaccc gctgacgcgc cctgacgggc ttgtctgctc ccggcatccg   5280
cttacagaca agctgtgacc gtctccggga gctgcatgtg tcagaggttt tcaccgtcat   5340
caccgaaacg cgcgagacga aagggccgcg atcacccgag gtcaggagtt caagaccagc   5400
ctggccaaca tggtaaaacc tcgtctctac taaaaaatac gaaaaattag ctggttgtgg   5460
tggtgcgtgc ttgtaatccc agctactcgg gaggctgagg caggagaatc acttgaatct   5520
gggaggcaga ggttgcagtg agctgagata gtgccattgc actccagcct gggcaacaga   5580
cggagactct gtctccaaaa aaaaaaaaaa aaatcttaga ggacaagaat ggctctctca   5640
aactttgaa gaaagaataa ataaattatg cagttctaga agaagtaatg gggatatagg   5700
tgcagctcat gatgaggaag acttagctta actttcataa tgcatctgtc tggcctaaga   5760
cgtggtgagc tttttatgtc tgaaaacatt ccaatataga atgataataa taatcacttc   5820
tgaccccct ttttttcct ctccctagac tgtgaagcag aaaccccata tttttcttag   5880
ggaagtggct acgcactttg tatttatatt aacaactacc ttatcaggaa attcatattg   5940
ttgccctttt atggatgggg aaactggaca agtgacagag caaaatccaa acacagctgg   6000
ggatttccct cttttagatg atgattttaa aagaatgctg ccagagagat tcttgcagtg   6060
ttggaggaca tatatgacct ttaagatatt ttccagctca gagatgctat gaatgtatcc   6120
tgagtgcatg gatggacctc agttttgcag attctgtagc ttatacaatt tggtggtttt   6180
ctttagaaga aaataacaca tttataaata ttaaaatagg cccaagacct tacaagggca   6240
ttcatacaaa tgagaggctc tgaagtttga gtttgttcac tttctagtta attatctcct   6300
gcctgtttgt cataaatgcg tttagtaggg agctgctaat gacaggttcc tccaacagag   6360
tgtggaagaa ggagatgaca gctggcttcc cctctgggac agcctcagag ctagtgggga   6420
aactatgtta gcagagtgat gcagtgacca agaaaatagc actaggagaa agctggtcca   6480
tgagcagctg gtgagaaaag ggtggtaat catgtatgcc ctttcctgtt ttattttta   6540
ttgggtttcc ttttgcctct caattccttc tgacaataca aaatgttggt tggaacatgg   6600
agcacctgga agtctggttc attttctctc agtctcttga tgttctctcg ggttcactgc   6660
ctattgttct cagttctaca cttgagcaat ctcctcaata gctaaagctt ccacaatgca   6720
gattttgtga tgacaaattc agcatcaccc agcagaactt aggtttttt ctgtcctccg   6780
```

-continued

```
tttcctgacc tttttcttct gagtgcttta tgtcacctcg tgaaccatcc tttccttagt   6840
catctaccta gcagtcctga ttcttttgac ttgtctccct acaccacaat aaatcactaa   6900
ttactatgga ttcaatccct aaaatttgca caaacttgca aatagattac gggttgaaac   6960
ttagagattt caaacttgag aaaaaagttt aaatcaagaa aaatgacctt taccttgaga   7020
gtagaggcaa tgtcatttcc aggaataatt ataataatat tgtgtttaat atttgtatgt   7080
aacatttgaa taccttcaat gttcttattt gtgttatttt aatctcttga tgttactaac   7140
tcatttggta gggaagaaaa catgctaaaa taggcatgag tgtcttatta aatgtgacaa   7200
gtgaatagat ggcagaaggt ggattcatat tcagttttcc atcaccctgg aaatcatgcg   7260
gagatgattt ctgcttgcaa ataaaactaa cccaatgagg ggaacagctg ttcttaggtg   7320
aaaacaaaac aaacacgcca aaaaccttta ttctctttat tatgaatcaa atttttcctc   7380
tcagataatt gttttattta tttattttta ttattattgt tattatgtcc agtctcactc   7440
tgtcgcctaa gctggcatga tcggatctga taattccttt gcctaatttt cgagttctat   7500
agtgtcgcgg ccgctatggt accggcgcgc caagcttgga tcctaaaatt ttgtgaccct   7560
agagcaagta ctaactatga aagtgaaata gagaatgaag gaattattta attaagtcca   7620
gcaaaaccca accaaatcat ctgtaaaata tatttgtttt caacatccag gtattttctg   7680
tgtaaaaggt tgagttgtat gctgacttat tgggaaaaat aattgagttt tccccttcac   7740
tttgccagtg agaggaaatc agtactgtaa ttgttaaagg ttacccatac ctacctctac   7800
taccgtctag cataggtaaa gtaatgtaca ctgtgaagtt tcctgcttga ctgtaatgtt   7860
ttcagtttca tcccattgat tcaacagcta tttattcagc acttactaca accatgctgg   7920
aaacccaaga gtaaataggc tgtgttactc aacaggactg aggtacagcc gaactgtcag   7980
gcaaggttgc tgtcctttgg acttgcctgc tttctctcta tgtaggaaga agaaatggac   8040
ataccgtcca ggaaatagat atatgttaca tttccttatt ccataattaa tattaataac   8100
cctggacaga aactaccaag tttctagacc cttatagtac caccttaccc tttctggatg   8160
aatccttcac atgttgatac attttatcca aatgaaaatt ttggtactgt aggtataaca   8220
gacaaagaga gaacagaaaa ctagagatga agtttgggaa aaggtcaaga aagtaaataa   8280
tgcttctaga agacacaaaa agaaaaatga aatggtaatg ttgggaaagt tttaatacat   8340
tttgccctaa ggaaaaaaac tacttgttga aattctactt aagactggac cttttctcta   8400
aaaattgtgc ttgatgtgaa ttaaagcaac acagggaaat ttatgggctc cttctaagtt   8460
ctacccaact caccgcaaaa ctgttcctag taggtgtggt atactctttc agattctttg   8520
tgtgtatgta tatgtgtgtg tgtgtgtgtg tttgtatgtg tacagtctat atacatatgt   8580
gtacctacat gtgtgtatat ataaatatat atttacctgg atgaaatagc atattataga   8640
atattctttt ttctttaaat atatatgtgc atacatatgt atatgcacat atatacataa   8700
atgtagatat agctaggtag gcattcatgt gaaacaaaga agcctattac tttttaatgg   8760
ttgcatgata ttccatcata ggagtatagt acaacttatg taacacacat ttggcttgtt   8820
gtaaaatttt ggtattaata aaatagcaca tatcatgcaa agacaccctt gcataggtct   8880
attcattctt tgatttttac cttaggacaa aatttaaaag tagaatttct gggtcaagca   8940
gtatgctcat ttaaaatgtc attgcatatt tccaaattgt cctccagaaa agtagtaaca   9000
gtaacaattg atggactgcg tgttttctaa aacttgcatt tttttcctta ttggtgaggt   9060
ttggcatttt ccatatgttt attggcattt taattttttt tggttcatgt cttttattcc   9120
cttcctgcaa atttgtggtg tgtctcaact ttatttatac tctcattttc ataattttct   9180
```

```
aaaggaattt gactttaaaa aaataagaca gccaatgctt tggtttaatt tcattgctgc   9240
tttttgaagt gactgctgtg tttttatata cttttatatt ttgttgtttt agcaaattct   9300
tctatattat aattgtgtat gctggaacaa aaagttatat ttcttaatct agataaaata   9360
tttcaagatg ttgtaattac agtcccctct aaaatcatat aaatagacgc atagctgtgt   9420
gatttgtaat tagttatgtc cattgataga tccaagcttg gcgcgccggg ccagatatac   9480
gcgtcctgca gctgaaagat acaaggccag ggacaggaca gtcccatccc caggaggcag   9540
ggagtataca ggctggggaa gtttgccctt gcgtggggtg gtgatggagg aggctcagca   9600
agtcttctgg actgtgaacc tgtgtctgcc actgtgtgct gggtggtggt catctttccc   9660
accaggctgt ggcctctgca accttcaagg gaggagcagg tcccattggc tgagcacagc   9720
cttgtaccgt gaactggaac aagcagcctc cttcctggcc acaggttcca tgtccttata   9780
tggactcatc tttgcctatt gcgacacaca ctcagtgaac acctactacg cgctgcaaag   9840
agccccgcag gcctgaggtg cccccacctc accactcttc ctatttttgt gtaaaaatcc   9900
agcttcttgt caccacctcc aaggaggggg aggaggagga aggcaggttc ctctaggctg   9960
agccgaatgc ccctctgtgg tcccacgcca ctgatcgctg catgcccacc acctgggtac  10020
acacagtctg tgattcccgg agcagaacgg accctgccca cccggtcttg tgtgctactc  10080
agtggacaga cccaaggcaa gaaagggtga caaggacagg gtcttcccag gctggctttg  10140
agttcctagc accgccccgc cccaatcct ctgtggcaca tggagtcttg gtccccagag  10200
tcccccagcg gcctccagat ggtctgggag ggcagttcag ctgtggctgc gcatagcaga  10260
catacaacgg acggtgggcc cagacccagg ctgtgtagac ccagcccccc cgccccgcag  10320
tgcctaggtc acccactaac gccccaggcc ttgtcttggc tgggcgtgac tgttaccctc  10380
aaaagcaggc agctccaggg taaaaggtgc cctgccctgt agagcccacc ttccttccca  10440
gggctgcggc tgggtaggtt tgtagccttc atcacgggcc acctccagcc actggaccgc  10500
tggcccctgc cctgtcctgg ggagtgtggt cctgcgactt ctaagtggcc gcaagccacc  10560
tgactccccc aacaccacac tctacctctc aagcccaggt ctctccctag tgacccaccc  10620
agcacattta gctagctgag ccccacagcc agaggtcctc aggccctgct ttcagggcag  10680
ttgctctgaa gtcggcaagg gggagtgact gcctggccac tccatgccct ccaagagctc  10740
cttctgcagg agcgtacaga acccagggcc ctggcacccg tgcagaccct ggcccacccc  10800
acctgggcgc tcagtgccca agagatgtcc acacctagga tgtcccgcgg tgggtggggg  10860
gcccgagaga cgggcaggcc gggggcaggc ctggccatgc ggggccgaac cgggcactgc  10920
ccagcgtggg gcgcgggggc cacggcgcgc gcccccagcc cccgggccca gcaccccaag  10980
gcggccaacg ccaaaactct ccctcctcct cttcctcaat ctcgctctcg ctcttttttt  11040
ttttcgcaaa aggaggggag agggggtaaa aaaatgctgc actgtgcggc gaagccggtg  11100
agtgagcggc gcggggccaa tcagcgtgcg ccgttccgaa agttgccttt tatggctcga  11160
gcggccgcgg cggcgcccta taaaacccag cggcgcgacg cgccaccacc gccgagaccg  11220
cgtccgcccc gcgagcacag agcctcgcct ttgccgatcc gccgcccgtc cacacccgcc  11280
gccaggtaag cccggccagc cgaccggggc aggcggctca cggcccggcc gcaggcggcc  11340
gcggcccctt cgcccgtgca gagccgccgt ctgggccgca gcggggggcg catggggggg  11400
gaaccggacc gccgtggggg gcgcgggaga agcccctggg cctccggaga tgggggacac  11460
cccacgccag ttcggaggcg cgaggccgcg ctcgggaggc gcgctccggg ggtgccgctc  11520
```

```
tcggggcggg ggcaaccggc ggggtctttg tctgagccgg gctcttgcca atggggatcg  11580
cagggtgggc gcggcggagc cccgcgcagg cccggtgggg gctggggcgc cattgcgcgt  11640
gcgcgctggt cctttgggcg ctaactgcgt gcgcgctggg aattggcgct aattgcgcgt  11700
gcgcgctggg actcaaggcg ctaactgcgc gtgcgttctg gggcccgggg tgccgcggcc  11760
tgggctgggg cgaaggcggg ctcggccgga aggggtgggg tcgccgcggc tcccgggcgc  11820
ttgcgcgcac ttcctgcccg agccgctggc cgcccgaggg tgtggccgct gcgtgcgcgc  11880
gcgccgaccc ggcgctgttt gaaccgggcg gaggcggggc tggcgcccgg ttgggagggg  11940
gttggggcct ggcttcctgc cgcgcgccgc ggggacgcct ccgaccagtg tttgcctttt  12000
atggtaataa cgcggccggc ccggcttcct ttgtccccaa tctgggcgcg cgccggcgcc  12060
ccctggcggc ctaaggactc ggcgcgccgg aagtggccag ggcgggggcg acctcggctc  12120
acagcgcgcc cggctattct cgcagctcac caccggtgag ctcgtttagt gaaccgtcag  12180
atcactagaa gctttattgc ggtagtttat cacagttaaa ttgctaacgc agtcagtgct  12240
tctgacacaa cagtctcgaa cttaagctgc agtgactctc ttaaggtagc cttgcagaag  12300
ttggtcgtga ggcactgggc aggtaagtat caaggttaca agacaggttt aaggagacca  12360
atagaaactg ggcttgtcga gacagagaag actcttgcgt ttctgatagg cacctattgg  12420
tcttactgac atccactttg cctttctctc cacaggtgtc cactcccagt tcaattacag  12480
ctcttaaggc tagagtactt aatacgactc actataggct agatccggaa tggtgagcaa  12540
gggcgaggag ctgttcaccg ggtggtgcc catcctggtc gagctggacg gcgacgtaaa  12600
cggccacaag ttcagcgtgt ccggcgaggg cgagggcgat gccacctacg gcaagctgac  12660
cctgaagttc atctgcacca ccggcaagct gcccgtgccc tggcccaccc tcgtgaccac  12720
cctgacctac ggcgtgcagt gcttcagccg ctaccccgac cacatgaagc agcacgactt  12780
cttcaagtcc gccatgcccg aaggctacgt ccaggagcgc accatcttct tcaaggacga  12840
cggcaactac aagacccgcg ccgaggtgaa gttcgagggc gacaccctgg tgaaccgcat  12900
cgagctgaag ggcatcgact tcaaggagga cggcaacatc ctggggcaca agctggagta  12960
caactacaac agccacaacg tctatatcat ggccgacaag cagaagaacg gcatcaaggt  13020
gaacttcaag atccgccaca acatcgagga cggcagcgtg cagctcgccg accactacca  13080
gcagaacacc cccatcggcg acggccccgt gctgctgccc gacaaccact acctgagcac  13140
ccagtccgcc ctgagcaaag accccaacga gaagcgcgat cacatggtcc tgctggagtt  13200
cgtgaccgcc gccgggatca ctctcggcat ggacgagctg tacaagaagc ttagccatgg  13260
cttcccgccg gaggtggagg agcaggatga tggcacgctg cccatgtctt gtgcccagga  13320
gagcgggatg gaccgtcacc ctgcagcctg tgcttctgct aggatcaatg tgtagtccgg  13380
aacgcgtcga gcatgcatct agggcggcca attccgcccc tctccctccc ccccccctaa  13440
cgttactggc cgaagccgct tggaataagg ccggtgtgcg tttgtctata tgtgattttc  13500
caccatattg ccgtcttttg gcaatgtgag ggcccggaaa cctggccctg tcttcttgac  13560
gagcattcct aggggtcttt cccctctcgc caaaggaatg caaggtctgt tgaatgtcgt  13620
gaaggaagca gttcctctgg aagcttcttg aagacaaaca acgtctgtag cgaccctttg  13680
caggcagcgg aacccccac ctggcgacag gtgcctctgc ggccaaaagc cacgtgtata  13740
agatacacct gcaaaggcgg cacaacccca gtgccacgtt gtgagttgga tagttgtgga  13800
aagagtcaaa tggctctcct caagcgtatt caacaagggg ctgaaggatg cccagaaggt  13860
accccattgt atgggatctg atctggggcc tcggtgcaca tgctttacat gtgtttagtc  13920
```

gaggttaaaa aaacgtctag gcccccgaa ccacggggac gtggttttcc tttgaaaaac 13980
acgatgataa tatggccaca acca 14004

<210> SEQ ID NO 11
<211> LENGTH: 7
<212> TYPE: RNA
<213> ORGANISM: Artificial
<220> FEATURE:
<223> OTHER INFORMATION: Kozak sequence
<220> FEATURE:
<221> NAME/KEY: misc_feature
<222> LOCATION: (2)..(3)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u

<400> SEQUENCE: 11 annaugn 7

<210> SEQ ID NO 12
<211> LENGTH: 7
<212> TYPE: RNA
<213> ORGANISM: Artificial
<220> FEATURE:
<223> OTHER INFORMATION: Kozak sequence
<220> FEATURE:
<221> NAME/KEY: misc_feature
<222> LOCATION: (2)..(3)
<223> OTHER INFORMATION: n is a, c, g, or u

<400> SEQUENCE: 12 gnnaugg 7

<210> SEQ ID NO 13
<211> LENGTH: 10
<212> TYPE: RNA
<213> ORGANISM: Artificial
<220> FEATURE:
<223> OTHER INFORMATION: Kozak sequence

<400> SEQUENCE: 13 gccrccaugg 10

<210> SEQ ID NO 14
<211> LENGTH: 270
<212> TYPE: DNA
<213> ORGANISM: Artificial
<220> FEATURE:
<223> OTHER INFORMATION: synthetic pp90

<400> SEQUENCE: 14
gaaattgctt ctggtggcgc tcccctctct aaggaagtcg gggaagcggt tgccaagagg 60
ttccatctgc caggtatcag gcaaggatat gggctcactg agactacatc agctattctg 120
attacacccg agggggatga taaaccgggc gcggtcggta aagttgttcc attttttgaa 180
gcgaaggttg ggatctggat acgggaaaac gctgggcgtt aatcaaagag gcgaactgtg 240
tgtgagaggt cctatgatta tgtccggtta 270

<210> SEQ ID NO 15
<211> LENGTH: 375
<212> TYPE: DNA
<213> ORGANISM: Artificial
<220> FEATURE:

<223> OTHER INFORMATION: synthetic wt Zeo resistance gene

<400> SEQUENCE: 15
atggccaagt tgaccagtgc cgttccggtg ctcaccgcgc gcgacgtcgc cggagcggtc 60
gagttctgga ccgaccggct cgggttctcc cgggacttcg tggaggacga cttcgccggt 120
gtggtccggg acgacgtgac cctgttcatc agcgcggtcc aggaccaggt ggtgccggac 180
aacaccctgg cctgggtgtg ggtgcgcggc ctggacgagc tgtacgccga gtggtcggag 240
gtcgtgtcca cgaacttccg ggacgcctcc gggccggcca tgaccgagat cggcgagcag 300
ccgtgggggc gggagttcgc cctgcgcgac ccggccggca actgcgtgca cttcgtggcc 360
gaggagcagg actga 375

<210> SEQ ID NO 16
<211> LENGTH: 411
<212> TYPE: DNA
<213> ORGANISM: Artificial
<220> FEATURE:
<223> OTHER INFORMATION: bicistronic coding sequence of pp8 Zeo EPP5

<400> SEQUENCE: 16
atgggtccta tgattatgtc cggttaagga tccaccatgg ccaagttgac cagtgccgtt 60
ccggtgctca ccgcgcgcga cgtcgcagga gcggtcgggt tctggaccga ccggctcggg 120
ttctcccggg acttcgtgga ggacgacttc gccggtgtgg tccgggacga cgtgaccctg 180
ttcatcagcg cggtccagga ccaggtggtg ccggacaaca ccctggcctg ggtgtgtgtg 240
cgcggcctgg acgagctgta caccgagtgg tcggaggtcg tgtccacgaa cttccgggac 300
gcctccgggc cggccatgac cgagatcggc gagcagccgt gggggcggga gttcgccctg 360
cgcgacccgg ccggcaactg cgtgcacttc gtggccgagg agcaggactg a 411

<210> SEQ ID NO 17
<211> LENGTH: 3500
<212> TYPE: DNA
<213> ORGANISM: Artificial
<220> FEATURE:
<223> OTHER INFORMATION: human beta actin promoter fragment

<400> SEQUENCE: 17
gccccagtga cagctccgaa agctccctta cagggcaaag ttcccaagca cagaagagaa 60
cctgttcact tctcccctgc tcggcccgcc ccctggccag gcacctctac ttcctctttt 120
cctgctccgc tgcttgcttt ctctcttcag ctcctccctg cccctcaccc caggctgctc 180
ggccacctcc aacctgccac ctgaggacac ccaggcagtc actcattcaa cagcgaggag 240
ccctggggtg ggtgtagtgg gaaggagtgg gggtgacgga gaccctggga gggctcgcag 300
cctggtggct gaggcccagt tctaaatgcc agctgcaagc cttggtctga ggtagggagg 360
aaggcgtggc tgcagaggct aaaacgcttc cccaaagagg ggctttctgg gatgggactt 420
gaagggtgca taggagagca ctaggaagtg gccgctgcag acagagggaa ccacaagcca 480
ggaggacagg ccaggaatgc tgcagcccgg ggcggggtgg ggctggagct cctgtctctt 540
ggccagctga atggaggccc agtggcaaca caggtcctgc ctggggatca ggtctgctct 600
gcaccccacc ttgctgcctg gagccgccca cctgacaacc tctcatccct gctctgcaga 660
tccggtccca tccccactgc ccaccccacc cccccagcac tccacccagt tcaacgttcc 720
acgaaccccc agaaccagcc ctcatcaaca ggcagcaaga agggcccccc gcccatcgcc 780
ccacaacgcc agccgggtga acgttggcag gtcctgaggc agctggcaag acgcctgcag 840

```
ctgaaagata caaggccagg gacaggacag tcccatcccc aggaggcagg gagtatacag    900

gctggggaag tttgcccttg cgtggggtgg tgatggagga ggctcagcaa gtcttctgga    960

ctgtgaacct gtgtctgcca ctgtgtgctg ggtggtggtc atctttccca ccaggctgtg   1020

gcctctgcaa ccttcaaggg aggagcaggt cccattggct gagcacagcc ttgtaccgtg   1080

aactggaaca agcagcctcc ttcctggcca caggttccat gtccttatat ggactcatct   1140

ttgcctattg cgacacacac tcagtgaaca cctactacgc gctgcaaaga gccccgcagg   1200

cctgaggtgc ccccacctca ccactcttcc tatttttgtg taaaaatcca gcttcttgtc   1260

accacctcca aggaggggga ggaggaggaa ggcaggttcc tctaggctga gccgaatgcc   1320

cctctgtggt cccacgccac tgatcgctgc atgcccacca cctgggtaca cacagtctgt   1380

gattcccgga gcagaacgga ccctgcccac ccggtcttgt gtgctactca gtggacagac   1440

ccaaggcaag aaagggtgac aaggacaggg tcttcccagg ctggctttga gttcctagca   1500

ccgccccgcc cccaatcctc tgtggcacat ggagtcttgg tccccagagt cccccagcgg   1560

cctccagatg gtctgggagg gcagttcagc tgtggctgcg catagcagac atacaacgga   1620

cggtgggccc agacccaggc tgtgtagacc cagccccccc gccccgcagt gcctaggtca   1680

cccactaacg ccccaggcct tgtcttggct gggcgtgact gttaccctca aaagcaggca   1740

gctccagggt aaaaggtgcc ctgccctgta gagcccacct tccttcccag ggctgcggct   1800

gggtaggttt gtagccttca tcacgggcca cctccagcca ctggaccgct ggcccctgcc   1860

ctgtcctggg gagtgtggtc ctgcgacttc taagtggccg caagccacct gactccccca   1920

acaccacact ctacctctca agcccaggtc tctccctagt gacccaccca gcacatttag   1980

ctagctgagc cccacagcca gaggtcctca ggccctgctt tcagggcagt tgctctgaag   2040

tcggcaaggg ggagtgactg cctggccact ccatgccctc caagagctcc ttctgcagga   2100

gcgtacagaa cccagggccc tggcacccgt gcagaccctg gcccacccca cctgggcgct   2160

cagtgcccaa gagatgtcca cacctaggat gtcccgcggt gggtgggggg cccgagagac   2220

gggcaggccg ggggcaggcc tggccatgcg gggccgaacc gggcactgcc cagcgtgggg   2280

cgcgggggcc acggcgcgcg cccccagccc ccgggcccag caccccaagg cggccaacgc   2340

caaaactctc cctcctcctc ttcctcaatc tcgctctcgc tctttttttt tttcgcaaaa   2400

ggaggggaga gggggtaaaa aaatgctgca ctgtgcggcg aagccggtga gtgagcggcg   2460

cggggccaat cagcgtgcgc cgttccgaaa gttgcctttt atggctcgag cggccgcggc   2520

ggcgccctat aaaacccagc ggcgcgacgc gccaccaccg ccgagaccgc gtccgccccg   2580

cgagcacaga gcctcgcctt tgccgatccg ccgcccgtcc acacccgccg ccaggtaagc   2640

ccggccagcc gaccggggca ggcggctcac ggcccggccg caggcggccg cggccccttc   2700

gcccgtgcag agccgccgtc tgggccgcag cggggggcgc atgggggggg aaccggaccg   2760

ccgtgggggg cgcgggagaa gcccctgggc ctccggagat gggggacacc ccacgccagt   2820

tcggaggcgc gaggccgcgc tcgggaggcg cgctccgggg gtgccgctct cggggcgggg   2880

gcaaccggcg gggtctttgt ctgagccggg ctcttgccaa tggggatcgc agggtgggcg   2940

cggcggagcc cccgccaggc ccggtggggg ctggggcgcc attgcgcgtg cgcgctggtc   3000

ctttgggcgc taactgcgtg cgcgctggga attggcgcta attgcgcgtg cgcgctggga   3060

ctcaaggcgc taactgcgcg tgcgttctgg ggcccggggt gccgcggcct gggctggggc   3120

gaaggcgggc tcggccggaa ggggtggggt cgccgcggct cccgggcgct tgcgcgcact   3180
```

```
tcctgcccga gccgctggcc gcccgagggt gtggccgctg cgtgcgcgcg cgccgacccg   3240

gcgctgtttg aaccgggcgg aggcggggct ggcgcccggt tgggaggggg ttggggcctg   3300

gcttcctgcc gcgcgccgcg gggacgcctc cgaccagtgt ttgcctttta tggtaataac   3360

gcggccggcc cggcttcctt tgtccccaat ctgggcgcgc gccggcgccc cctggcggcc   3420

taaggactcg gcgcgccgga agtggccagg gcgggggcga cctcggctca cagcgcgccc   3480

ggctattctc gcagctcacc                                               3500


<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18

ggagcgtctg cagaatggtg acagg                                           25


<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19

ctgaaggagt ctcaaactga agagag                                          26


<210> SEQ ID NO 20
<211> LENGTH: 25
<212> TYPE: DNA
<213> ORGANISM: Artificial
<220> FEATURE:
<223> OTHER INFORMATION: primer

<400> SEQUENCE: 20

tgtttgcatt cctgtagccc acaag                                           25


<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21

gtgatgtaaa tctttgcaat tcttc                                           25


<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22

tagtcttttg tatgtgataa atctc                                           25


<210> SEQ ID NO 23
<211> LENGTH: 25
<212> TYPE: DNA
<213> ORGANISM: Artificial
<220> FEATURE:
<223> OTHER INFORMATION: primer
```

<400> SEQUENCE: 23
gcccacccta aatacttata caggc 25

<210> SEQ ID NO 24
<211> LENGTH: 29
<212> TYPE: DNA
<213> ORGANISM: Artificial
<220> FEATURE:
<223> OTHER INFORMATION: primer

<400> SEQUENCE: 24
actatgtcat ttttgctaac atgtaatgg 29

<210> SEQ ID NO 25
<211> LENGTH: 25
<212> TYPE: DNA
<213> ORGANISM: Artificial
<220> FEATURE:
<223> OTHER INFORMATION: primer

<400> SEQUENCE: 25
ggggactagt ggagaaggtg cgaca 25

<210> SEQ ID NO 26
<211> LENGTH: 27
<212> TYPE: DNA
<213> ORGANISM: Artificial
<220> FEATURE:
<223> OTHER INFORMATION: primer

<400> SEQUENCE: 26
cctcttggtg ggaaggtgtg ttcataa 27

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcattgagca gtggtttgta gttctccttg 30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
ttagtctaaa ttagggatac acactcctcc 30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
atggaagata gtggaaccaa cttggaaagc 30

<210> SEQ ID NO 30

<211> LENGTH: 29
<212> TYPE: DNA
<213> ORGANISM: Artificial
<220> FEATURE:
<223> OTHER INFORMATION: primer

<400> SEQUENCE: 30
agctttagct actccagctt tctgggtgt 29

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
tttcactact tcccctgtat aacctccacg 30

<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
gcaccacgtt tgagcacctc tggag 25

<210> SEQ ID NO 33
<211> LENGTH: 31
<212> TYPE: DNA
<213> ORGANISM: Artificial
<220> FEATURE:
<223> OTHER INFORMATION: primer

<400> SEQUENCE: 33
tgtgatttgg aataaaacct ccctgaagag g 31

<210> SEQ ID NO 34
<211> LENGTH: 28
<212> TYPE: DNA
<213> ORGANISM: Artificial
<220> FEATURE:
<223> OTHER INFORMATION: primer

<400> SEQUENCE: 34
ccagacagct atgagcactc agtggact 28

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
aaatacattt aaaaatctgg cagagccggg 30

<210> SEQ ID NO 36
<211> LENGTH: 25
<212> TYPE: DNA
<213> ORGANISM: Artificial
<220> FEATURE:
<223> OTHER INFORMATION: primer

<400> SEQUENCE: 36
atcaacgcca ccgttcttcc atgtc 25

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
tactatcttg ggatcattaa tggctgcagg 30

<210> SEQ ID NO 38
<211> LENGTH: 25
<212> TYPE: DNA
<213> ORGANISM: Artificial
<220> FEATURE:
<223> OTHER INFORMATION: primer

<400> SEQUENCE: 38
cgcgaacagc ctcagcttct gaatg 25

<210> SEQ ID NO 39
<211> LENGTH: 25
<212> TYPE: DNA
<213> ORGANISM: Artificial
<220> FEATURE:
<223> OTHER INFORMATION: primer

<400> SEQUENCE: 39
agactctcgc tctgttgcca ggctg 25

<210> SEQ ID NO 40
<211> LENGTH: 25
<212> TYPE: DNA
<213> ORGANISM: Artificial
<220> FEATURE:
<223> OTHER INFORMATION: primer

<400> SEQUENCE: 40
acaaagagtc tggtgggtga ctgtg 25

<210> SEQ ID NO 41
<211> LENGTH: 25
<212> TYPE: DNA
<213> ORGANISM: Artificial
<220> FEATURE:
<223> OTHER INFORMATION: primer

<400> SEQUENCE: 41
cgttctaaaa agccttcctt caaag 25

<210> SEQ ID NO 42
<211> LENGTH: 24
<212> TYPE: DNA
<213> ORGANISM: Artificial
<220> FEATURE:
<223> OTHER INFORMATION: primer

<400> SEQUENCE: 42
tcttaatggc ttgatgagcc acac 24

<210> SEQ ID NO 43
<211> LENGTH: 24
<212> TYPE: DNA

<213> ORGANISM: Artificial
<220> FEATURE:
<223> OTHER INFORMATION: primer

<400> SEQUENCE: 43
taccattcaa ttctcccgtc tgac 24

<210> SEQ ID NO 44
<211> LENGTH: 24
<212> TYPE: DNA
<213> ORGANISM: Artificial
<220> FEATURE:
<223> OTHER INFORMATION: primer

<400> SEQUENCE: 44
acaccccagg aacagaatca gtgc 24

<210> SEQ ID NO 45
<211> LENGTH: 30
<212> TYPE: DNA
<213> ORGANISM: Artificial
<220> FEATURE:
<223> OTHER INFORMATION: primer

<400> SEQUENCE: 45
gctattcact cattcctgta gctgtctaat 30

<210> SEQ ID NO 46
<211> LENGTH: 26
<212> TYPE: DNA
<213> ORGANISM: Artificial
<220> FEATURE:
<223> OTHER INFORMATION: primer

<400> SEQUENCE: 46
ccagggcttc cagagagtgt cgttta 26

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47
aagcctgccc aaagatgcta ggacg 25

<210> SEQ ID NO 48
<211> LENGTH: 27
<212> TYPE: DNA
<213> ORGANISM: Artificial
<220> FEATURE:
<223> OTHER INFORMATION: primer

<400> SEQUENCE: 48
ttatgaacac accttcccac caagagg 27

<210> SEQ ID NO 49
<211> LENGTH: 25
<212> TYPE: DNA
<213> ORGANISM: Artificial
<220> FEATURE:
<223> OTHER INFORMATION: primer

<400> SEQUENCE: 49
caatatcgtg aaaatggcca tactg 25

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
tcaggggtac atgtgcaggt ttgttacata 30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
tggaaaggta gtcttcaagc ttggaaattc 30

<210> SEQ ID NO 52
<211> LENGTH: 28
<212> TYPE: DNA
<213> ORGANISM: Artificial
<220> FEATURE:
<223> OTHER INFORMATION: primer

<400> SEQUENCE: 52
aagatctgtg agagcagtgt ggattccc 28

<210> SEQ ID NO 53
<211> LENGTH: 25
<212> TYPE: DNA
<213> ORGANISM: Artificial
<220> FEATURE:
<223> OTHER INFORMATION: primer

<400> SEQUENCE: 53
cagttttcca gggggcactc agagc 25

<210> SEQ ID NO 54
<211> LENGTH: 22
<212> TYPE: DNA
<213> ORGANISM: Artificial
<220> FEATURE:
<223> OTHER INFORMATION: primer

<400> SEQUENCE: 54
gcgggcgtta gcgccttttt ag 22

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
cagggaggtt ttattccaaa tcaca 25

<210> SEQ ID NO 56
<211> LENGTH: 26
<212> TYPE: DNA
<213> ORGANISM: Artificial
<220> FEATURE:

<223> OTHER INFORMATION: primer

<400> SEQUENCE: 56
tgatggagtt ggatcccagt gtttgg 26

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
cagtgccacc tttctcttgg ttaggatttt 30

<210> SEQ ID NO 58
<211> LENGTH: 28
<212> TYPE: DNA
<213> ORGANISM: Artificial
<220> FEATURE:
<223> OTHER INFORMATION: primer

<400> SEQUENCE: 58
caggcatcca gttctgagct ttctctct 28

<210> SEQ ID NO 59
<211> LENGTH: 27
<212> TYPE: DNA
<213> ORGANISM: Artificial
<220> FEATURE:
<223> OTHER INFORMATION: primer

<400> SEQUENCE: 59
ggtgggaaac tgctccttca ctttgct 27

<210> SEQ ID NO 60
<211> LENGTH: 28
<212> TYPE: DNA
<213> ORGANISM: Artificial
<220> FEATURE:
<223> OTHER INFORMATION: primer

<400> SEQUENCE: 60
gatacacact cctccctgag ctctagac 28

<210> SEQ ID NO 61
<211> LENGTH: 25
<212> TYPE: DNA
<213> ORGANISM: Artificial
<220> FEATURE:
<223> OTHER INFORMATION: primer

<400> SEQUENCE: 61
aatgagagag gttgggatca tggtc 25

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
gtcctaacat ggcctataca gctctacaac 30

<210> SEQ ID NO 63
<211> LENGTH: 24
<212> TYPE: DNA
<213> ORGANISM: Artificial
<220> FEATURE:
<223> OTHER INFORMATION: primer

<400> SEQUENCE: 63
cagaagaaac tgcatgtggc aagc 24

<210> SEQ ID NO 64
<211> LENGTH: 22
<212> TYPE: DNA
<213> ORGANISM: Artificial
<220> FEATURE:
<223> OTHER INFORMATION: primer

<400> SEQUENCE: 64
tcaacctctg cctcctgggt tc 22

<210> SEQ ID NO 65
<211> LENGTH: 24
<212> TYPE: DNA
<213> ORGANISM: Artificial
<220> FEATURE:
<223> OTHER INFORMATION: primer

<400> SEQUENCE: 65
ttcaagacca gcctgaccaa catg 24

<210> SEQ ID NO 66
<211> LENGTH: 24
<212> TYPE: DNA
<213> ORGANISM: Artificial
<220> FEATURE:
<223> OTHER INFORMATION: primer

<400> SEQUENCE: 66
ttgtgtgaaa cgggtaggtt gagc 24

<210> SEQ ID NO 67
<211> LENGTH: 24
<212> TYPE: DNA
<213> ORGANISM: Artificial
<220> FEATURE:
<223> OTHER INFORMATION: primer

<400> SEQUENCE: 67
gccaatatgg tgaaacccca tctc 24

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
ctctgttttg gtaccagtac catgctg 27

<210> SEQ ID NO 69
<211> LENGTH: 23
<212> TYPE: DNA
<213> ORGANISM: Artificial
<220> FEATURE:
<223> OTHER INFORMATION: primer

<400> SEQUENCE: 69
atatggaacc aaaaaggagc ccg 23

<210> SEQ ID NO 70
<211> LENGTH: 28
<212> TYPE: DNA
<213> ORGANISM: Artificial
<220> FEATURE:
<223> OTHER INFORMATION: primer

<400> SEQUENCE: 70
aagcttcctg acttcagcct aaagattc 28

<210> SEQ ID NO 71
<211> LENGTH: 31
<212> TYPE: DNA
<213> ORGANISM: Artificial
<220> FEATURE:
<223> OTHER INFORMATION: primer

<400> SEQUENCE: 71
cttacctgac atttctgtca tcttcctctt c 31

<210> SEQ ID NO 72
<211> LENGTH: 28
<212> TYPE: DNA
<213> ORGANISM: Artificial
<220> FEATURE:
<223> OTHER INFORMATION: primer

<400> SEQUENCE: 72
ctcatacgca tatcatgtgg acaaagtg 28

<210> SEQ ID NO 73
<211> LENGTH: 24
<212> TYPE: DNA
<213> ORGANISM: Artificial
<220> FEATURE:
<223> OTHER INFORMATION: primer

<400> SEQUENCE: 73
ggcaacagag cgagactcag tctc 24

<210> SEQ ID NO 74
<211> LENGTH: 29
<212> TYPE: DNA
<213> ORGANISM: Artificial
<220> FEATURE:
<223> OTHER INFORMATION: primer

<400> SEQUENCE: 74
atcccactga attactgaga ggattgatc 29

<210> SEQ ID NO 75
<211> LENGTH: 25
<212> TYPE: DNA
<213> ORGANISM: Artificial
<220> FEATURE:
<223> OTHER INFORMATION: primer

<400> SEQUENCE: 75
ccatgtcctt gtgttgagct ctctg 25

<210> SEQ ID NO 76
<211> LENGTH: 30

<212> TYPE: DNA
<213> ORGANISM: Artificial
<220> FEATURE:
<223> OTHER INFORMATION: primer

<400> SEQUENCE: 76
atagctaaac tgtcttctca ggagaggagc 30

<210> SEQ ID NO 77
<211> LENGTH: 25
<212> TYPE: DNA
<213> ORGANISM: Artificial
<220> FEATURE:
<223> OTHER INFORMATION: primer

<400> SEQUENCE: 77
ctctgcttgg catctacctc caaac 25

<210> SEQ ID NO 78
<211> LENGTH: 25
<212> TYPE: DNA
<213> ORGANISM: Artificial
<220> FEATURE:
<223> OTHER INFORMATION: primer

<400> SEQUENCE: 78
gaacttgcac ttgtcccaca tccag 25

<210> SEQ ID NO 79
<211> LENGTH: 27
<212> TYPE: DNA
<213> ORGANISM: Artificial
<220> FEATURE:
<223> OTHER INFORMATION: primer

<400> SEQUENCE: 79
caggaacaga atcagtgctt tttcctc 27

<210> SEQ ID NO 80
<211> LENGTH: 20
<212> TYPE: DNA
<213> ORGANISM: Artificial
<220> FEATURE:
<223> OTHER INFORMATION: Synthetic primer P15 Forward

<400> SEQUENCE: 80
ggagcagaac ccaactgcgc 20

<210> SEQ ID NO 81
<211> LENGTH: 21
<212> TYPE: DNA
<213> ORGANISM: Artificial
<220> FEATURE:
<223> OTHER INFORMATION: Synthetic primer P15 Reverse

<400> SEQUENCE: 81
ccaggcgtca cacacatcca g 21

<210> SEQ ID NO 82
<211> LENGTH: 27
<212> TYPE: DNA
<213> ORGANISM: Artificial
<220> FEATURE:
<223> OTHER INFORMATION: Synthetic primer RB1 Forward

<400> SEQUENCE: 82

```
gtgacagagt gctcaaaaga agtgctg                                          27


<210> SEQ ID NO 83
<211> LENGTH: 25
<212> TYPE: DNA
<213> ORGANISM: Artificial
<220> FEATURE:
<223> OTHER INFORMATION: Synthetic primer RB1 Reverse

<400> SEQUENCE: 83

ggactccgct gggagatgtt tactc                                            25
```

INTERGENIC ELEMENTS FOR ENHANCING GENE EXPRESSION

CROSS-REFERENCE TO RELATED APPLICATION(S)

This application is the National Phase of International Patent Application No. PCT/NL2011/050433, filed Jun. 15, 2011, published as WO 2011/159157, which claims the benefit of Provisional Application Ser. No. 61/354,822, filed Jun. 15, 2010. The contents of these applications are herein incorporated by reference in their entirety.

FIELD OF THE INVENTION

The present invention relates to the field of molecular biology and biotechnology. More specifically the present invention relates to means and methods for improving the selection of host cells with high expression levels.

BACKGROUND OF THE INVENTION

Bioactive proteins are produced in various host cells, ranging from bacteria and yeast to mammalian cells. Mammalian cells as host cell are preferred when the protein requires certain posttranslational modifications, such as glycosylation to function properly. In general, proteins produced in mammalian cells are expressed from a so-called 'transgene' encoding the protein of interest. To ensure that the right, protein-producing cell is selected, the transgene coding for the gene of interest is coupled to a second transgene encoding a selectable marker that most often is placed on the same vector. When a selection agent is added to the cell culture that has been transfected with the plasmid harboring the transgene, only those cells will survive that also harbor the selectable marker. A common problem is that the stringency of selection is often low. That implies that the cell has to make only very small amounts of selection protein in order to survive the toxic selection agent. In particular when the selection marker is an enzyme that neutralizes the toxic selection agent, these problems occur. One enzyme molecule can neutralize many molecules of selection agent in the course of time. Neomycin and the aminoglycoside phosphotransferase (neomycin) selection marker are an example of such combination. The limited requirement of selection marker protein has also implications for the expression levels of the transgenic protein. Low expression levels of selection marker can, for instance, be achieved by incorporation of only few copies of the plasmid. This, however, implies that also only few gene copies are available for the expression of the transgene protein, with low transgenic protein expression levels as result. Therefore, low expression levels of the protein of interest commonly accompany low selection stringency. This is obviously an unwanted side effect of low selection stringency.

An improvement in selection stringency can be seen when Zeocin and the Zeocin selection marker are used. The Zeocin selection protein is a selection marker protein that does not act as an enzyme. It stoichiometrically binds two Zeocin selection molecules and does not further process these molecules. Thus the available Zeocin selection proteins have only a limited capacity to neutralize a certain number of Zeocin molecules added to the culture medium. Therefore, the cell must produce much more Zeocin than for instance the Neomycin selection marker mRNA to produce enough selection protein to respectively neutralize Zeocin or Neomycin. When coupled to a gene of interest, this commonly also results in higher mRNA levels that encode the gene product of interest. These higher mRNA levels in turn signify higher expression levels of the gene product of interest.

Stably transfected clones can only be selected for the expression levels of the selection marker and not for the expression level of the gene of interest. Because of this, it is preferable that the expression of the gene of interest is directly linked to the expression level of the selection marker. There are multiple ways to physically couple the gene of interest to the gene encoding the selection marker gene. An IRES (Internal Ribosome Entry Site) sequence can be placed between the gene of interest and the gene encoding the selection marker. This creates a bicistronic mRNA from which both the gene product of interest and the selection protein are translated (Rees et al., 1996, Biotechniques 20: 102-110). When a high amount of selection protein, such as Zeocin selection protein is needed for the cell to survive, high levels of this bicistronic mRNA are needed. This in turn implies that high levels of mRNA encoding the gene product of interest are available for translation, and that relatively high expression levels of the gene product of interest are achieved. This principle provides higher selection stringency than when the gene of interest and the gene encoding the selection marker are not coupled through an IRES sequence. This procedure to select cell clones that express relatively high levels of the gene product of interest is an accepted and often employed method (see e.g. WO 03/106684, WO 2006/005718 and WO 2007/096399).

Other means to reach a higher level of selection stringency is to use selectable markers that harbor mutations that attenuate but do not completely destroy the activity of the selection marker. In order to neutralize a similar number of toxic selection molecules in the culture medium more mutated, more impaired selection protein has to be produced than the wild type selection protein. When coupled to the gene of interest through an IRES sequence, the higher impaired selection marker mRNA levels warrant that there is also more mRNA of the gene of interest available for translation. (see e.g. WO 01/32901 and WO 2006/048459)

In yet another example of high selection stringency systems the translation of the selection marker protein is severely impaired. In this example the modified selection marker gene is placed upstream of the gene of interest, not separated by an IRES sequence. In essence, the optimal ATG translation initiation codon of the selection marker is replaced by a less favorable translation initiation codon, such as GTG or TTG. In either case the translation machinery will not initiate translation on the GTG or even less so on the TTG, but will proceed scanning the mRNA. Provided there are no ATGs present in the selection gene (these have to be removed), the first ATG that will be encountered is the ATG of the gene of interest. In this configuration, high levels of this mRNA have to be produced to obtain enough selection protein, which in turn is needed for the cell to survive. However, these high mRNA levels also warrant that concomitantly high levels of the coupled gene of interest will be translated. Through this principle a system of high selection stringency has been created that results in a) only few colonies that survive the selection procedure and b) these colonies display relatively high expression levels of the gene product of interest. In particular a configuration that couples a TTG Zeocin selection marker to the gene of interest provides extremely high selection pressure. Collectively, these selection systems have been termed STAR-Select (WO 2006/048459 and WO 2007/096399).

The present invention discloses further improved means and methods for high stringency selection of mammalian cells to achieve high expression levels of gene products of interest.

DESCRIPTION OF THE INVENTION

Definitions

A "nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell. Common types of vectors may be derived from naturally occurring plasmids, phages and viruses. Vectors usually comprise further genetic elements to facilitate their use in molecular cloning, such as e.g. selectable markers, multiple cloning sites and replication origins functional in one or more host cells and the like.

The term "expression" is typically used to refer to the production of a specific nucleic acid product (preferably a specific RNA product) or a specific protein or proteins, in a cell. In the case of RNA products, it refers to the process of transcription. In the case of proteins, it refers to the processes of transcription, translation and optionally post-translational modifications. In the case of secreted proteins, it refers to the processes of transcription, translation, and optionally post-translational modification (e.g., glycosylation, disulfide bond formation, etc.), followed by secretion. In the case of multimeric proteins, it optionally includes assembly of the multimeric structure from the polypeptide monomers.

One type of nucleic acid construct is an "expression construct" or "expression cassette" or "expression vector". These terms refer to nucleotide sequences that are capable of effecting expression of a gene in host cells or host organisms compatible with such sequences. Expression constructs, expression cassettes or expression vectors typically include at least suitable transcription regulatory sequences and optionally, 3' transcription termination signals. Additional factors necessary or helpful in effecting expression may also be present, such as expression enhancer elements.

The term "monocistronic gene" is defined as a gene capable of providing a RNA molecule that encodes one gene product. A "multicistronic transcription unit", also referred to as multicistronic gene, is defined as a gene capable of providing an RNA molecule that encodes at least two gene products. The term "bicistronic gene", also referred to as "dicistronic gene", is defined as a gene capable of providing a RNA molecule that encodes two gene products. A bicistronic gene is therefore encompassed within the definition of a multicistronic gene.

The term peptide herein refers to any molecule comprising a chain of amino acids that are linked in peptide bonds. The term peptide thus includes oligopeptides, polypeptides and proteins, including multimeric proteins, without reference to a specific mode of action, size, 3-dimensional structure or origin. A "polypeptide" as used herein usually comprises at least five amino acids linked by peptide bonds. The terms "protein" or "polypeptide" are used interchangeably. A "fragment" or "portion" of a protein may thus still be referred to as a "protein". An "isolated protein" is used to refer to a protein which is no longer in its natural environment, for example in vitro or in a recombinant (fungal or plant) host cell. The term peptide also includes post-translational modifications of peptides, e.g. glycosylations, acetylations, phosphorylations, and the like.

A "gene product" of interest or a "transcription unit" as used in the present invention can comprise chromosomal DNA, cDNA, artificial DNA, combinations thereof, and the like. A "gene product of interest" can be any gene product, such as for example a protein, a RNAi, shRNA and the like. Non-limiting examples of a protein of interest are enzymes, immunoglobulin chains, therapeutic proteins like anti-cancer proteins or diagnostic proteins. Transcription units comprising several cistrons are transcribed as a single mRNA.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in eukaryotic (host) cells.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

As used herein, an "internal ribosome entry site" or "IRES" refers to an element that promotes direct internal ribosome entry to the translation initiation codon (also known as start codon) of a cistron (a protein encoding region), thereby leading to the cap-independent translation of the gene. See, e.g., Jackson R J, Howe 11 M T, Kaminski A (1990) Trends Biochem Sci 15 (12): 477-83) and Jackson R J and Kaminski, A. (1995) RNA 1 (10): 985-1000. The present invention encompasses the use of any cap-independent translation initiation sequence, in particular any IRES element that is able to promote direct internal ribosome entry to the initiation codon of a cistron. "Under translational control of an IRES" as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron.

As used herein, "cistron" refers to a segment of a polynucleotide sequence (DNA) that contains all the information for production of single polypeptide chain.

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty:10; Gap extension penalty: 0.05). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Nucleotide sequences of the invention may also be defined by their capability to hybridize with the specific nucleotide sequences disclosed herein or parts thereof, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

The adaptiveness of a nucleotide sequence encoding a gene product of interest to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51).

A preferred nucleic acid according to the invention is a nucleic acid construct, wherein the nucleotide sequence encoding the antigen-binding protein is operably linked to a promoter and optionally other regulatory elements such as e.g. terminators, enhancers, polyadenylation signals, signal sequences for secretion and the like. Such nucleic acid constructs are particularly useful for the production of the antigen-binding proteins of the invention using recombinant techniques in which a nucleotide sequence encoding the antigen-binding protein of interest is expressed in suitable host cells such as described in Ausubel et al., "Current Protocols in Molecular Biology", Greene Publishing and Wiley-Interscience, New York (1987) and in Sambrook and Russell (2001) "Molecular Cloning: A Laboratory Manual ($3^{rd}$ edition), Cold Spring Harbor Laboratory, Cold Spring Harbor Laboratory Press, New York). As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

DETAILED DESCRIPTION OF THE INVENTION

The present inventors found that particular nucleotide sequences that are present several kilobases upstream of (i.e. 5' to the) the retinoblastoma 1 (Rb1) coding sequence (e.g. SEQ ID NO's: 1-4) and parts thereof as further defined herein) and upstream of (i.e. 5' to the) the Cyclin-dependent kinase 4 inhibitor B coding sequence (also known as p15; CDKN2B; INK4B; MTS2; TP15) (e.g. SEQ ID NO: 8 and parts thereof as further defined below) when placed in an expression vector (comprising, operably linked, a promoter, a nucleotide sequence encoding a selectable marker functional in a eukaryotic host cell and optionally an open reading frame encoding a gene product of interest) are capable of increasing the number of colonies that are formed under selection conditions, preferably stringent selection conditions, as compared to the same expression vector without these particular sequences under stringent selection conditions. The nucleic acid sequences of the invention were not found to possess any promoter activity, nor are they enhancers, or do they influence transcription of endogenous Rb1 and p15 promoters in trans. The nucleic acid sequences of the invention also do not contain STAR activity. Rather, the nucleic acid sequences of the invention were found to be a source for intergenic transcription. The phenomenon of intergenic transcripts has been discovered in for instance the β-globin locus control locus (LCR) (Ashe et al (1997) Genes Dev. 11:2494-2509). For instance, in fission yeast, transcription of a non-coding RNA upstream of the fbp+ locus was shown to be necessary for expression of fbp+ (Hirota et al. (2008) Nature 456:130-134). Here, transcription through the fbp+ gene resulted in a progressively more open chromatin configuration. Intergenic transcription is often associated with promoter activity, however it is not yet clear whether it may be a cause or a consequence (Preker et al. (2008) Science 322:1851-1854). Without wishing to be bound to any theory, it is thought that intergenic transcripts (low-level and often very unstable intergenic transcripts) are involved in opening up a genomic locus or that the chromatin of the locus is kept open for transcription. Although it is not known whether intergenic transcription is causal for opening chromatin structure or the result of already open and transcribed loci, the phenomenon is considered an important epigenetic hallmark of open chromatin regions in which transcription takes place.

A nucleic acid construct according to the invention can be used to select eukaryotic cells, preferably plant cells or mammalian cells, that have high expression levels of a gene product of interest, by selecting for the expression of the selectable marker. Subsequently or simultaneously, one or more of the selected cell(s) can be identified, and further used for expression of high levels of the gene product of interest.

The present invention is based on an impaired efficiency of expression of a selectable marker. Expression of a selectable marker can be detected using routine methods known to the person skilled in the art, e.g. by determining the number of surviving colonies after a normal selection period. As is well known to the person skilled in the art there are a number of parameters that indicate the expression level of a selection marker polypeptide such as, the maximum concentration of selection agent to which cells are still resistant, number of surviving colonies at a given concentration, growth speed (doubling time) of the cells in the presence of selection agent, combinations of the above, and the like. By using the present invention, cells can be identified that have high levels of expression of the selectable marker.

In a first aspect, the present invention relates to a nucleic acid fragment comprising or consisting of: a) between 1,000 and 15,000 consecutive nucleotides of a genomic region that is present upstream of the translation initiation site of a vertebrate Rb1 gene; or, b) at least 1000, 1100, 1200, 1300, 1400, 1500, 1600, 1700, 1800, 1900, 2000, 2250, 2500, 2750, 3000 or 3500 consecutive nucleotides from a genomic region that is present from 10.5 to 7 kilobases upstream of the translation initiation site of a vertebrate p15 gene; wherein the fragment, when directly flanking an expression cassette having the nucleotide sequence of SEQ ID NO: 9 both up- and downstream of the expression cassette, produces at least 50, 75, 90, 100, 101, 110, 125 or 150% of number of colonies obtained with the same expression cassette when flanked with STARs 7 and 67 upstream of the expression cassette and STAR 7 downstream of the expression cassette (SEQ ID NO: 10), when tested under the conditions of Example 1. Preferably the fragment has at least 80, 85, 87, 90, 91, 92, 93, 94, 95, 96, 97, 98 or 99% nucleotide sequence identity over its entire length with at least 1000, 1500, 2000, 3000, 4000, 5000, 6000, or all of the consecutive nucleotides of at least one of SEQ ID NO's: 1-4 or 8. In a preferred embodiment the nucleic acid fragment is a fragment which has at least 80, 85, 87, 90, 91, 92, 93, 94, 95, 96, 97, 98 or 99% nucleotide sequence identity over its entire length with at least 1000, 1100, 1200, 1300, 1400, 1500, 1600, 1700, 1800, 1900, 2000, 2250, 2500, 2750, 3000 or 3500 consecutive nucleotides from SEQ ID NO's: 1-4 or 8.

The nucleic acid fragment preferably is an isolated nucleic acid fragment, which is understood to mean a fragment isolated or purified from its natural environment. Preferably, the nucleic acid fragment is from a mammalian genome, more preferably from a primate or rodent genome, and most preferably the nucleic acid fragment is from a human, mouse, rat, hamster, bovine, chicken, dog, cavia, pig or rabbit genome. Preferred nucleic acid fragment are from SEQ ID NO's: 1 or 8 (human), SEQ ID NO: 2 (mouse), SEQ ID NO: 3 (bovine) or SEQ ID NO: 4 (cavia).

In a further preferred embodiment the nucleic acid fragment is selected from the group consisting of fragments having at least 80, 85, 87, 90, 91, 92, 93, 94, 95, 96, 97, 98 or 99% nucleotide sequence identity over their entire length with a fragment comprising or consisting of nucleotide residues 1-1019, 1-1482, 1-2018, 1-3498, 479-2018 or 479-1482 of Rb1E (SEQ ID NO: 5), nucleotide residues 1-2448, 1-3424 or 2425-3424 of Rb1F (SEQ ID NO: 6), nucleotide residues 1-3064, 1-2500 or 1-2000 of Rb1E/Rb1F (SEQ ID NO: 7) and nucleotide residues 1-1500, 822-3352 or 1-3352 of SEQ ID NO: 8. More preferably, the nucleic acid fragment is selected from the group consisting of fragments having at least 80, 85, 87, 90, 91, 92, 93, 94, 95, 96, 97, 98 or 99% nucleotide sequence identity over their entire length with a fragment comprising or consisting of nucleotide residues 1-3498, 1-2018 or 1-1482 of SEQ ID NO: 5, nucleotide residues 1-3424 or 2425-3424 of SEQ ID NO: 6, nucleotide residues 1-2500 or 1-3064 of SEQ ID NO: 8 and nucleotide residues 822-3352 or 1-3352 of SEQ ID NO: 8. Again more preferably, the nucleic acid fragment is selected from the group consisting of fragments having at least 80, 85, 87, 90, 91, 92, 93, 94, 95, 96, 97, 98 or 99% nucleotide sequence identity over their entire length with a fragment comprising or consisting of nucleotide residues 1-2000 of SEQ ID NO: 5; nucleotide residues 2500-3424 of SEQ ID NO: 6; nucleotide residues 1-3064 of SEQ ID NO: 7; and nucleotide residues 850-3352 of SEQ ID NO: 8. Most preferably, the nucleic acid sequence is selected from the group consisting of fragments having at least 80, 85, 87, 90, 91, 92, 93, 94, 95, 96, 97, 98 or 99% nucleotide sequence identity over their entire length with a fragment comprising or consisting of nucleotide residues SEQ ID NO: 7 or residues 850-3352 of SEQ ID NO: 8 It is understood that in the above definitions reference is made to the consecutive nucleotide residues of the indicated SEQ ID NO's.

In a second aspect the invention relates to a nucleic acid construct comprising a nucleic acid fragment as defined above, wherein the fragment is linked to at least one nucleotide that does not naturally occur immediately adjacent to the fragment in the genome from which the fragment is derived. Preferably the nucleic acid construct comprises more than one non-naturally occurring nucleotide attached to the fragment, such as e.g. a stretch of nucleotides comprising one or more restriction sites or adapter sequences that are complementary to PCR primers.

More preferably, the nucleic acid construct comprises a nucleic acid fragment as defined above, wherein the fragment is linked to an expression cassette. The expression cassette preferably comprises at least a promoter operably linked to a nucleotide sequence encoding a gene product of interest. The promoter may be a promoter as defined below. The expression cassette may further comprise a nucleotide sequence encoding a selectable marker functional in a eukaryotic host cell e.g. as described below.

A nucleic acid fragment according to the invention functions 'in cis'. Hence, it is preferred that in the nucleic acid construct, a nucleic acid fragment of the invention is present within 5 kb, more preferably within 2 kb, still more preferably within 1 kb, most preferably within 500 bp from the expression cassette or more preferably from the most 5' promoter in the expression cassette. If a nucleic acid fragment of the invention is present downstream of the expression cassette in the construct, the nucleic acid fragment of the invention is present within 5 kb, more preferably within 2 kb, still more preferably within 1 kb, most preferably within 500 bp from the expression cassette or more preferably from the most 3' transcription terminator sequence and/or polyadenylation site in the expression cassette. Thus, a nucleic acid construct may comprise a nucleic acid fragment of the invention either downstream or upstream of an expression cassette. If in the nucleic acid construct sequence, the nucleic acid fragment of the invention is located downstream of the expression cassette, it is preferred that the nucleic acid fragment is a nucleic acid fragment from upstream of Rb1 as defined above, since these fragment yield more colonies at this position and under stringent conditions as compared to the sequences as defined above that are based on SEQ ID NO: 8, i.e. p15 upstream sequences.

However, in a preferred embodiment a nucleic acid construct comprises a nucleic acid fragment according to the invention both upstream and downstream of the expression cassette. In the nucleic acid construct the nucleic acid fragments according to the invention that are present up- and downstream of the expression cassette may be independently selected from the nucleic acid fragments as defined above. Thus, in the nucleic acid construct, the nucleic acid fragment upstream of the expression cassette may be different from the nucleic acid fragment downstream of the expression cassette. Alternatively, in the nucleic acid construct, the nucleic acid fragments up- and downstream of the expression cassette may be (essentially) identical. Preferably, the configuration of the nucleic acid construct is such that, when in linear form and going from 5' to 3' end, the nucleic acid construct comprises the following sequence elements in the following order: a first nucleic acid fragment according to the invention, an expression cassette and a second nucleic acid fragment according to the invention, whereby the expression cassette comprises a transcription unit comprising a promoter operably linked to nucleotide sequence encoding a gene product of interest and optionally a selectable marker. The advantage of an expression cassette being flanked by two nucleic acid fragments of the invention is that a higher number of colonies is obtained when cultured in cells under stringent selection conditions and that expression of the selectable marker and thus also of the gene product of interest is higher as compared to a nucleic acid construct with only one nucleic acid fragment according to the invention.

A "expression cassette" as used herein is a nucleotide sequence comprising at least a promoter functionally linked to a nucleotide sequence encoding a gene product of interest, of which expression is desired. Preferably, the expression cassette further contains transcription termination and polyadenylation sequences. Other regulatory sequences such as enhancers may also be included in the expression cassette. In addition to the nucleotide sequence encoding a gene product of interest, the expression cassette preferably also comprises a nucleotide sequence encoding a selectable marker for selection of host cells comprising the expression cassette. In a preferred embodiment, the nucleotide sequence encoding the gene product of interest and the nucleotide sequence encoding a selectable marker are part of the same (multicistronic) transcription unit in the expression cassette. Hence, the invention provides for an expression cassette preferably comprising in a 5' to 3' direction, and operably linked: a) 5'—a promoter—a nucleotide sequence encoding a selectable marker—an open reading frame encoding a gene product of interest—optionally, transcription termination and/or polyadenylation sequences—3', or b) 5'—a promoter—an open reading frame encoding a gene product of interest—a nucleotide sequence encoding a selectable marker—optionally, transcription termination and/or polyadenylation sequences—3'. The promoter, as well as the other regulatory sequences, must be capable of functioning in the eukaryotic host cell in question, i.e. they must be capable of driving transcription of the gene product of interest and the selectable marker. The promoter is thus operably linked to the transcription unit(s) comprising the selectable marker and the open reading frame encoding a gene product of interest. The expression cassette may optionally further contain other elements known in the art, e.g. splice sites to comprise introns, and the like. In some embodiments, an intron is present behind the promoter and before the sequence encoding an open reading frame.

In other embodiments, an IRES may be present in the transcription unit that contains the selectable marker coding sequence and the sequence encoding the gene product of interest, which IRES may be present in between the open reading frames of the selectable marker and the gene product of interest. Internal ribosome binding site (IRES) elements are known from viral and mammalian genes (Martinez-Salas, 1999, Curr Opin Biotechnol 10: 458-464), and have also been identified in screens of small synthetic oligonucleotides (Venkatesan & Dasgupta, 2001 Mol Cell Biol 21: 2826-2837). The IRES from the encephalomyocarditis virus has been analyzed in detail (Mizuguchi et al., 2000, Mol Ther 1: 376-382). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas, 1999, supra). Thus, the invention provides an expression cassette preferably comprising in a 5' to 3' direction: 5'—a promoter—an open reading frame encoding a gene product of interest—an IRES—a selectable marker—optionally, transcription termination and/or polyadenylation sequences—3' or 5'-promoter—a selectable marker—an IRES—an open reading frame encoding a gene product of interest—optionally, transcription termination and/or polyadenylation sequences—3'. A promoter to be applied in the expression cassettes comprised in the nucleic acid constructs of the invention preferably is functional in a eukaryotic host cell, more preferably, the promoter is functional in a plant or animal host cell, still more preferably the promoter is functional in a vertebrate host cell and most preferably in a mammalian host cell, for initiating transcription of the transcription unit. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000, Mol. Biotechnol 16: 151-160). According to the present invention, strong promoters that give high transcription levels in the eukaryotic cells of choice are preferred. Some well-known and frequently used strong promoters for expression in eukaryotic cells comprise promoters derived from viruses, such as adenovirus, e.g. the ElA promoter, promoters derived from cytomegalovirus (CMV), such as the CMV immediate early (IE) promoter (referred to herein as the CMV promoter) (obtainable e.g. from pcDNA, Invitrogen), promoters derived from Simian Virus 40 (SV40) (Das et al, 1985, Prog Nucleic Acid Res Mol Biol. 32: 217-36), and the like. Suitable strong promoters can also be derived from eukaryotic cells, such as methallothionein (MT) promoters, an elongation factor (EF-1α) promoter, an ubiquitin C or UB6 promoter (Gill et al., 2001, Gene Therapy 8: 1539-1546; Schorpp et al, 1996, Nucleic Acids Res 24: 1787-8), an actin promoter such as a β-actin promoter, e.g. a hamster or human β-actin promoter (SEQ ID NO: 11), an immunoglobulin promoter, a heat shock promoter and the like. Testing for promoter function and strength of a promoter is a matter of routine for a person skilled in the art, and in general may for instance encompass cloning a reporter gene such as lacZ, luciferase, GFP, etc. behind the promoter sequence, and test for expression of the reporter gene. Of course, promoters may be altered by deletion, addition, mutation of sequences therein, and tested for functionality, to find new, attenuated, or improved promoter sequences. Preferred promoters for use in the present invention are a human β-actin promoter, a CMV promoter, an SV40 promoter, an ubiquitin C promoter or an EF1-alpha promoter.

An open reading frame is herein understood as a nucleotide sequence comprising in a 5' to 3' direction 1) a translation initiation codon, 2) one or more codons coding for a gene product of interest, preferably a protein, and 3) a translation stop codon, whereby it is understood that 1), 2) and 3) are operably linked in frame. The open reading frame will thus consist of a multiple of 3 nucleotides (triplets).

A gene product of interest according to the invention can be any gene product, e.g. a protein. A gene product of interest may be a monomeric protein or a (part of a) multimeric protein. A multimeric protein comprises at least two polypeptide chains. Non-limiting examples of a protein of interest according to the invention are enzymes, hormones, immunoglobulins or chains or fragments thereof, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

A gene product of interest may be from any source, and in certain embodiments is a mammalian protein, an artificial protein (e.g. a fusion protein or mutated protein), and preferably is a human protein.

In a preferred embodiment, a nucleotide sequence encoding a gene product of interest is codon optimized for the host cell in which the peptide of interest is to be expressed, using the codon adaptation index of the host cell. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). Preferably, a nucleotide sequence encoding a gene product of interest has a CAI of at least 0.5, 0.6, 0.7, 0.8, 0.9 or 0.95.

In one embodiment, a nucleic acid construct of the present invention is used when the ultimate goal is not the production of a polypeptide of interest, but rather an RNA molecule, e.g. for producing increased quantities of RNA from an expression cassette, which may be used for purposes of regulating other genes (e.g. RNAi, antisense RNA), gene therapy, in vitro protein production, etc.

For the production of multimeric proteins, two or more nucleic acid constructs according to the invention can be used. For example, both expression cassettes can be multicistronic nucleic acid constructs, each coding for a different selectable marker protein, so that selection for both expression cassettes is possible. This embodiment is advantageous, e.g. for the expression of the heavy and light chain of immunoglobulins such as antibodies. It will be clear that both nucleic acid constructs may be placed on one nucleic acid molecule or both may be present on a separate nucleic acid molecule, before they are introduced into host cells. An advantage of placing them on one nucleic acid molecule is that the two nucleic acid constructs are present in a single predetermined ratio (e.g. 1:1) when introduced into host cells. On the other hand, when present on two different nucleic acid molecules, this allows the possibility to vary the molar ratio of the two nucleic acid constructs when introducing them into host cells, which may be an advantage if the preferred molar ratio is different from 1:1 or when it is unknown beforehand what is the preferred molar ratio, so that variation thereof and empirically finding the optimum can easily be performed by the skilled person. According to the invention, preferably at least one of the nucleic acid constructs, but more preferably each of them, comprises a at least one but preferably two nucleic acid fragments according to the invention.

In another embodiment, the different subunits or parts of a multimeric protein are present in a single expression construct. Useful configurations of anti-repressors combined with expression constructs have been described in WO 2006/048459 (e.g. page 40), incorporated by reference herein.

In a preferred embodiment, the gene product of interest is a coagulation factor such as Factor VIII or factor VII, interferons and interleukins, such as human interferon-gamma or therapeutic, anti-cancer monoclonal antibodies such as Herceptin (anti-EGF receptor) or Avastin (anti-vascular endothelial growth factor (VEGF)) or EPO.

A nucleic acid construct of the invention can be present in the form of double stranded DNA, having with respect to the selectable marker and the open reading frame encoding a gene product of interest a coding strand and a non-coding strand, the coding strand being the strand with the same sequence as the translated RNA, except for the presence of T instead of U. Hence, an AUG startcodon is coded for in the coding strand by an ATG sequence, and the strand containing this ATG sequence corresponding to the AUG startcodon in the RNA is referred to as the coding strand of the DNA. It will be clear to the skilled person that startcodons or translation initiation sequences are in fact present in an RNA molecule, but that these can be considered equally embodied in a DNA molecule coding for such an RNA molecule; hence, wherever the present invention refers to a startcodon or translation initiation sequence, the corresponding DNA molecule having the same sequence as the RNA sequence but for the presence of a T instead of a U in the coding strand of said DNA molecule is meant to be included, and vice versa, except where explicitly specified otherwise. In other words, a startcodon is for instance an AUG sequence in RNA, but the corresponding ATG sequence in the coding strand of the DNA is referred to as startcodon as well in the present invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

A selectable marker to be applied in the expression cassettes comprised in the nucleic acid constructs of the invention preferably is functional in a eukaryotic host cell, more preferably, the marker is functional in a plant or animal host cell, still more preferably in a vertebrate host cell and most preferably in a mammalian host cell.

The term "selectable marker" is a term familiar to one of ordinary skill in the art and is used herein to describe any genetic entity which, when expressed, can be used to select for a cell or cells containing (and/or expressing) the selectable marker. Selectable markers may be dominant or recessive or bidirectional. The selectable marker may be a gene coding for a product which confers to a cell expressing the gene resistance to a selection agent such as e.g. an antibiotic or herbicide. The selectable marker may e.g. encode a selection protein that is able to neutralize or inactivate a toxic selection agent and protects the host cell from the agent's lethal or growth-inhibitory effects. Other selectable markers complement a growth-inhibitory deficiency in the cell under certain conditions. Examples of such genes include a gene which confers prototrophy to an auxotrophic strain. The term "reporter" is mainly used to refer to visible markers, such as green fluorescent protein (GFP), eGFP, luciferase, GUS and the like, as well as nptII markers and the like. Such reporters can be used for selecting cells expressing the visible marker by actively sorting cells expressing the marker from cells that do not, e.g. using a fluorescence activated cell sorter (FACS) for selecting cells that express a fluorescent marker protein. Preferably, the selectable marker according to the invention provides resistance against lethal and/or growth-inhibitory effects of a selection agent.

A nucleotide sequence encoding a selectable marker for use in the present invention encodes a protein that can be used for selection of eukaryotic host cells, e.g. because upon expression of the protein in the host cell it provides a growth advantage to the host cells expressing the selectable marker protein, as compared to host that do not. A preferred nucleotide sequence encoding a selectable marker provides resistance to a selection agent (e.g. an antibiotic) upon expression of the encoded selectable marker protein in the host cell, which selection agent causes lethality and/or growth inhibition of host cells not expressing the selectable marker protein. The selectable marker according to the invention must thus be functional in a eukaryotic host cell, and hence being capable of being selected for in eukaryotic host cells. Any selectable marker polypeptide fulfilling this criterion can in principle be used according to the present invention. Such selectable markers are well known in the art and routinely used when eukaryotic host cell clones are to be obtained, and several examples are provided herein.

For convenience and as generally accepted by the skilled person, in many publications as well as herein, often the gene encoding for the selectable marker and the selectable marker that causes resistance to a selection agent is referred to as the 'selectable agent (resistance) gene' or 'selection agent (resistance) protein', respectively, although the official names may be different, e.g. the gene coding for the protein conferring resistance to neomycin (as well as to G418 and kanamycin) is often referred to as neomycin (resistance) (or $neo^r$) gene, while the official name is aminoglycoside 3'-phosphotransferase gene.

In a preferred embodiment of the invention, the selectable marker provides resistance against lethal or growth-inhibitory effects of a selection agent selected from the group consisting of the bleomycin family of antibiotics, puromycin, blasticidin, hygromycin, an aminoglycoside antibiotic, methotrexate, and methionine sulphoximine.

A nucleotide sequence encoding a selectable marker providing resistance to bleomycin family of antibiotics is e.g. a nucleotide sequence encoding a wild-type "ble" gene, including but not limited to Sh ble, Tn5 ble and Sa ble or a variant thereof. An example thereof is depicted in SEQ ID NO: 14. In general the gene products encoded by the ble genes confer to their host resistance to the copper-chelating glycopeptide antibiotics of the bleomycin family, which are DNA-cleaving glycopeptides. Examples of antibiotics of the bleomycin family for use as selection agents in accordance with the present invention include but are not limited to bleomycin, phleomycin, tallysomycin, pepleomycin and Zeocin™. Zeocin is particularly advantageous as a selection agent, because the zeocin-resistance protein (zeocin-R) acts by binding the drug and thereby rendering it harmless. Therefore it is easy to titrate the amount of drug that kills cells with low levels of zeocin-R expression, while allowing the high-expressors to survive. Most if not all other antibiotic-resistance selectable markers in common use are enzymes, and thus act catalytically (i.e. not in a given, e.g. 1:1, stoichiometry with the selection agent). Hence, the antibiotic zeocin is a preferred selectable marker.

A nucleotide sequence encoding a selectable marker providing resistance to the aminoglycoside antibiotic is e.g. a nucleotide sequence encoding a wild-type aminoglycoside 3'-phosphotransferase or a variant thereof. An aminoglycoside according to the present invention are the commonly known aminoglycoside antibiotics (Mingeot-Leclercq, M. et al., 1999, Chemother. 43: 727-737) comprising at least one amino-pyranose or amino-furanose moiety linked via a glycosidic bond to the other half of the molecule. Their antibiotic effect is based on inhibition of protein synthesis. Examples of aminoglycoside antibiotics for use as selection agents in accordance with the present invention include but are not limited Kanamycin, Streptomycin, Gentamicin, Tobramycin, G418 (Geneticin), Neomycin B (Framycetin), Sisomicin, Amikacin, Isepamicin and the like.

Other examples of selectable markers which can be used in the invention are DHFR, cystathionine gamma-lyase and glutamine synthetase (GS) genes. A potential advantage of the use of these types of metabolic enzymes as selectable marker polypeptides is that they can be used to keep the host cells under continuous selection, which may advantageous under certain circumstances.

The DHFR gene, which can be selected for by methotrexate, especially by increasing the concentration of methotrexate cells can be selected for increased copy numbers of the DHFR gene. The DHFR gene may also be used to complement a DHFR-deficiency, e.g. in CHO cells that have a $DHFR^{-}$ phenotype, in a culture medium with folate and lacking glycine, hypoxanthine and thymidine. If the selectable marker is DHFR, the host cell in advantageous embodiments is cultured in a culture medium that contains folate and which culture medium is essentially devoid of hypoxanthine and thymidine, and preferably also of glycine. In general, with “culture medium is essentially devoid” is meant herein that the culture medium has insufficient of the indicated component present to sustain growth of the cells in the culture medium, so that a good selection is possible when the genetic information for the indicated enzyme is expressed in the cells and the indicated precursor component is present in the culture medium. Preferably, the indicated component is absent from the culture medium. A culture medium lacking the indicated component can be prepared according to standard methods by the skilled person or can be obtained from commercial media suppliers.

Selection for a glutamine synthetase (GS) gene, e.g. a wild-type human or mouse glutamine synthetase gene, is possible in cells having insufficient GS (e.g. NS-O cells) by culturing in media without glutamine, or alternatively in cells having sufficient GS (e.g. CHO cells) by adding an inhibitor of GS, methionine sulphoximine (MSX).

Cystathionine gamma-lyase (EC 4.4.1.1) is an enzyme that is crucial for the synthesis of the amino acid L-cysteine. CHO cells are natural auxotrophs for the conversion of cysthathionine to cysteine. Therefore, the cystathionine gamma-lyase (cys-lyase) gene, e.g. from mouse or human, can be used for selection of cells by complementation by culturing cells in media without L-cysteine and L-cystine. Selection on the basis of the cys-lyase marker may require the non-toxic precursor L-cystathionine to be present in the culture medium. The use of cys-lyase as selectable marker in some vertebrate cell lines may first require inactivation (knock-out) of the endogenous cystathionine gamma-lyase genes.

Further selectable markers and their selection agents that could be used in the context of the present invention, are for instance described in Table 1 of U.S. Pat. No. 5,561,053, incorporated by reference herein; see also Kaufman, Methods in Enzymology, 185:537-566 (1990), for a review of these selectable markers and their selection agents.

In a preferred embodiment, the expression cassette in a nucleic acid construct of the present invention, comprises a selectable marker that is a stringent selection marker. A stringent selection marker is herein understood as a selection marker that requires to be transcribed (and/or expressed) at high level in the host cell expressing the marker for that host cell to be selected, i.e. for that host cell to survive the applied selection. In the context of the present invention, the stringency of the selectable marker is preferably increased by at least one of a) reducing the translation (initiation) efficiency of the selectable marker and b) reducing the activity and/or efficacy of the selectable marker polypeptide. Therefore, the expression cassette in a nucleic acid construct of the present invention, preferably comprises a nucleotide sequence encoding the selectable marker which nucleotide sequence is a least one of:

a) a nucleotide sequence having a mutation in the startcodon that decreases the translation initiation efficiency of the selectable marker polypeptide in a eukaryotic host cell;

b) a nucleotide sequence that is part of a multicistronic transcription unit comprising i) the nucleotide sequence encoding the selectable marker; and, ii) a functional open reading frame comprising in a 5' to 3' direction a translation initiation codon, at least one amino acid codon and a translation stop codon; wherein the stop codon of functional open reading frame is present between 0 and 250 nucleotides upstream of the separate translation initiation codon of the nucleotide sequence encoding the selectable marker, and wherein the sequence separating the stop codon of functional open reading frame and the separate translation initiation codon of the nucleotide sequence encoding the selectable marker is devoid of translation initiation codons; and, c) a nucleotide sequence encoding a selectable marker polypeptide comprising a mutation encoding at least one amino acid change that reduces the activity of the selectable marker polypeptide compared to its wild-type counterpart.

Nucleotide sequences encoding a selectable marker having a mutation in the (translation) startcodon (a sub-optimal non-AUG initiation codon) that decreases the translation initiation efficiency of the selectable marker polypeptide in a eukaryotic host cell are known in the art (see e.g. WO 2007/096399). A non-ATG (non-AUG) startcodon is herein understood as a translation initiation codon comprising a mutation in the startcodon that decreases the translation initiation efficiency of the selectable marker polypeptide in a eukaryotic host cell. Examples of non-ATG start codons that may be used for the coding sequence of the selectable marker in the invention include e.g. GTG, TTG, CTG, ATT, and ACG. In a preferred embodiment, the ATG startcodon is mutated into a GTG startcodon. More preferably, the ATG startcodon is mutated to a TTG startcodon, which provides even lower expression levels of the selectable marker polypeptide than with the GTG startcodon. When using a non-ATG startcodon, it is preferred that the non-ATG start codon is present in an optimal context for translation initiation codon, such as a Kozak consensus sequence as herein defined below. When applying a non-ATG startcodon for the selectable marker the nucleotide sequence coding for the selectable marker can be mutated to be devoid of internal ATG codons, particularly devoid of internal ATG codons that are in frame with the non-ATG start codon. This is preferred in constructs wherein the selectable marker is upstream of a nucleotide sequence coding for a gene product of interest without using an IRES in between the sequences coding for the gene product of interest and the marker. WO 2006/048459 discloses how to bring this about (e.g. by substitution, insertion or deletion, preferably by substitution) and how to test the resulting selectable marker polypeptides for functionality.

The second option for reducing the efficiency of translation initiation in b) above, uses a (short) functional open reading frame ($pp^x$; wherein $pp^x$ is a petit peptide of x amino acid residues) directly preceding the translation initiation codon of the selectable marker. The length of the functional open reading frame ($pp^x$) can be varied in order to fine tune low levels of translational efficiency of the selectable marker polypeptide, so that the exact required level of stringency of selection is obtained. Thus, the functional open reading frame may thus encode at least 1, 2, 3, 4, 5, 6, 7, 8, 9, 10, 11, 12, 13, 14, 15, 20, 25, 30, 35, 40, 45, 50, 55, 60, 70, 80 or 90 amino acid residues and preferably encodes no more than 200, 180, 160, 150, 140, 130, 120, 110, 100, 99, 98, 97, 96, 95, 94, 93, 92, 91, or 90 amino acid residues with a startcodon at the 5' and a stopcodon at the 3' end. By thus varying the length of the functional open reading frame ($pp^x$) that immediately precedes the sequence encoding the selectable marker in the transcript, a near continuous range of translational efficiencies of the selectable marker is provided. The functional open reading frame ($pp^x$) may be located immediately upstream of the separate startcodon of the selectable marker, in which case the stopcodon of the functional open reading frame is immediately adjacent to the start codon of the sequence coding for the selectable marker. Alternatively the stopcodon of the upstream functional open reading frame ($pp^x$) and the startcodon of the sequence coding for the selectable marker may be separated by 1, 2, 3, 4, 5, 6, 7, 8, 9, 10, 12, 14, 16, 18, 19, 20, 25, 30, 35, 40, 45, 50, 60, 70, 80, 90, 100, 120, 140, 160 180, 200, 250 or more nucleotides. Variation of the length of the spacer sequence separating the stopcodon of the upstream functional open reading frame ($pp^x$) and the startcodon of the sequence coding for the selectable marker adds a further level of fine tuning of the translational efficiency of the selectable marker. The spacer sequence separating the stop codon of functional open reading frame ($pp^x$) and the separate translation initiation codon of the nucleotide sequence encoding the selectable marker is devoid of translation initiation codons. Preferably therefore, the spacer sequence lacks ATG codons. More preferably, the spacer sequence also lacks suboptimal non-ATG codons such as GTG, TTG, CTG, ATT, and ACG (see below) embedded in a Kozak sequence (see below). Most preferably, the spacer sequence is devoid of any of the ATG, GTG, TTG, CTG, ATT, and ACG codons. In a further preferred embodiment, the spacer sequence separating the stop codon of functional open reading frame ($pp^x$) and the separate translation initiation codon of the nucleotide sequence encoding the selectable marker is devoid of stopcodons, i.e. lacks TAA, TAG and TGA codons.

In a preferred embodiment, at least one of the translation initiation codons of the nucleotide sequence encoding the selectable marker and of the functional open reading frame ($pp^x$) is an ATG codon. More preferably at least the initiation codon of the nucleotide sequence encoding the functional open reading (ppX) is an ATG codon, in which case the initiation codon of the nucleotide sequence encoding the selectable marker can be a non-ATG startcodon (also known as suboptimal or less-favorable translation initiation codon), in order to allow for even more stringent selection (see above). Most preferably both the translation initiation codons of the nucleotide sequence encoding the selectable marker and the functional open reading frame ($pp^x$) are ATG codons. However, the invention does not exclude that the initiation codon of the nucleotide sequence encoding the functional open reading ($pp^x$) is a non-ATG startcodon.

In one embodiment, at least one of the initiation codons of the nucleotide sequence encoding the selectable marker and the functional open reading frame ($pp^x$) is embedded in a Kozak consensus sequence. The Kozak consensus sequence (for vertebrate host cells) is herein defined as ANN(AUG)N (SEQ ID NO: 11) and GNN(AUG)G (SEQ ID NO: 12), wherein (AUG) stands for the initiation codon of the relevant coding sequence. Preferably, both N's preceding the (AUG) are C's. A more preferred Kozak consensus sequence is GCCRCC(AUG)G (SEQ ID NO: 13), wherein R is a purine. In a further preferred embodiment, the Kozak consensus sequence may be preceded by yet another GCC triplet.

A preferred selectable markers preceded by a functional open reading frame ($pp^x$) is e.g. $pp^{90}$ZEO (a $pp^x$ open reading frame that encodes 90 amino acids preceding the zeomycin resistance protein; the $pp^{90}$ coding sequence is given in SEQ ID NO: 15).

In one embodiment, alternatively or in combination with a decreased translation initiation efficiency of a) or b) above, it can be beneficial to also provide for decreased translation elongation efficiency of the selectable marker polypeptide. This may be achieved by e.g. mutating the sequence coding the selectable marker polypeptide so as to decrease the adaptation of the codon usage to the host cell in question. This again provides a further level of controlling the stringency of selection of the nucleic acid constructs of the invention. Thus, a nucleotide sequence encoding a selectable marker protein, is preferably adapted to a codon usage to that is suboptimal in host cell in question. An codon adapted nucleotide sequence in accordance with the present invention preferably has a CAI of no more than 0.7, 0.6, 0.5, 0.4, 0.3 or 0.2 (see above for definition of CAI).

In one embodiment, alternatively or in combination with the embodiments of selectable markers with a decreased translation initiation efficiency as described in a) or b) above, mutants or derivatives of selectable markers are suitably used according to the invention, and are therefore included within the scope of the term 'selectable marker', as long as the selectable marker is still functional. Mutants or derivatives of a selectable marker preferably have reduced activity of the selectable marker compared to its wild-type counterpart allowing a further level of control in fine tuning of the stringency of selection of the nucleic acid constructs of the invention. Alternatively or in combination with one or more other embodiments, in a preferred embodiment, the nucleotide sequence encoding the selectable marker encodes a selectable marker polypeptide comprising one or more mutations that (collectively) reduce the activity of the selectable marker polypeptide compared to its wild-type counterpart. The activity of the mutated selectable marker polypeptide can be or more than 90, 80, 70, 60, 50, 40, 30, 20, 10, 5 or 1% to its wild-type counterpart.

As non-limiting examples, proline at position 9 in the zeocin resistance polypeptide may be mutated, e.g. to Thr or Phe (see e.g. example 14 of WO 2006/048459, incorporated by reference herein), and for the neomycin resistance polypeptide, amino acid residue 182 or 261 or both may further be mutated (see e.g. WO 01/32901). A preferred selectable marker polypeptide with reduced activity is a zeocin resistance polypeptide having the amino acids sequence of SEQ ID NO: 14 wherein the glutamic acid at position 21 is changed into glycine, and the alanine at position 76 is changed into threonine ($Zeo^{EPP5}$).

A particularly preferred stringent selectable marker is $pp^8ZEO^{EPP5}$, which combines a $pp^x$ open reading frame of 8 amino acids and the $Zeo^{EPP5}$ zeocin resistance protein with reduced activity. The sequence of $pp^8ZEO^{EPP5}$ is depicted in SEQ ID NO: 16.

A nucleic acid construct according to the invention is preferably comprised in a plasmid or an expression construct can be a plasmid. A plasmid can easily be manipulated by methods well known to the person skilled in the art, and can for instance be designed for being capable of replication in prokaryotic and/or eukaryotic cells. Alternatively, a nucleic acid construct may be a vector. Many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art, and several aspects hereof have been described in WO 2006/048459 (e.g. pages 30-31), incorporated by reference herein.

In one embodiment, a nucleic acid construct according to the invention comprises an additional selection marker, e.g. a DHFR metabolic selection marker as described supra. An advantage of such a nucleic acid construct is that selection of a host cell with high expression can be established by use of a selection marker operably linked with an IRES, e.g. zeocin, neomycin, etc, whereas after the selection of a host cell with high expression the antibiotic selection is discontinued and either continuous or intermittent selection is done using the additional selection marker. The multicistronic transcription units in this embodiment are at least tricistronic.

It is preferred to use separate nucleic acid constructs for the expression of different gene products of interest, also when these form part of a multimeric protein (see e.g. example 13 of WO 2006/048459, incorporated by reference herein): the heavy and light chain of an antibody each are encoded by a separate transcription unit according to the invention. When two transcription units of the invention are to be selected for according to the invention in a single host cell, each one preferably contains the coding sequence for a different selectable marker, to allow selection for both transcription units. Of course, both transcription units may be present on a single nucleic acid molecule or alternatively each one may be present on a separate nucleic acid molecule.

In a third aspect, the present invention relates to an expression vector or an expression construct comprising a nucleic acid construct according to the invention.

In a fourth aspect, the present invention relates to a host cell, preferably a eukaryotic host cell, comprising a nucleic acid construct according to the invention or an expression vector according to the invention.

The terms "cell" or "host cell" and "cell line" or "host cell line" are respectively defined as a cell and homogeneous populations thereof that can be maintained in cell culture by methods known in the art, and that have the ability to express heterologous or homologous proteins. The host is an eukaryotic host cell such as a cell of fungal, plant, or animal origin. Preferably the host cell is an animal cell of insect or vertebrate origin. More preferably the host cell is a mammalian cell. Preferably, the host cell is a cell of a cell line. Several exemplary host cells that can be used have been described in WO 2006/048459 (e.g. page 41-42), incorporated by reference herein, and such cells include for instance mammalian cells, including but not limited to CHO cells, e.g. CHO-K1, CHO-S, CHO-DG44, CHO-DG44-S, CHO-DUKXBI 1, including CHO cells having a $dhfr^-$ phenotype, as well as myeloma cells (e.g. Sp2/0, NSO), HEK 293 cells, HEK 294 cells, and PER.C6 cells. Other examples of host cells that can be used are a U-2 OS osteosarcoma, HuNS-1 myeloma, WERI-Rb-1 retinoblastoma, BHK, Vero, non-secreting mouse myeloma Sp2/0-Ag 14, non-secreting mouse myeloma NSO and NCI-H295R adrenal gland carcinoma cell line.

Such eukaryotic host cells can express desired gene products, and are often used for that purpose. They can be obtained by introduction of a nucleic acid construct of the invention, preferably in the form of an expression construct, an expression cassette or an expression vector according to the invention, into the cells. Preferably, the nucleic acid construct is integrated in the genome of the host cell, which can be in different positions in various host cells, and selection will provide for a clone where the transgene is integrated in a suitable position, leading to a host cell clone with desired properties in terms of expression levels, stability, growth characteristics, and the like.

Alternatively a nucleic acid construct without promoter may be targeted or randomly selected for integration into a chromosomal region that is transcriptionally active, e.g. behind a promoter present in the genome. Selection for cells containing the DNA of the invention can be performed by selecting for the selectable marker polypeptide, using routine methods known by the person skilled in the art. When such a nucleic acid construct without promoter is integrated behind a promoter in the genome, a nucleic acid construct according to the invention can be generated in situ, i.e. within the genome of the host cells.

Preferably the host cells are from a stable clone that can be selected and propagated according to standard procedures known to the person skilled in the art. A culture of such a clone is capable of producing gene product of interest, if the cells comprise the multicistronic transcription unit of the invention.

Introduction of nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like. Suitable host cells that express the gene product of interest can be obtained by selection.

In preferred embodiments, a nucleic acid construct according to the invention is integrated into the genome of the eukaryotic host cell according to the invention. This will provide for stable inheritance of the nucleic acid construct.

In a fifth aspect, the present invention relates to a method of generating a host cell for expression of a gene product of interest, wherein the method comprises the steps of: a) introducing into a plurality of host cells a nucleic acid construct according to the invention or a expression vector according to the invention; b) culturing the plurality of host cells obtained in a) under conditions selecting for expression of the selectable marker polypeptide; and, c) selecting at least one host cell expressing the selectable marker polypeptide for expression of the gene product of interest.

Advantages of this method are similar to those described for the method disclosed in WO 2006/048459 (e.g. page 46-47), incorporated by reference herein. While clones having relatively low copy numbers of the nucleic acid construct and high expression levels can be obtained, the selection system of the invention nevertheless can be combined with amplification methods to even further improve expression levels. This can for instance be accomplished by amplification of a co-integrated DHFR gene using methotrexate, for instance by placing DHFR on the same nucleic acid molecule as the multicistronic transcription unit of the invention, or by cotransfection when DHFR is on a separate DNA molecule. The DHFR gene can also be part of a nucleic acid construct of the invention or of the expression vector of the invention.

Selection for the presence of the selectable marker polypeptide, and hence for expression, can be performed during the initial obtaining of the host cell. In certain embodiments, the selection agent is present in the culture medium at least part of the time during the culturing, either in sufficient concentrations to select for cells expressing the selectable marker or in lower concentrations.

In a sixth aspect, the present invention relates to a method of expressing a gene product of interest, comprising culturing a host cell comprising a nucleic acid construct according to the invention or a vector according to the invention, a host cell according to the invention or a host cell obtained in a method according to the invention, and expressing the gene product of interest from the nucleic acid construct. In preferred embodiments, selection agent is no longer present in the culture medium during final the production phase of gene product of interest so as to avoid any risk of contamination of the gene product with trace of the possibly noxious selection agent.

In certain embodiments, an expression vector of the invention encodes an immunoglobulin heavy or light chain or an antigen binding part, derivative and/or analogue thereof. In a preferred embodiment a protein expression unit according to the invention is provided, wherein said protein of interest is an immunoglobulin heavy chain. In yet another preferred embodiment a protein expression unit according to the invention is provided, wherein said gene product of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression vectors, or on a single expression vector. Thus, the heavy and light chain can each be present on a separate expression vector, each having its own promoter (which may be the same or different for the two expression vectors), each comprising a transcription unit according to the invention, the heavy and light chain being the gene product of interest, and preferably each coding for a different selectable marker protein, so that selection for both heavy and light chain expression vector can be performed when the expression vectors are introduced and/or present in a eukaryotic host cell. Alternatively, the heavy and light chain coding sequences can be present on a single expression vector comprising a multicistronic transcription unit according to the invention, driven from a single promoter, and wherein the light and heavy chains are the gene products of interest with an IRES in between their respective coding sequences.

Culturing a cell is done to enable it to metabolize, and/or grow and/or divide and/or produce gene products of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant gene products through cell culture it is preferred in the art to have cells capable of growing in suspension, and it is preferred to have cells capable of being cultured in the absence of animal- or human-derived serum or animal- or human-derived serum components.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, a method of expressing a gene product of interest according to the invention further comprises harvesting the gene product of interest. The expressed gene product, e.g. protein may be harvested, collected or isolated either from the cells or from the culture medium or from both. It may then be further purified using known methods, e.g. filtration, column chromatography, etc, by methods generally known to the person skilled in the art.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, 2$^{nd}$ edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988. [0088] The invention is further explained in the following examples. The examples do not limit the invention in any way. They merely serve to clarify the invention.

In this document and in its claims, the verb “to comprise” and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 1 shows the six ~3500 bp DNA stretches upstream from the transcription start site, as well as a ~3500 bp DNA stretch coding region of the genes, encompassing the start of translation in the corresponding mRNA (dubbed Z) for each locus. The six upstream DNA stretches, containing only non-coding DNA, were dubbed A to F.

CHO-DG44 cells were transfected with 3 μg DNA of constructs as shown, using TTG-Zeo (in FIG. 2A) or pp 8-Zeo-EPP5 (in FIG. 2B) as selectable marker. For the negative control there is no sequence introduced as Element X. For the positive control STAR 7/67 is used as Element X at the 5' end and STAR 7 is used as Element X at the 3' end. The different stretches of DNA of FIG. 1 were used as element X as indicated. Selection was performed with 400 μg/ml Zeocin in the culture medium, which was added 24 hours after transfection. The culture medium consisted of HAMF12: DMEM=1:1+4.6% fetal bovine serum. After approximately two weeks the number of stably established colonies were counted.

Figure 3:
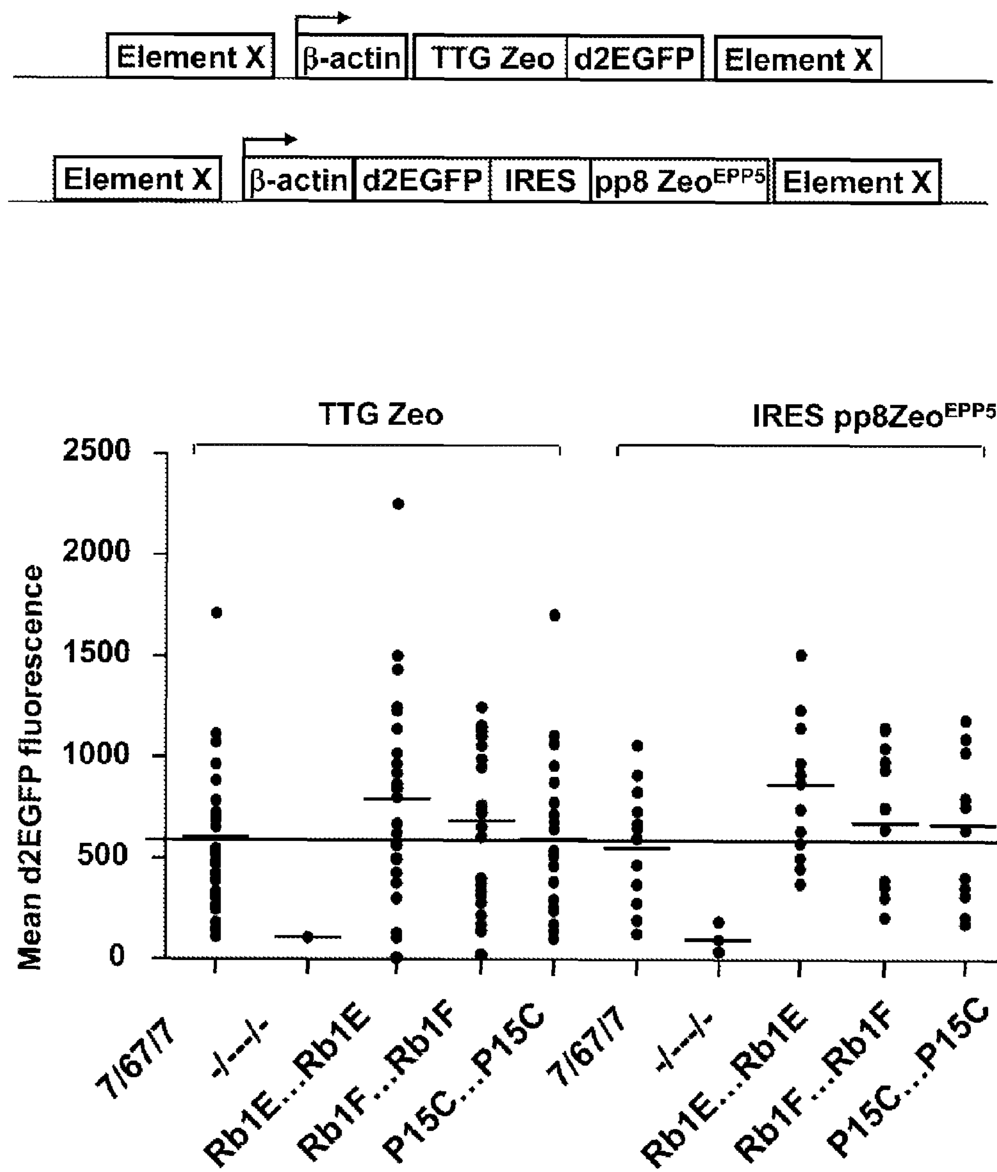

FIG. 3. Rb1E, Rb1F and p15C induce equal or higher GFP expression levels than STAR elements.

d2EGFP expression levels were determined in stable colonies comprising DNA constructs described in FIG. 2. The relative fluorescence levels were taken as arbitrary units. The average d2EGFP expression levels for each construct are indicated with a line. The average d2EGFP expression of 615 induced by STARs 7/67/7 in the context of the TTG Zeo selection system is indicated with a bold line.

Figure 4:
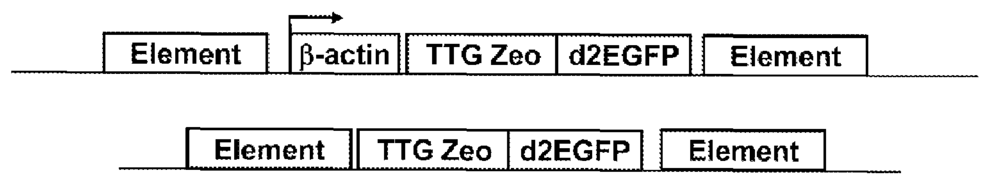
Figure 4:
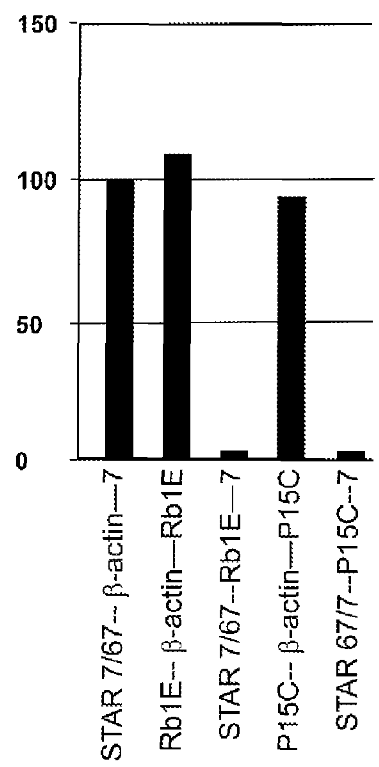
Figure 4:
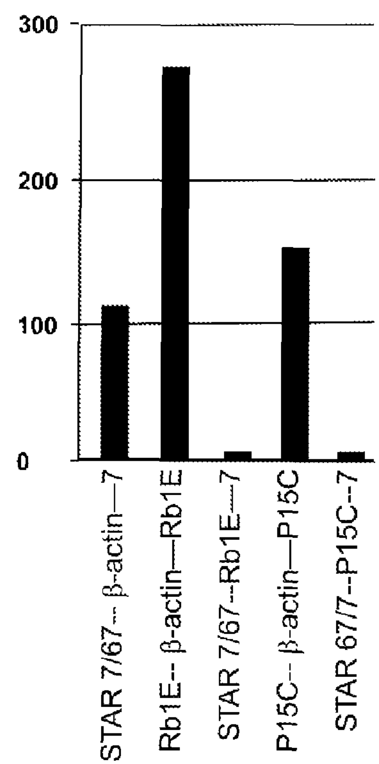

FIG. 4. Rb1E and p15C elements do not possess promoter activity.

The construct that contained STARs 7/67/7 and the β-actin promoter was modified in such a way that the β-actin promoter was replaced by either the Rb1E or p15C element. This created constructs that contained the Rb1E and p15C elements placed immediately upstream of the TTG Zeo d2EGFP cassette. As a control the constructs described in FIG. 2, that did harbor the β-actin promoter were used. We transfected the constructs to CHO-DG44 cells and measured the transient d2EGFP values. FIG. 4A shows the relative transient d2EGFP values. FIG. 4B shows the number of stable Zeocin resistant colonies.

Figure 5:
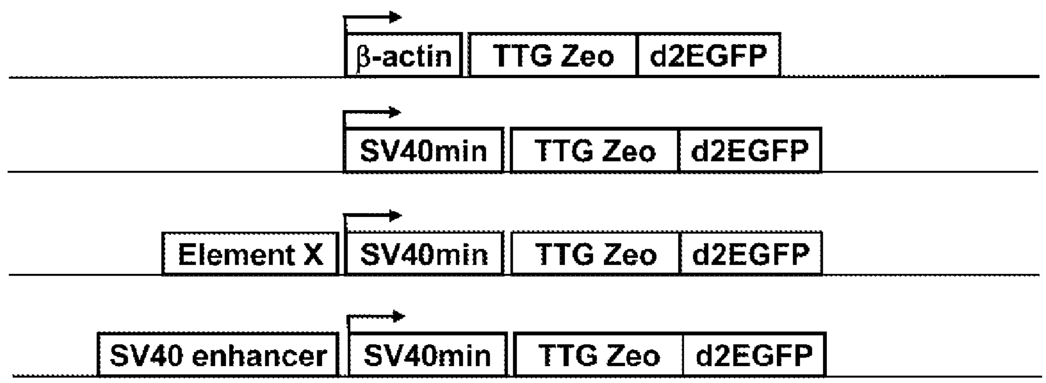
Figure 5:
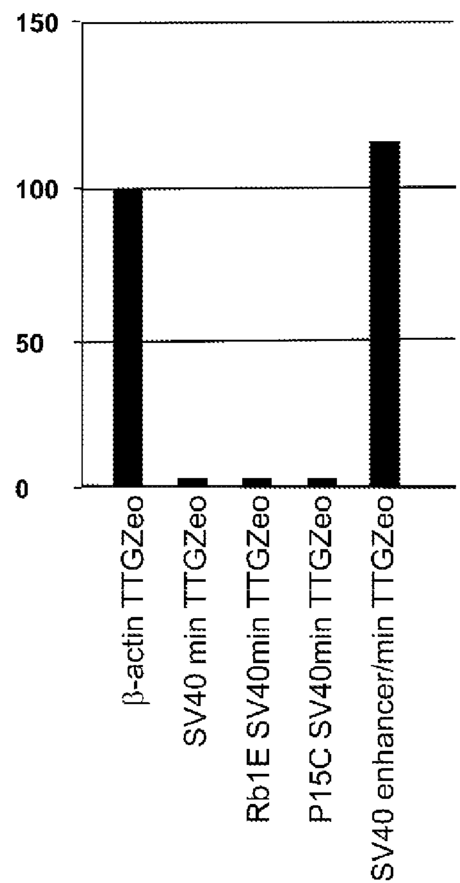

FIG. 5. Rb1E and p15C elements are no enhancers.

Constructs as indicated in FIG. 5 were made. The Rb1E or p15C element was placed upstream of the SV40 minimal promoter and the combined TTG Zeo-d2EGFP gene. As control the β-actin promoter was placed upstream of the TTG Zeo-d2EGFP gene. In another control the SV40 minimal promoter was placed upstream of the TTG Zeo-d2EGFP gene. FIG. 5 shows the relative transient d2EGFP values of the different constructs.

Figure 6:
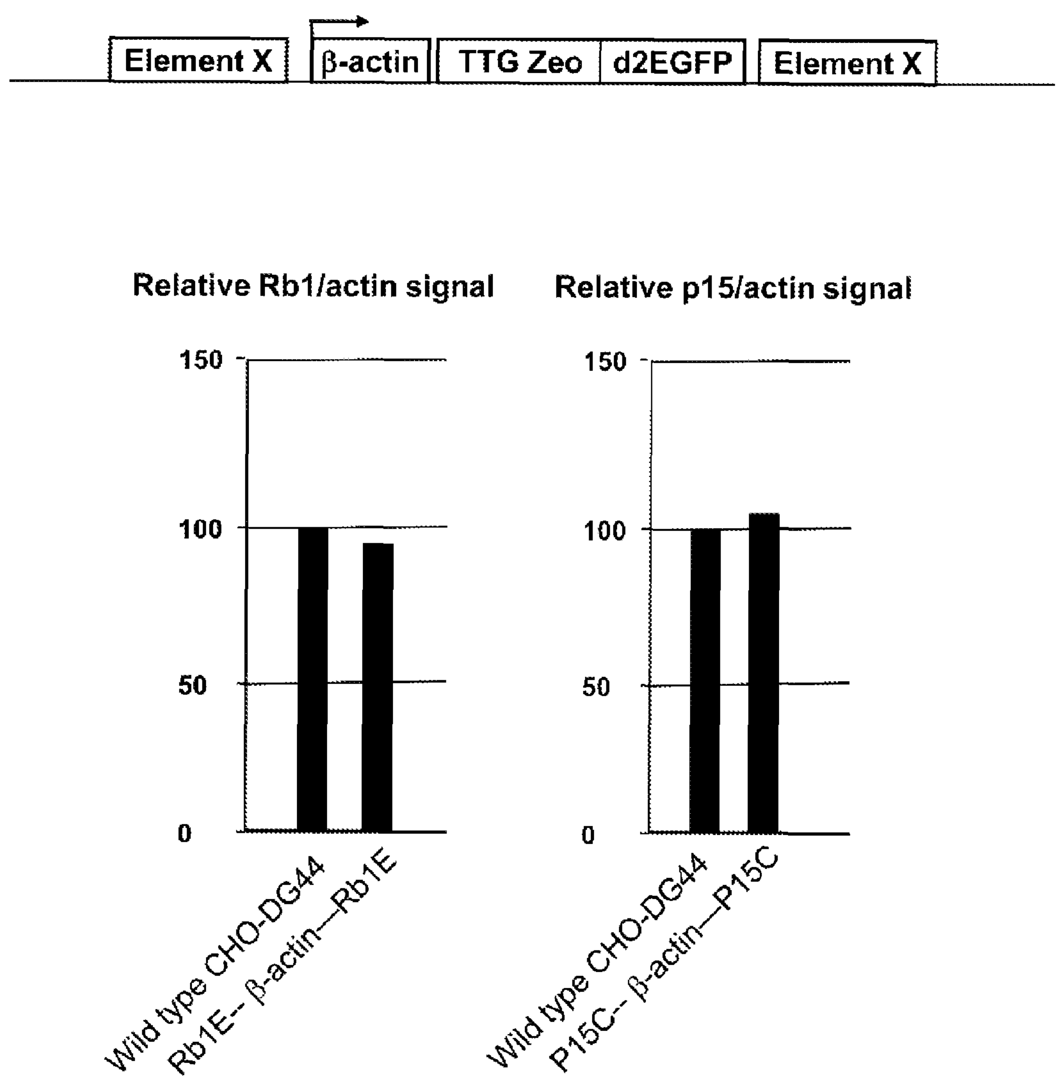

FIG. 6. Rb1E and p15C elements do not in trans influence transcription of the endogenous Rb1 and p15 promoters.

FIG. 6 shows the relative Rb1/actin signal and the relative p15/actin signal as compared to wild type CHO-DG44. The ratio of the β-actin and the Rb1 mRNA level or the β-actin and the p15 mRNA level was determined by real time PCR. Four independent clones of each element were compared.

Figure 7:
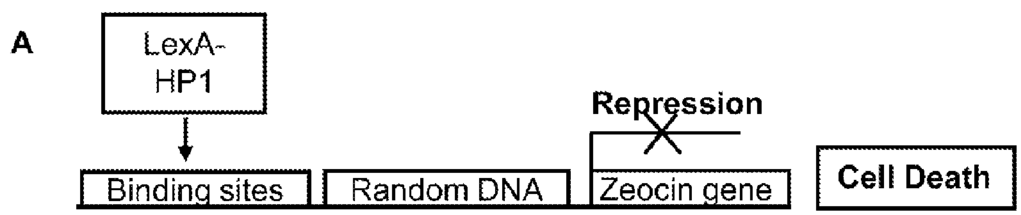
Figure 7:
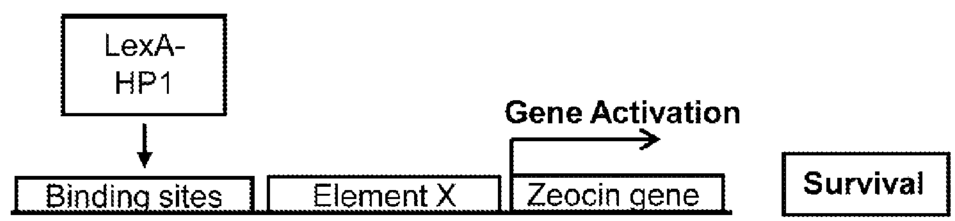

FIG. 7. Rb1E and p15C elements do not contain STAR activity.

FIG. 7A shows schematically what happens if an element has STAR activity or not. In short, the elements were placed between targeted LexA-HP1 repressors and the Zeocin selection gene. When the elements have no STAR activity, the HP1-mediated gene repression will silence the Zeocin selection marker gene. Subsequent addition of Zeocin to the culture medium will result in cell death. On the other hand, when an element does contain STAR activity, the HP1-mediated gene repression is not strong enough to silence the Zeocin selection marker. Subsequent addition of Zeocin to the culture medium will result in survival of these cells. FIG. 7B shows the results on survival of U2-OS cells, a human cell line (Human Osteosarcoma Cell line, ATCC HTB-96; described in Heldin, C H, et al. 1986, Nature 319: 4511-514).

Figure 8:
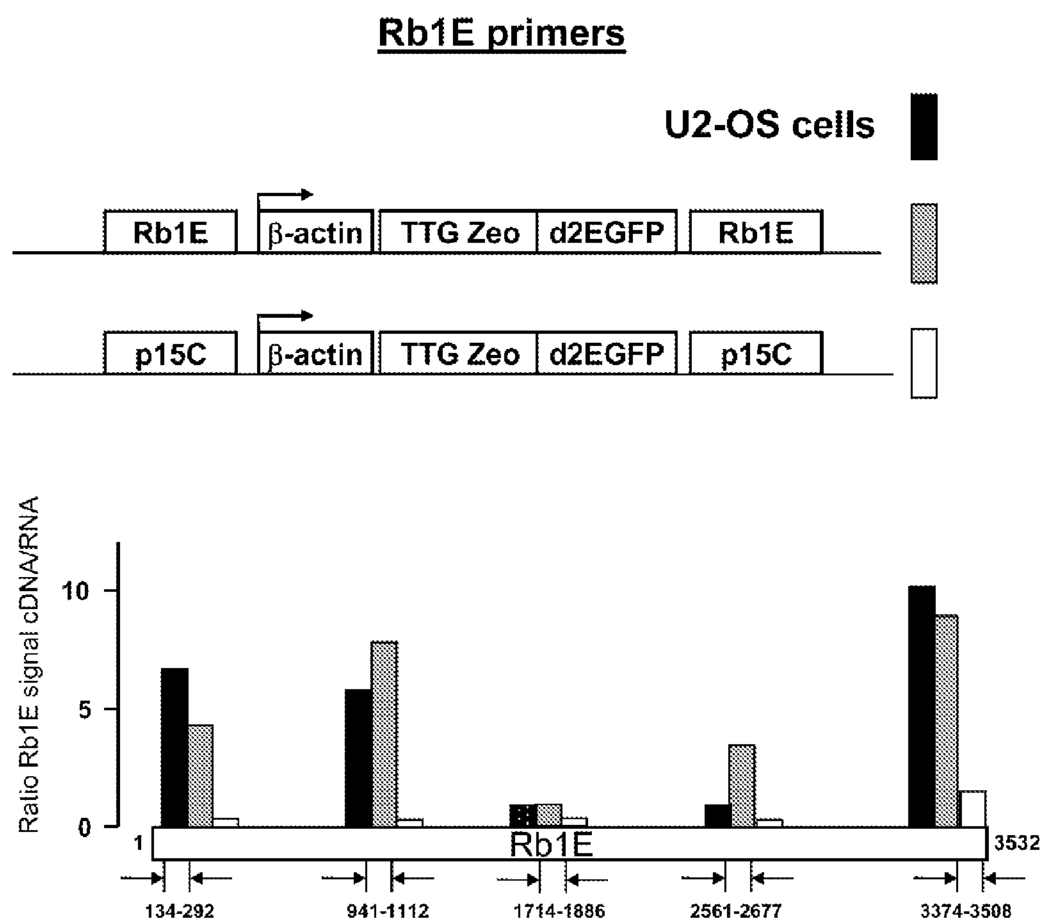
Figure 9:
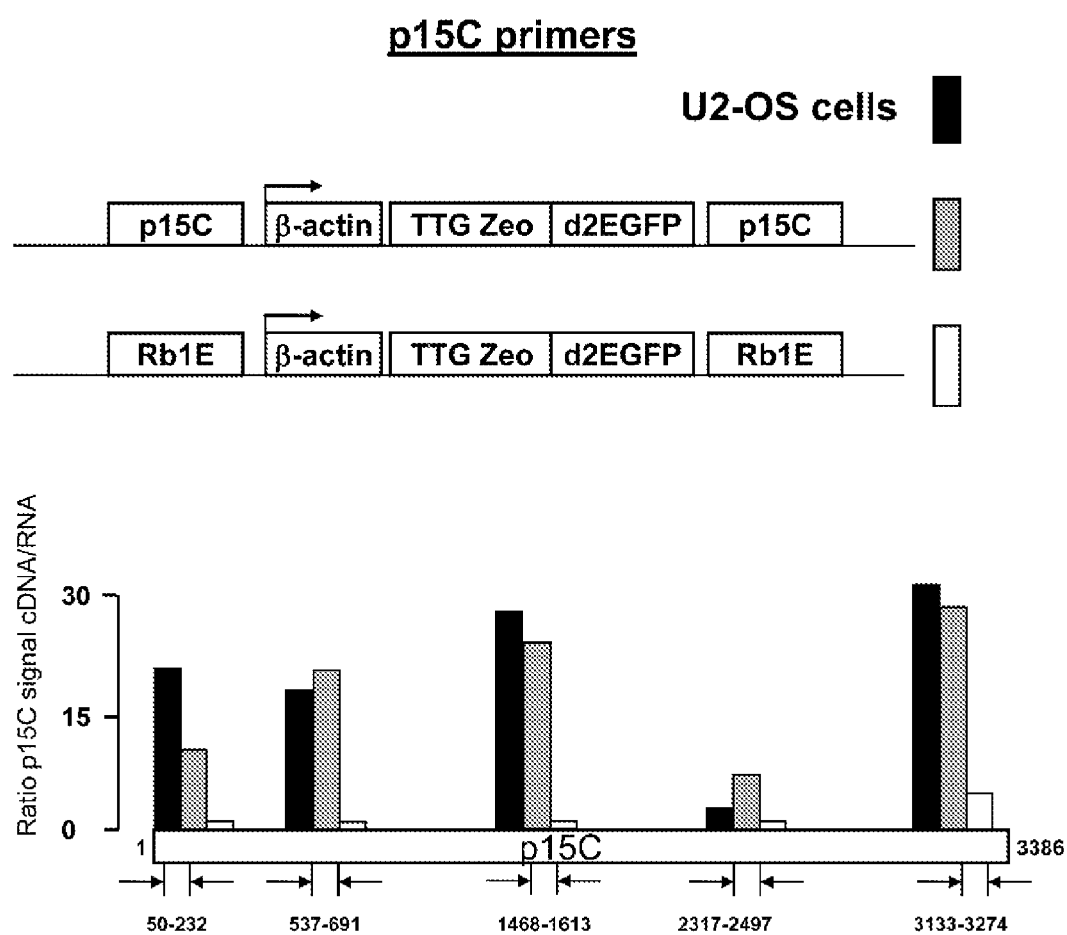

FIGS. 8 and 9. The Rb1E element and the p15C element are a source of intergenic transcription.

To determine whether intergenic transcripts are associated with the Rb1E and p15C elements, four primer sets were designed for the Rb1E and p15C genomic elements. Using random hexamers cDNA was made from total RNA isolated from U2-OS cells. Using real time PCR it was determined whether there was an elevated level of RNA, transcribed across the tested region. The real time PCR reactions were performed on the cDNA, created from U2-OS cells. As control, the total RNA from which the cDNA was made, was used as sample for the real time PCR reaction. The difference in the respective signal levels in the RNA or cDNA samples was taken as measure for the level of intergenic transcripts. FIG. 8 shows the results for the Rb1E primers. FIG. 9 shows the results for the p15C primers.

Figure 10:
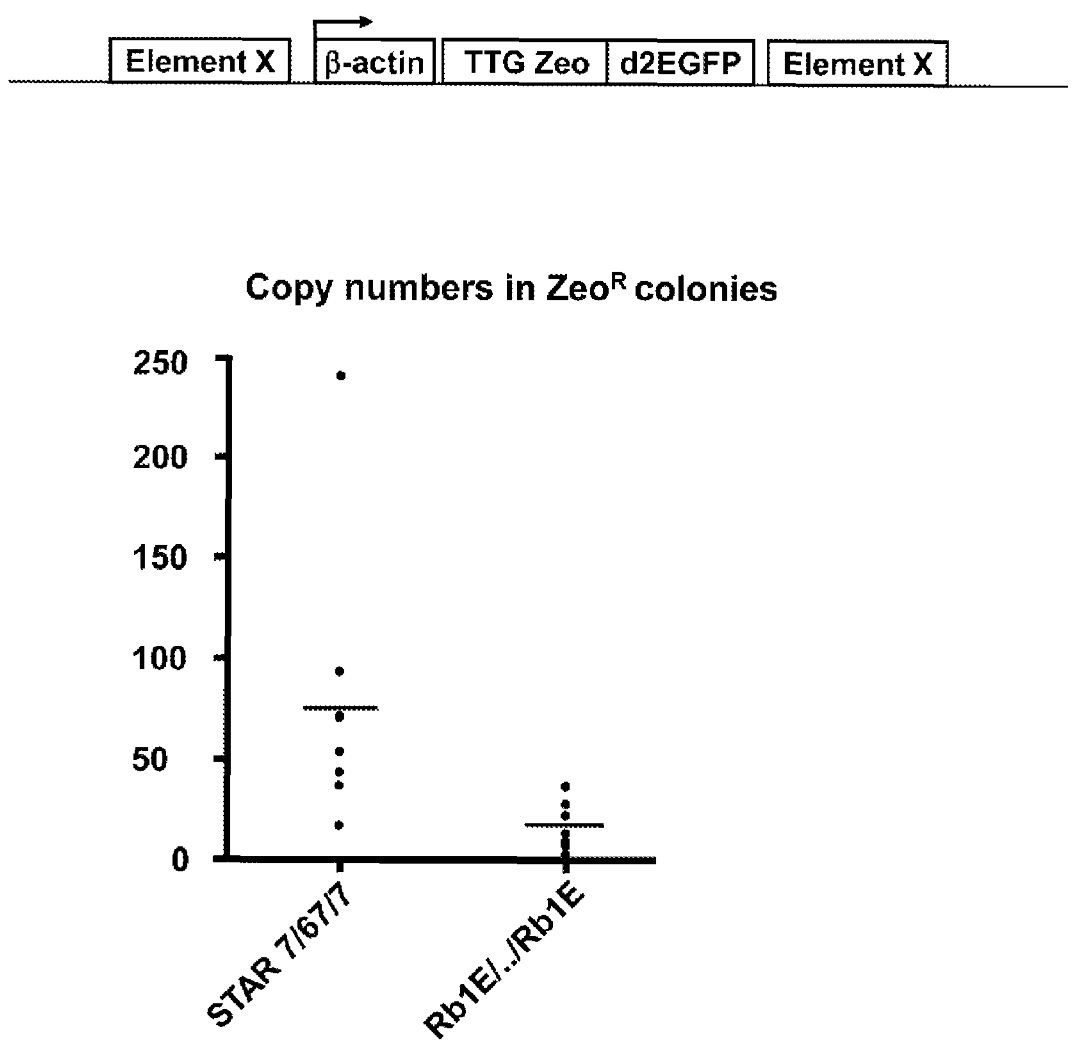

FIG. 10. Copy numbers in clones that contain Rb1E or STAR elements.

Figure 11:
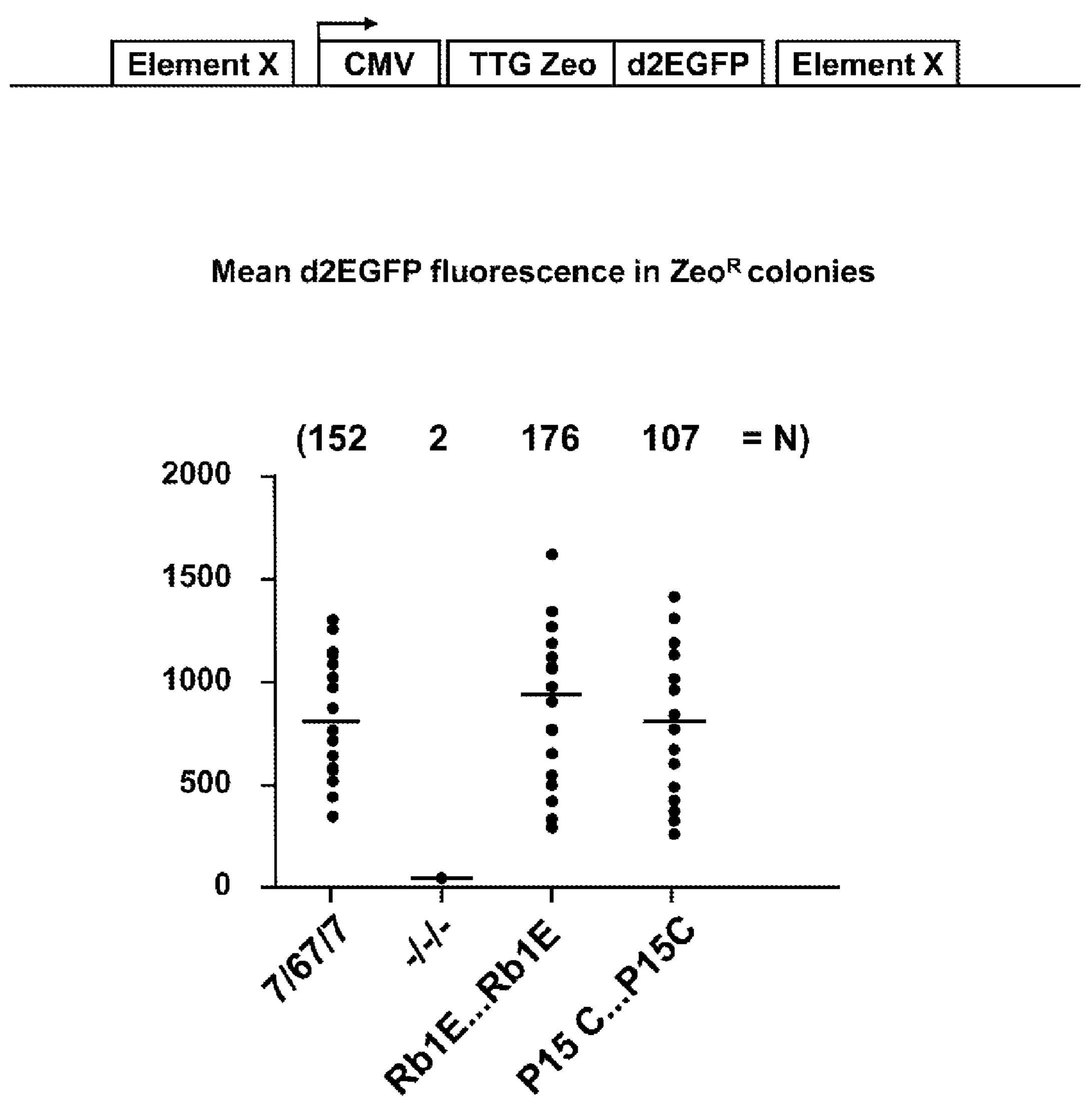

FIG. 11. Rb1E and p15C are functional in the context of different promoters.

FIG. 11 shows the mean d2EGFP fluorescence level in Zeocin resistant colonies after transfection with the construct comprising the CMV promoter as schematically presented in FIG. 11. The number of colonies that was induced is indicated above the graph.

Figure 12:
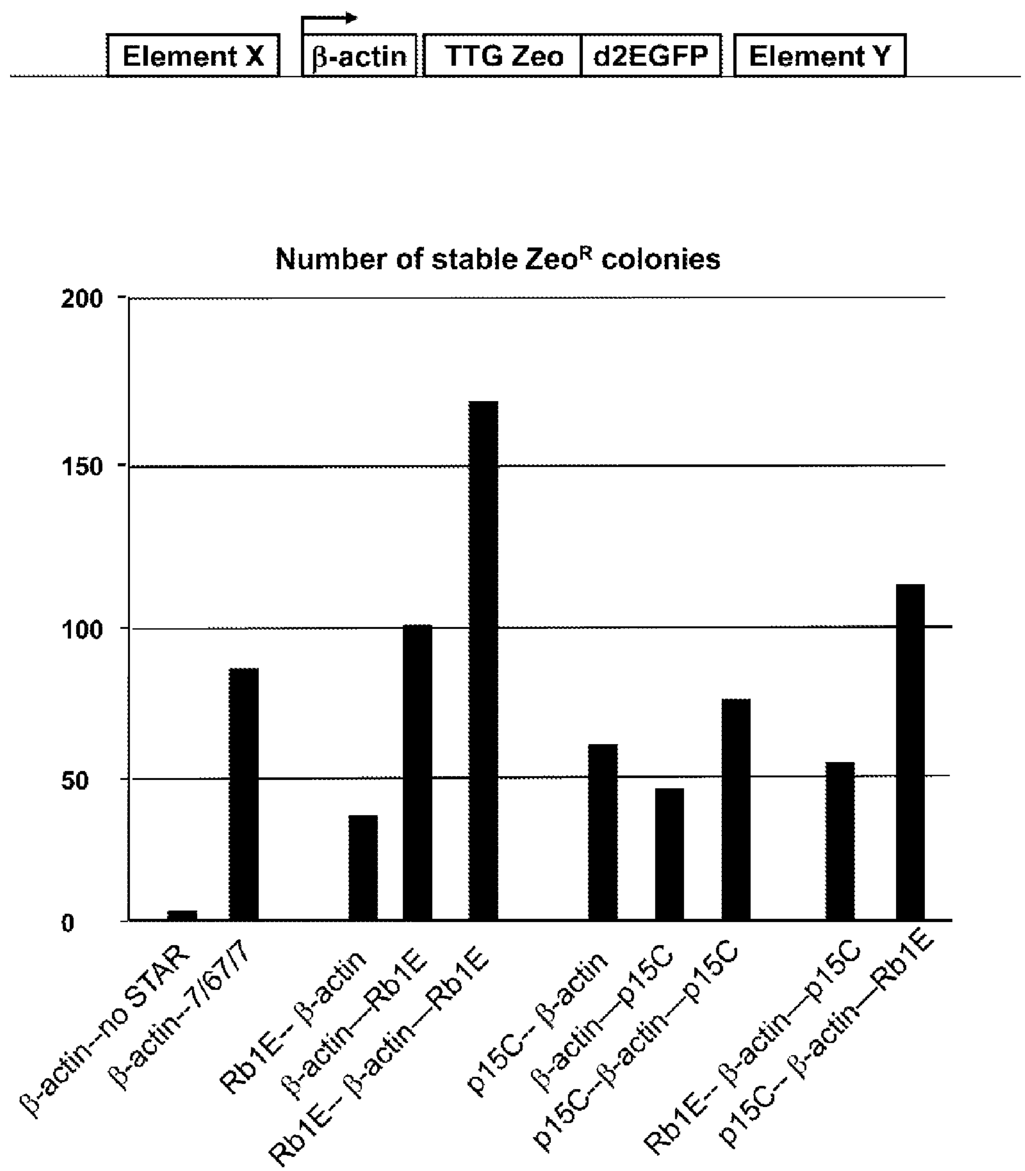

FIG. 12. Specific combinations of Rb1E and p15C to induce optimal colony numbers and protein expression levels.

In FIG. 12 the number of stable Zeocin resistant colonies is shown, whereby the colonies were transfected with a construct as schematically presented in FIG. 12 and wherein element X and element Y are indicated on the X-axis.

Figure 13:
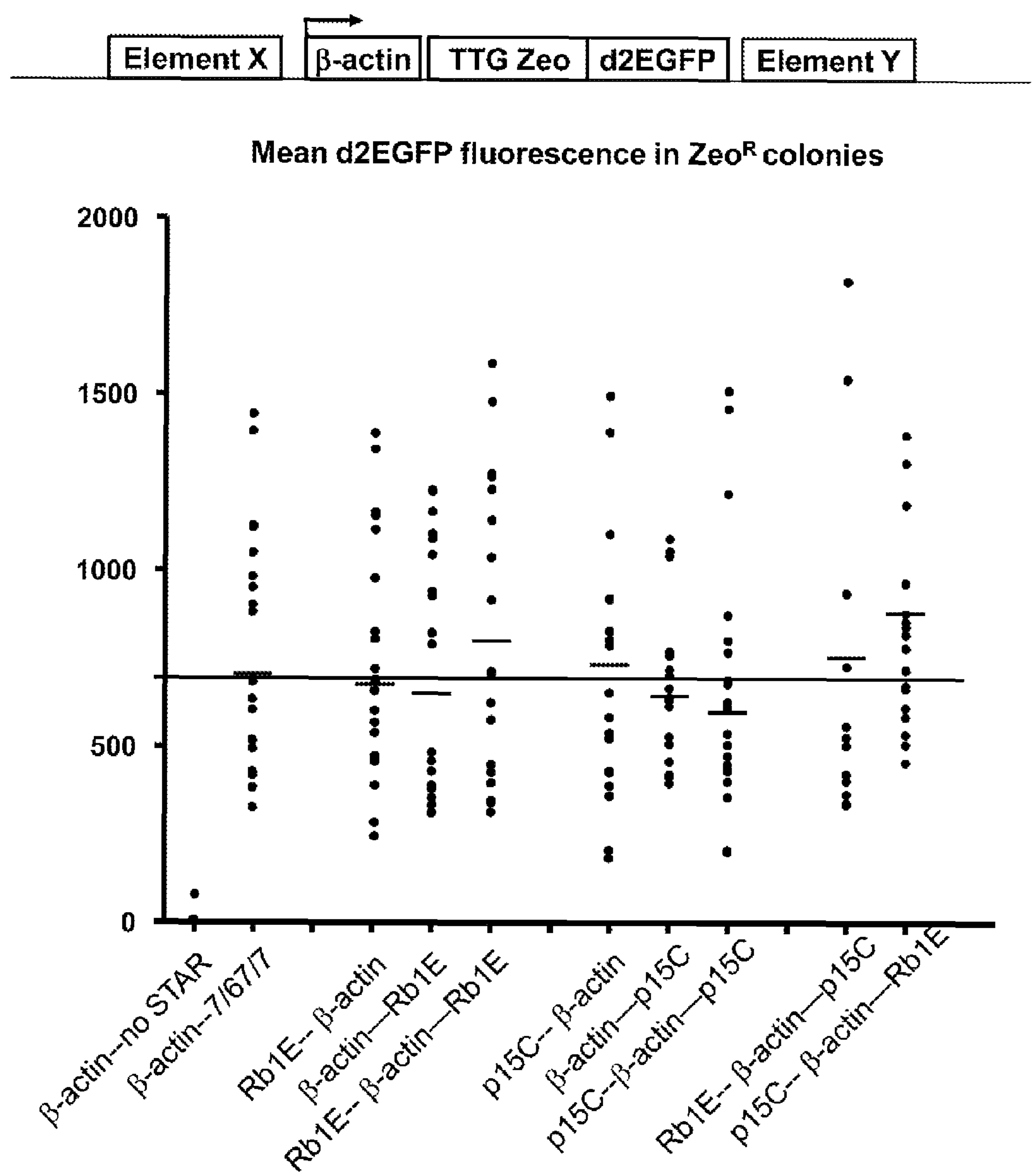

FIG. 13. Specific combinations of Rb1E and p15C to induce optimal colony numbers and protein expression levels.

In FIG. 13, the mean d2EGFP fluorescence level in the cells of FIG. 12 are shown.

Figure 14:
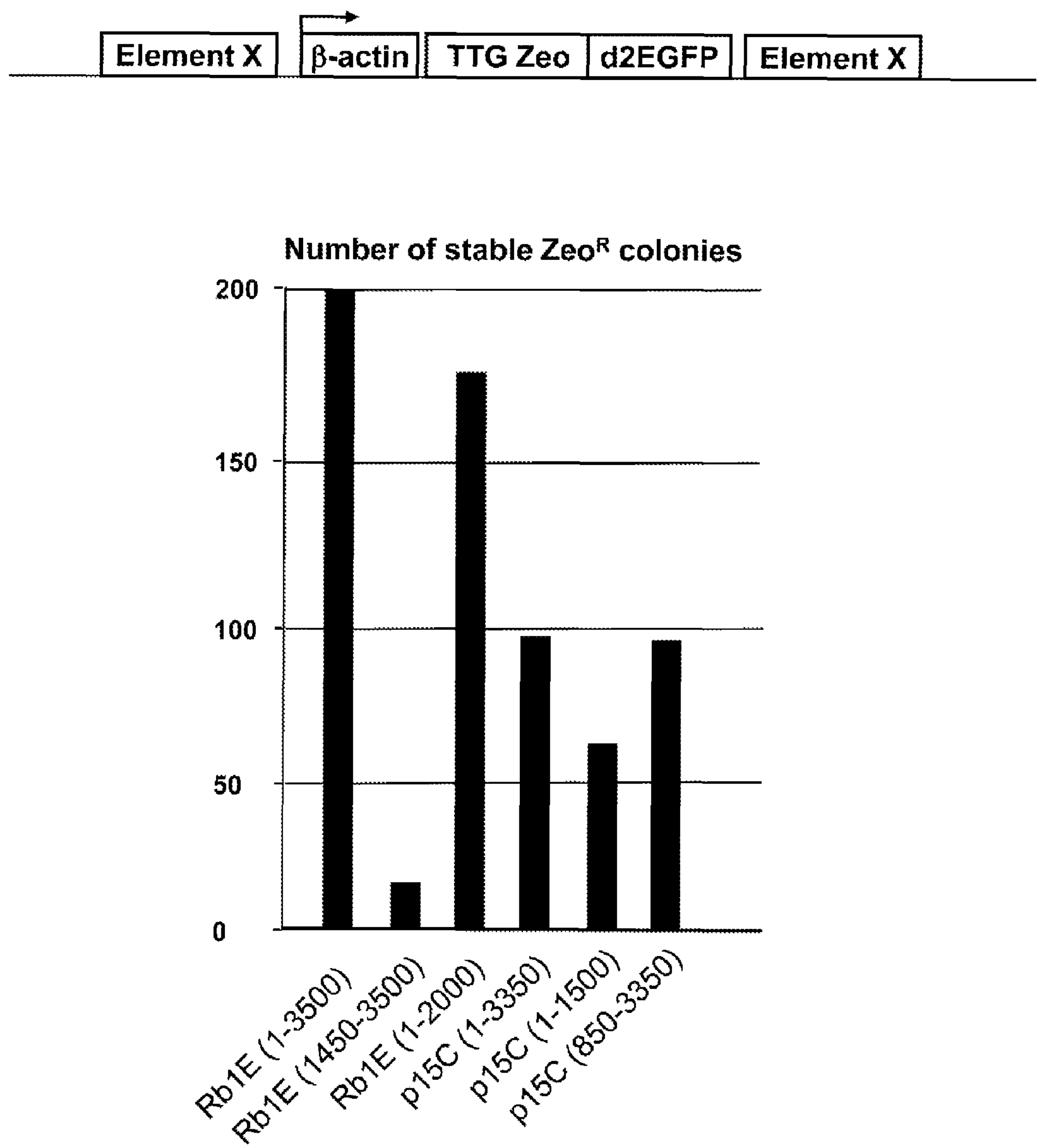

FIG. 14. Testing of regions within Rb1E and p15C for highest activity.

FIG. 14 shows the number of stable Zeocin resistant colonies after transfection with a construct as schematically indicated in FIG. 14 and wherein Element X are either the full Rb1E or p15C elements or a part thereof.

Figure 15:
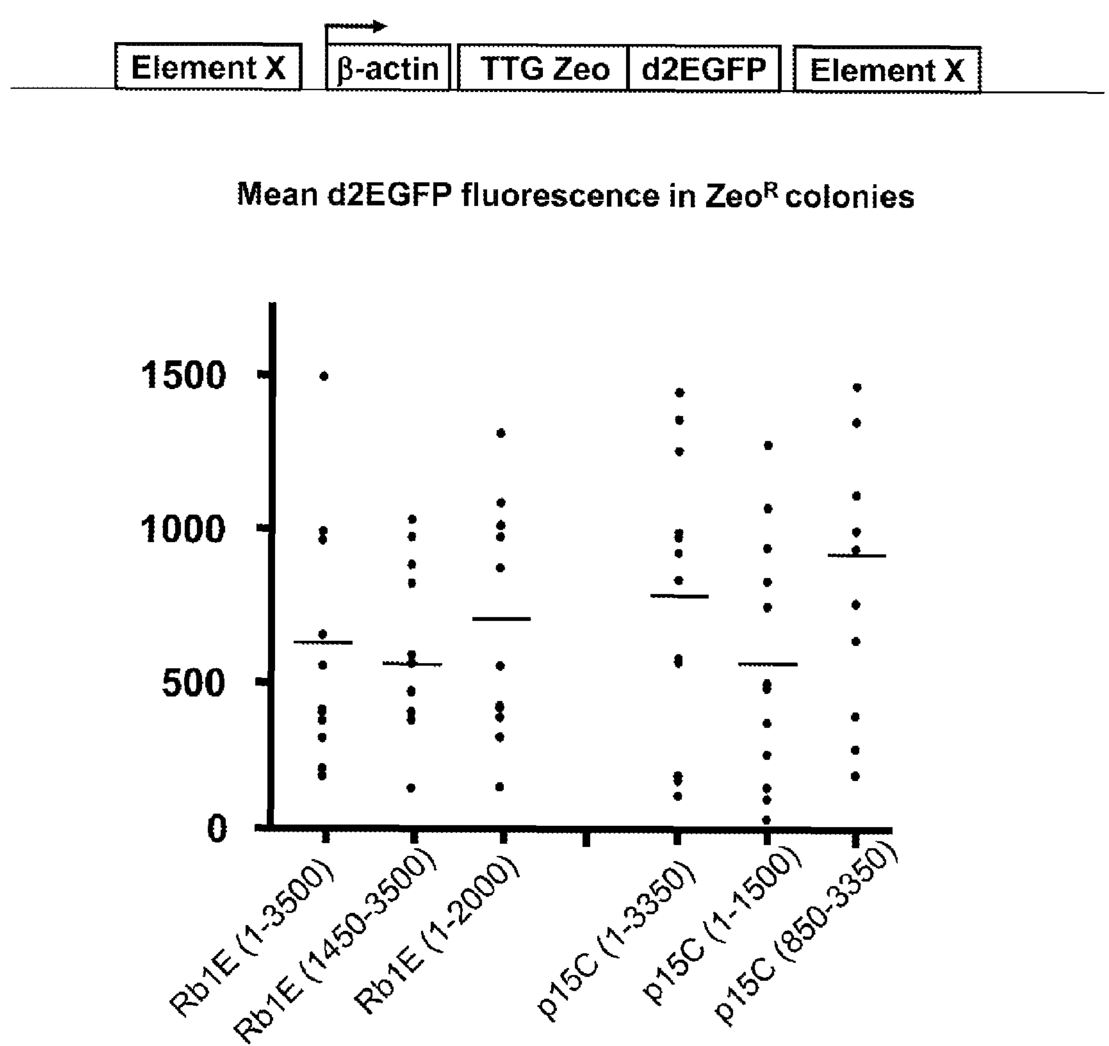

FIG. 15. Testing of regions within Rb1E and p15C for highest activity.

In FIG. 15, the mean d2EGFP fluorescence level in the cells of FIG. 14 are shown.

Figure 16:
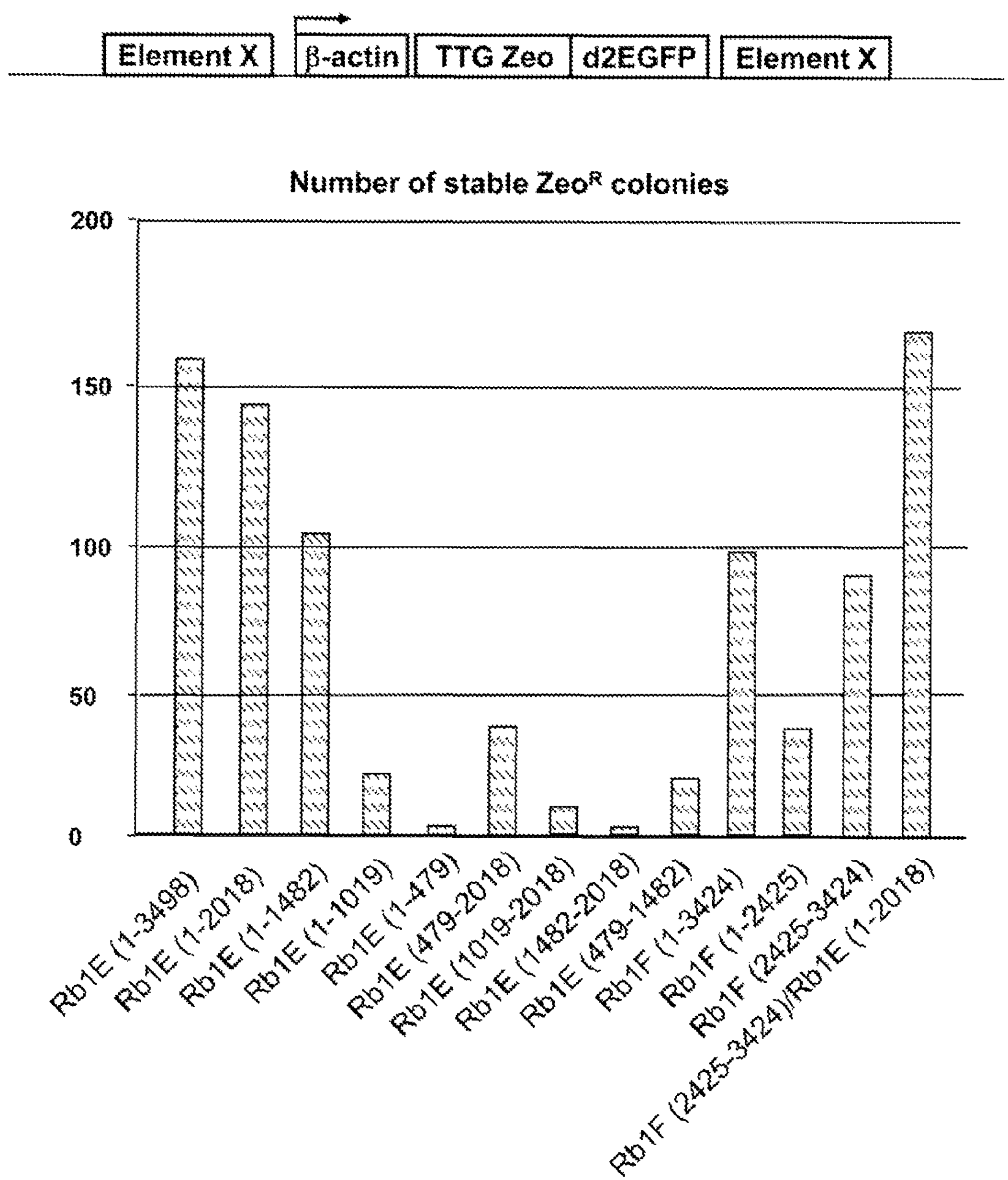

FIG. 16. Testing of regions within Rb1E and Rb1F and a combination thereof for number of stable colonies. The following fragments were tested for number of stable colonies they produced: Rb1E: 1-3498, 1-2018, 1-1482, 1-1019, 1-479, 479-2018, 1019-2018, 1482-2018, 479-1482; Rb1F: 1-3424, 1-2425, 2425-3424; Rb1E/Rb1F: 2425-3424 (Rb1F)-1-2018 (Rb1E).

Figure 17:
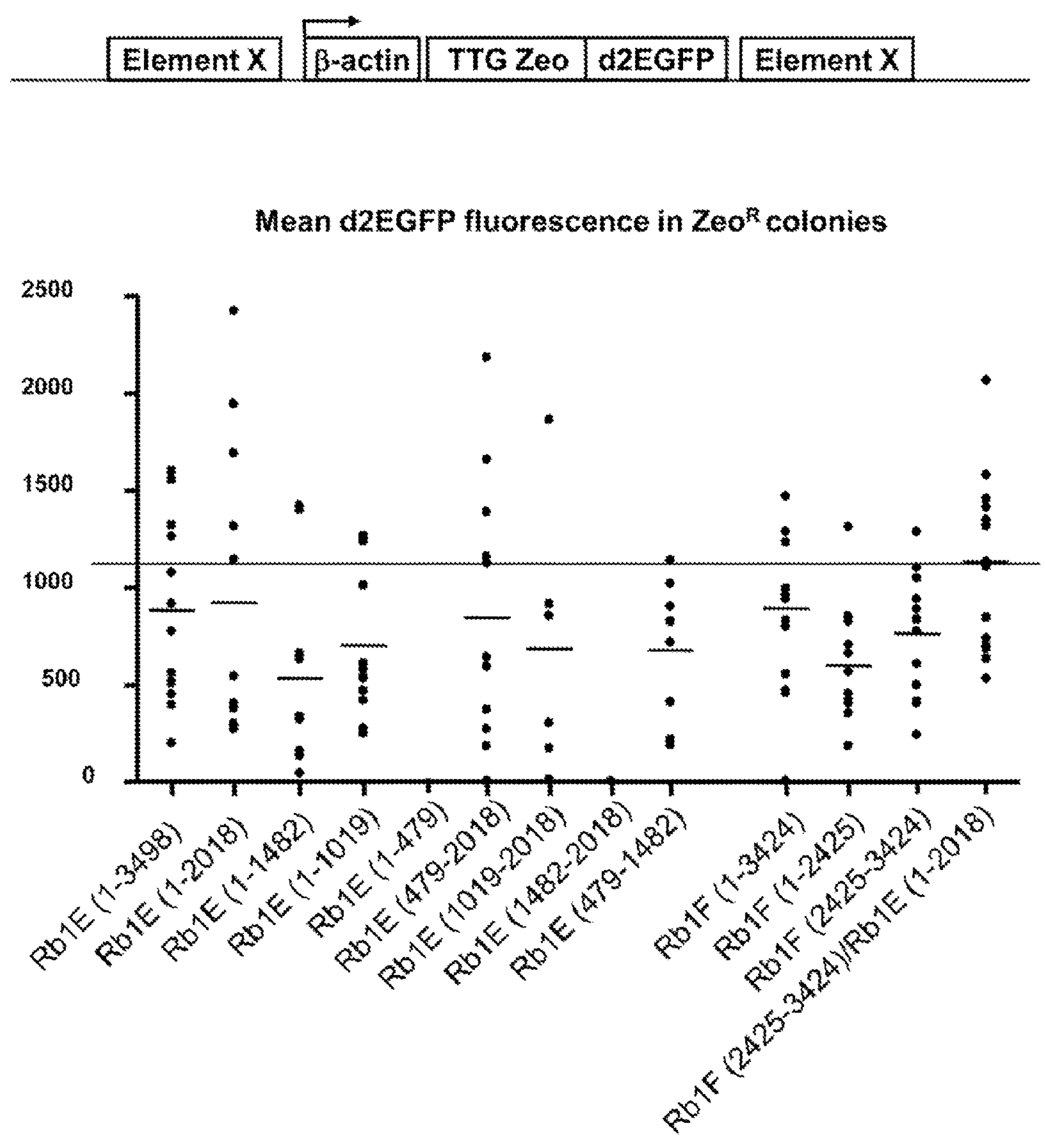

FIG. 17. Testing of regions within Rb1E and Rb1F and combination thereof for activity. The following fragments were tested for number of stable colonies they produced: Rb1E: 1-3498, 1-2018, 1-1482, 1-1019, 1-479, 479-2018, 1019-2018, 1482-2018, 479-1482; Rb1F: 1-3424, 1-2425, 2425-3424; Rb1E/Rb1F: 2425-3424 (Rb1F)-1-2018 (Rb1E).

Figure 18:
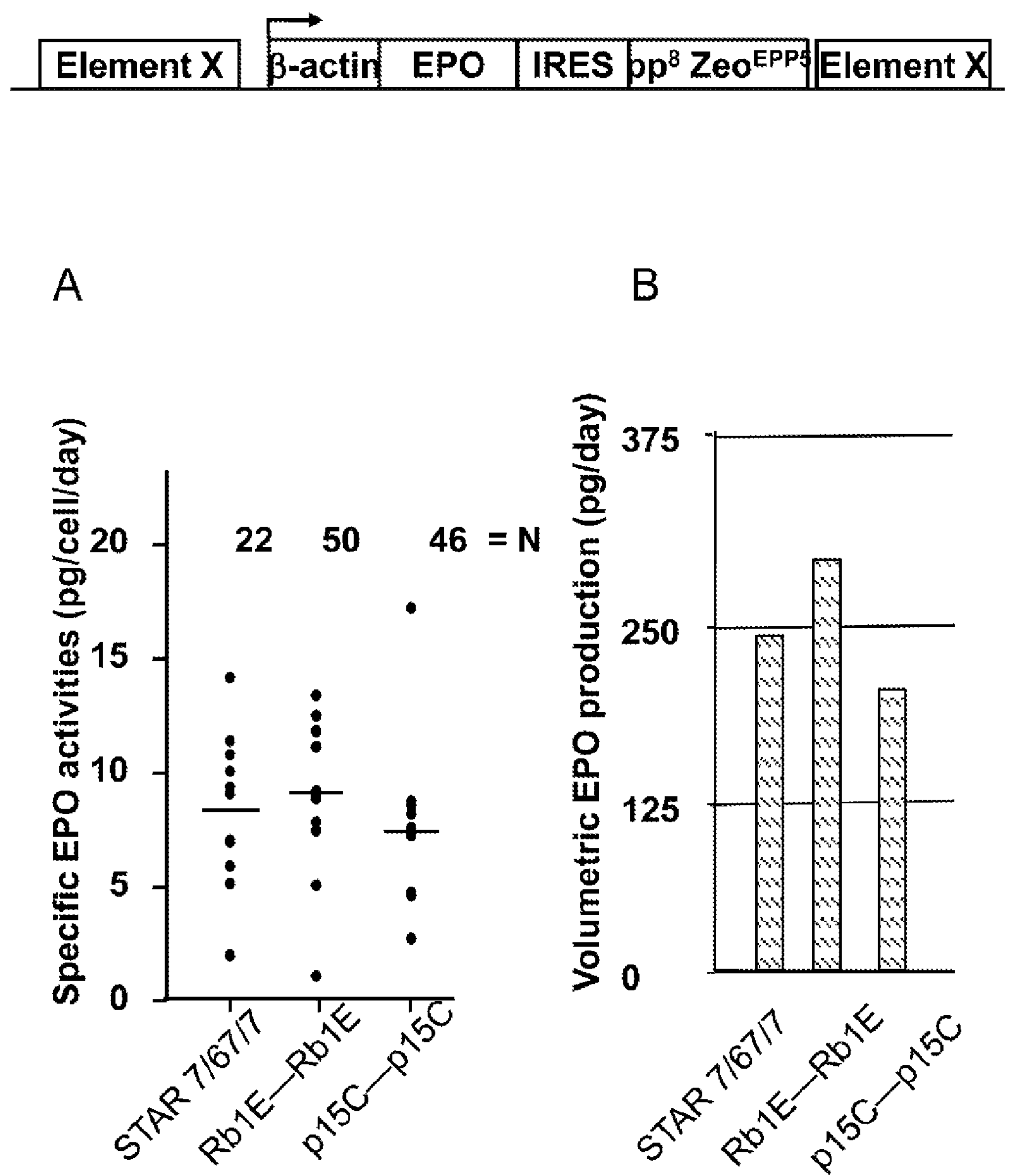

FIG. 18. Rb1E and p15C induce high EPO protein expression levels.

EPO production levels are shown as achieved in cells that were stably transfected with the construct as schematically presented. The EPO reporter gene was under control of the β-actin promoter. As selectable marker the $pp^8Zeo^{EPP5}$ variant was used. FIG. 18A shows the specific EPO activity in pg per cell per day. FIG. 18B shows the volumetric EPO production in pg of EPO per day.

EXAMPLES

Figure 1:
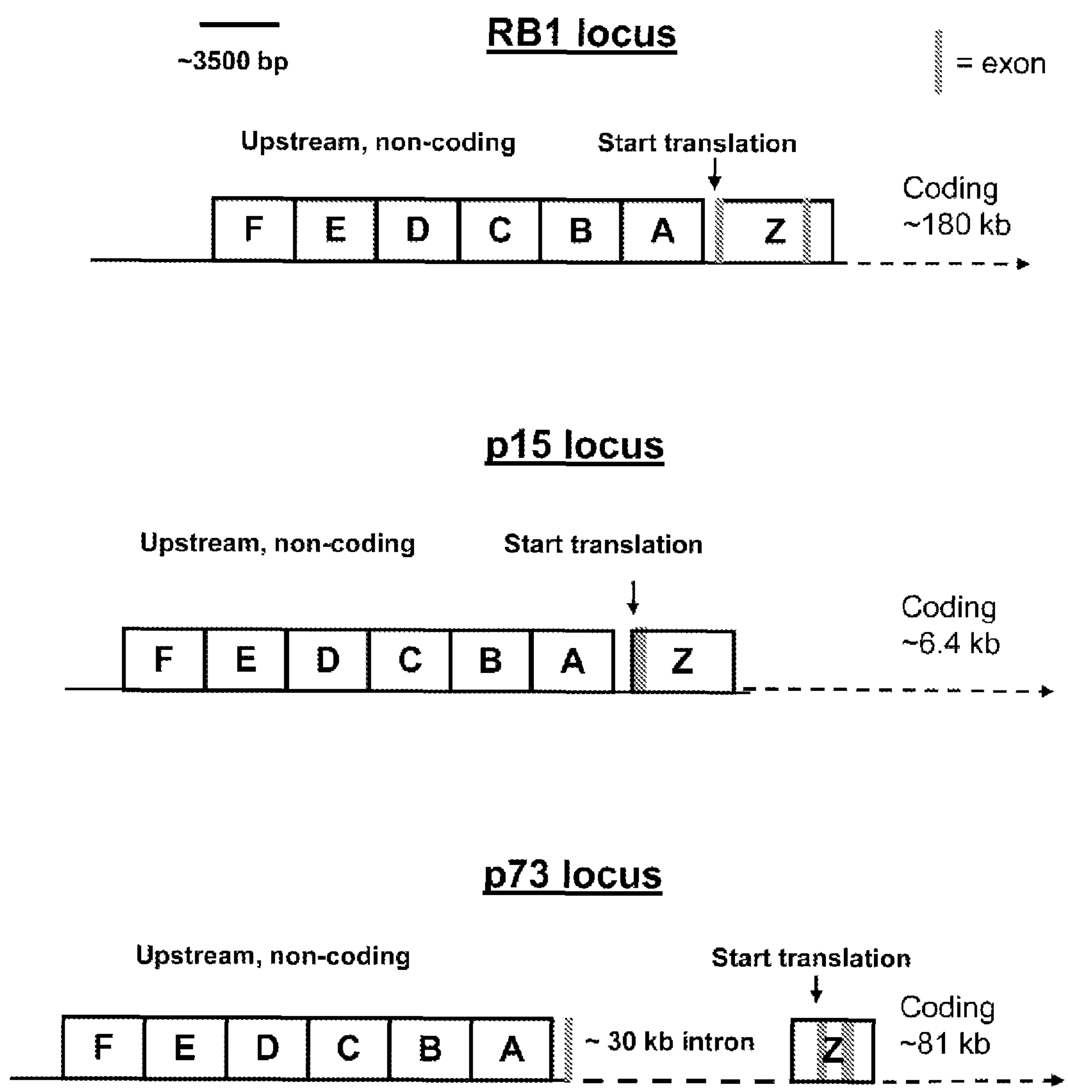
FIG. 1. Genomic structure of genes that are screened for fragments that elevate the formation of colonies in the context of a stringent selection system.
Figure 2A:
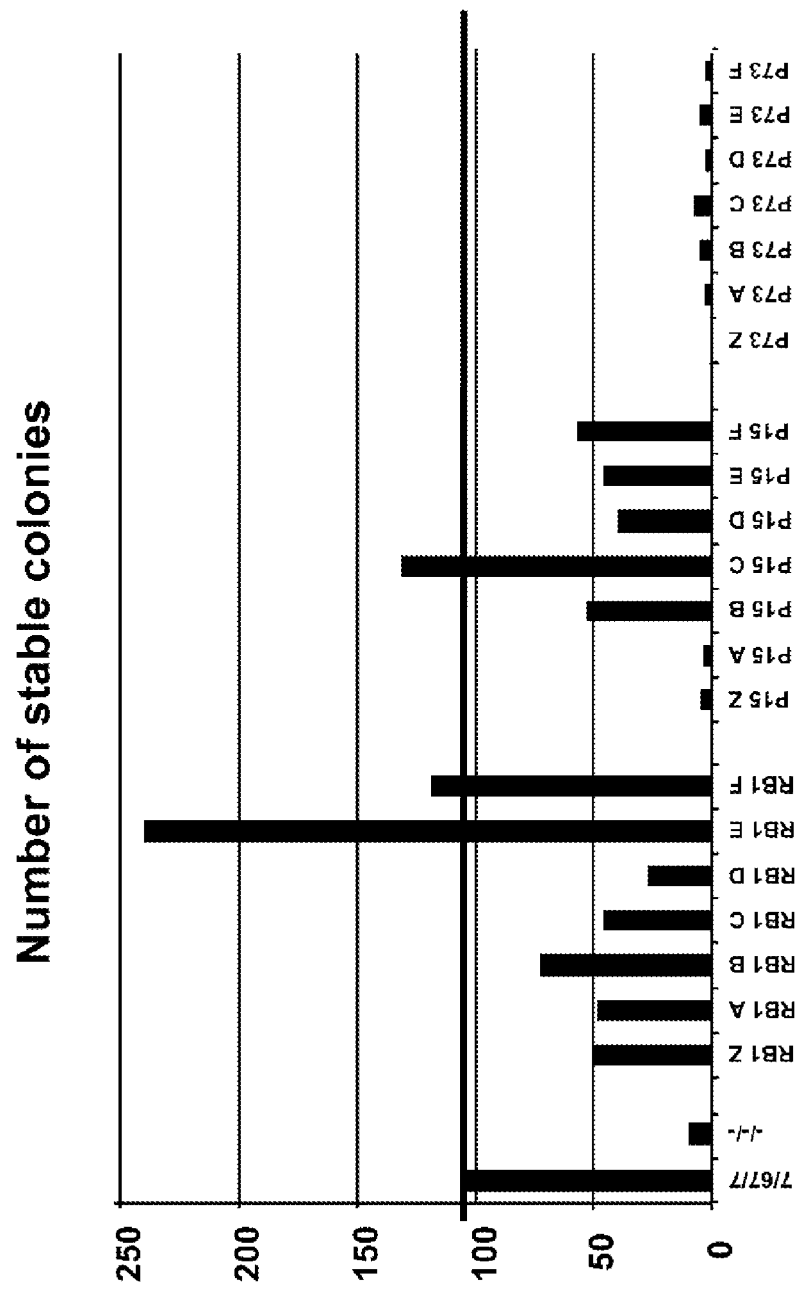
FIG. 2. Genomic sequences that induce more colonies than STAR elements in the context of stringent selection systems.

1. Example 1: Screening Specific Genomic Loci for Sequences that Convey Equal or More Stably Transfected Colonies than STAR Elements When CHO-DG44 are transfected with a plasmid that harbor a stringent selectable marker such as the Zeocin resistance marker that is modified at its translation initiation codon, little or no colonies will emerge. This is specifically the case with a Zeocin resistance marker that has a TTG translation initiation codon and that is placed under the control of the human β-actin promoter (SEQ ID NO: 17) (See FIG. 2A). However, when STAR elements are placed to flank the entire expression cassette, many more colonies will emerge, typically in the range of 50-100 per transfection (see for instance FIG. 2A), when 400 μg/ml Zeocin is added to the CHO-DG44 culture medium. In general, the resulting clones convey high protein expression levels. Here, we attempted to identify genomic sequences that are able to induce at least as many CHO-DG44 colonies as with STAR elements under the same selection conditions. We therefore used the same Zeocin resistance marker as is used with STAR elements, TTG Zeo. The expression cassette was placed under control of the human β-actin promoter (FIG. 2A). Genomic loci of three human genes were chosen: Rb1 (SEQ ID NO: 1), p15 and p73. Stretches of DNA of approximately the same length (~3500 bp) were isolated by PCR using BAC clones as template. The numbers of these BAC clones were respectively RP11-136N2, RP11-478M20 and RP5-1092A11 (obtained from BacPAC Resources Center-BPRC) for Rb1, p15 and p73. For each locus we isolated and analyzed six ~3500 bp DNA stretches upstream from the transcription start site, as well as a ~3500 bp DNA stretch coding region of the genes, encompassing the start of translation in the corresponding mRNA (dubbed Z). The six upstream DNA stretches, containing only non-coding DNA, were dubbed A to F (FIG. 1). The specific sets of primers are given in table 1. The particular stretches of DNA were cloned to flank a construct encompassing the human β-actin promoter, the TTG Zeo resistance gene and the d2EGFP reporter gene. A short DNA sequence run was performed on the isolated DNA sequences to verify that we indeed isolated the intended sequence. This proved to be the case. As control constructs we took the same construct without any flanking DNA element and the same construct flanked with STARs 7 and 67 (disclosed in WO 2007/096399) upstream of the expression cassette and STAR 7 (disclosed in WO 2007/096399) downstream of the expression cassette (FIG. 2A).

TABLE 1

Primer sets for the isolation of genomic elements (5' -> 3' direction)

| | forward primer | SEQ ID NO | reverse primer | SEQ ID NO |
|---|---|---|---|---|
| RB1 Z | ggagcgtctgcagaatggtgacagg | 18 | agactctcgctctgttgccaggctg | 39 |
| RB1 A | ctgaaggagtctcaaactgaagagag | 19 | acaaagagtctggtgggtgactgtg | 40 |
| RB1 B | tgtttgcattcctgtagcccacaag | 20 | cgttctaaaaagccttccttcaaag | 41 |
| RB1 C | gtgatgtaaatctttgcaattcttc | 21 | tcttaatggcttgatgagccacac | 42 |
| RB1 D | tagtcttttgtatgtgataaatctc | 22 | taccattcaattctcccgtctgac | 43 |
| RB1 E | gcccaccctaaatacttatacaggc | 23 | acaccccaggaacagaatcagtgc | 44 |
| RB1 F | actatgtcatttttgctaacatgtaatgg | 24 | gctattcactcattcctgtagctgtctaat | 45 |
| P15 Z | ggggactagtggagaaggtgcgaca | 25 | ccagggcttccagagagtgtcgttta | 46 |
| P15 A | cctcttggtgggaaggtgtgttcataa | 26 | aagcctgcccaaagatgctaggacg | 47 |
| P15 B | tcattgagcagtggtttgtagttctccttg | 27 | ttatgaacacaccttcccaccaagagg | 48 |
| P15 C | ttagtctaaattagggatacacactcctcc | 28 | caatatcgtgaaaatggccatactg | 49 |

TABLE 1-continued

Primer sets for the isolation of genomic elements (5' -> 3' direction)

| | forward primer | SEQ ID NO | reverse primer | SEQ ID NO |
|---|---|---|---|---|
| P15 D | atggaagatagtggaaccaacttggaaagc | 29 | tcaggggtacatgtgcaggtttgttacata | 50 |
| P15 E | agctttagctactccagctttctgggtgt | 30 | tggaaaggtagtcttcaagcttggaaattc | 51 |
| P15 F | tttcactacttcccctgtataacctccacg | 31 | aagatctgtgagagcagtgtggattccc | 52 |
| P73 Z | gcaccacgtttgagcacctctggag | 32 | cagttttccagggggcactcagagc | 53 |
| P73 A | tgtgatttggaataaaacctccctgaagagg | 33 | gcgggcgttagcgcctttttag | 54 |
| P73 B | ccagacagctatgagcactcagtggact | 34 | cagggaggttttattccaaatcaca | 55 |
| P73 C | aaatacatttaaaaatctggcagagccggg | 35 | tgatggagttggatcccagtgtttgg | 56 |
| P73 D | atcaacgccaccgttcttccatgtc | 36 | cagtgccacctttctcttggttaggatttt | 57 |
| P73 E | tactatcttgggatcattaatggctgcagg | 37 | caggcatccagttctgagctttctctct | 58 |
| P73 F | cgcgaacagcctcagcttctgaatg | 38 | ggtgggaaactgctccttcactttgct | 59 |

1.1 Results

We transfected the plasmids with the isolated DNA stretches from the Rb1, p15 and p73 loci to CHO-DG44 cells. The same amount of DNA (3 μg) of all constructs was transfected to CHO-DG44 cells with Lipofectamine 2000 (Invitrogen). Selection was performed with 400 μg/ml Zeocin in the culture medium, which was added 24 hours after transfection. The culture medium consisted of HAMF12: DMEM=1:1+4.6% fetal bovine serum. After approximately two weeks the number of stably established colonies were counted. As shown in FIG. 2A, transfection of the construct encompassing START/67/7 resulted in 105 stable colonies. Transfection of seven constructs containing DNA sequences from the p73 gave rise to hardly any colonies (FIG. 2A). In contrast, transfection of the constructs containing the DNA sequences from either the Rb1 or p15 loci gave a significant number of colonies. Specifically, the Rb1E, p15C and Rb1F sequences induced 247, 125 and 113 colonies respectively (FIG. 2). Since the Rb1E and p15C sequences induced ~2.5 and ~1.25 more colonies than STAR 7/67/7 elements respectively, we decided to focus on these sequences. Analysis of the sequences in databases such as blast revealed no known sequence motifs, promoter regions or repeats. No duplications of the sequences in the human genome were found either.

These experiments were performed with the TTG Zeo selection system that has been devised in the context of STAR elements. Recently, we developed a novel selection principle in which short peptides are placed upstream of a selectable marker, such as the Zeocin resistance marker. In essence, when this small peptide becomes longer, the translation machinery will have increasing difficulties to re-initiate at the translation initiation codon of the Zeocin mRNA. As a result higher levels of mRNA have to be produced in order to warrant enough translated, functional Zeocin resistance protein. This creates a stringent selection marker system, called ppZeo selection system. Here we tested whether the Rb1A to F elements as well as the p15C element are also able to induce more colonies with high d2EGFP expression levels when put in the context of the ppZeo selection system.

As selectable marker we used the $pp^8Zeo^{EPP5}$ variant (SEQ ID NO: 16). This variant harbors a small peptide of 8 amino acids and is placed upstream of a Zeocin selectable marker mutant that is more stringent than the wild type Zeocin marker. This mutant is created by Error Prone PCR (EPP). The $pp^8Zeo^{EPP5}$ variant provides slightly higher selection stringency than the TTG Zeo selectable marker.

Figure 2B:
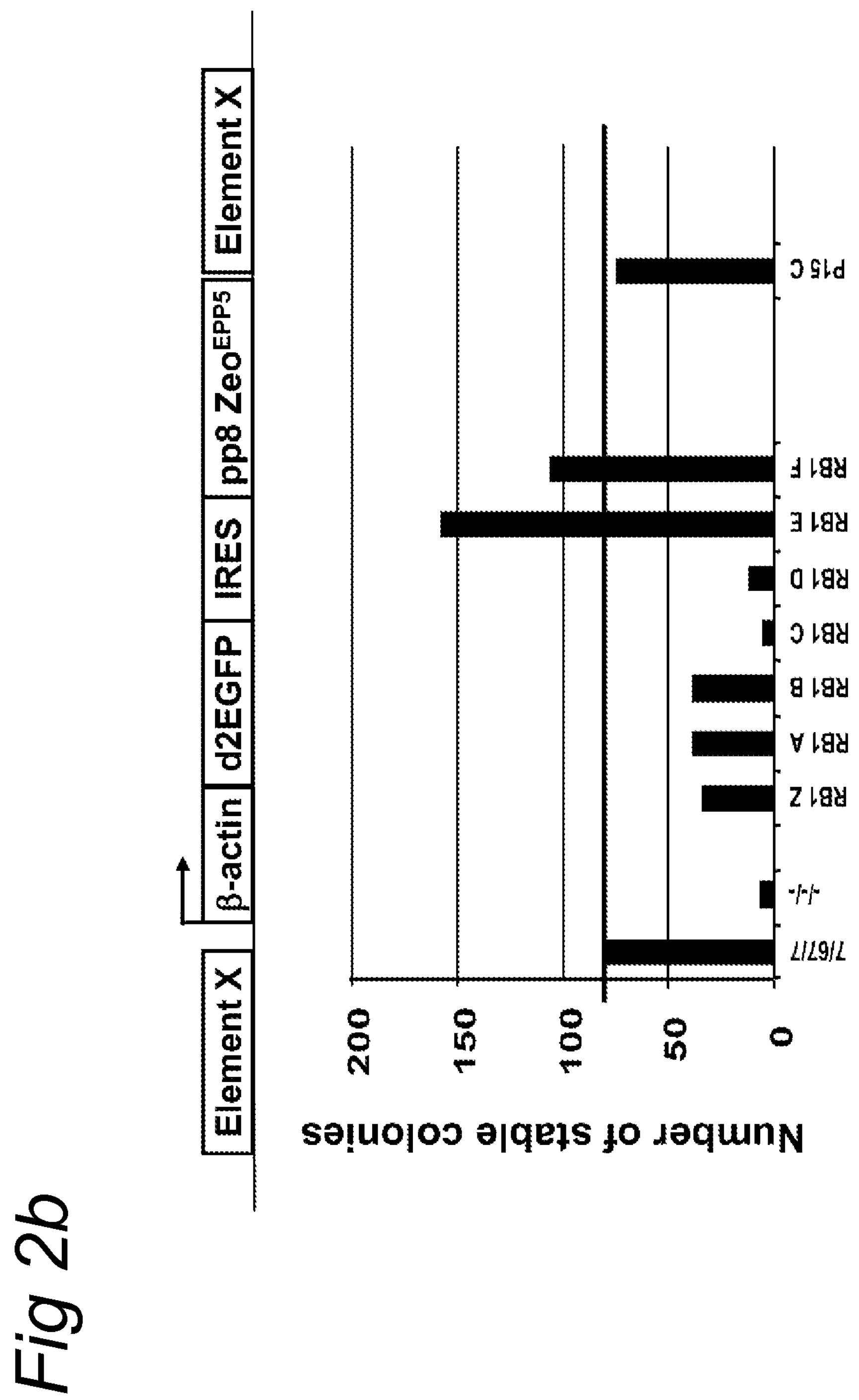

We flanked the expression cassette (SEQ ID NO: 9) with the Rb1A-F and p15C sequences, as well with STARs 7/67/7 (SEQ ID NO: 10)(FIG. 2B). As shown in FIG. 2B, the STAR 7/67/7 combination induced 76 colonies, slightly less than with the TTG Zeo marker (FIG. 2A). This is in agreement with the notion that the $pp8Zeo^{EPP5}$ marker is slightly more stringent than the TTG Zeo marker. Importantly, hardly any colony emerged when no elements at all were included in the construct. As with the TTG Zeo marker, the constructs containing the Rb1E, Rb1F and the p15C induced the most colonies in the context of the $pp8Zeo^{EPP5}$ marker. Rb1E induced 163 colonies, Rb1F 124 colonies and P15C 69 colonies (FIG. 2B).

We conclude that some of the genomic DNA loci that we screened contain sequences that are able to induce an equal number or more colonies than STAR elements in the context of the two different, high stringency selection system.

2. Example 2: The Rb1E, Rb1F and p15C Sequences Induce Equal or Higher Protein Expression Levels than STAR Elements in the Context of a Stringent Selection System Since the constructs that contain the Rb1E and p15C sequences also harbor the d2EGFP reporter gene, we were able to analyze the influence of the Rb1E and p15C DNA sequences on the d2EGFP expression levels.

2.1 Results

Between 12 and 24 independent colonies induced by the indicated constructs were isolated. Colonies were propagated before analysis by flow cytometric analysis (EPICS-XLM, Beckman-Coulter), 3 to 4 weeks after transfection. The fluorescence signal derived from d2EGFP (destabilized) is linear with the amount of available d2EGFP protein in a cell, and is thus a reliable indicator of the d2EGFP expression levels in the cell. In a single FACS analysis, fluorescence signals from a sample that contain up to 4000 cells are analyzed. One such sample of cells is taken from an independent, stably transfected cell colony. Since the signal will vary amongst the individual cells in the colony, the mean fluorescence level of the ~4000 cells in the sample is taken as a measure for the d2EGFP expression level in the stably transfected cell colony.

As shown in FIG. 3, incorporation of the Rb1E, Rb1F and p15C sequences induced equal or slightly higher d2EGFP expression levels, as compared to the control construct with the STAR 7/67/7 elements. This was the case in the context of both the TTG Zeo and pp 8Zeo$^{EPP5}$ markers. Overall, the d2EGFP expression values were highest with the Rb1E sequences, again, with both selection markers.

We conclude that the inclusion of the Rb1E, Rb1F or p15C sequences not only induces more colonies, but these colonies also display a higher d2EGFP expression level. This is tested in the context of a stringent selection system that is routinely used with STAR elements.

3. Example 3: The Rb1E and p15C Sequences do not Harbor Promoter or Enhancer Activity, are No STAR Elements, but are Sources of Intergenic Transcription Possible reasons for the ability of the Rb1E and p15C elements to induce a high number of colonies with high protein expression levels could be that these elements are promoters themselves. Alternatively, the elements could be STAR elements. We tested these possibilities experimentally.

3.1 Results

The construct that contained STARs 7/67/7 and the β-actin promoter was modified in such a way that the β-actin promoter was replaced by either the Rb1E or p15C element. This created constructs that contained the Rb1E and p15C elements placed immediately upstream of the TTG Zeo d2EGFP cassette. We compared these constructs with the constructs described in Example 2, that did harbor the β-actin promoter (FIG. 4). We transfected the constructs to CHO-DG44 cells and measured the transient d2EGFP values. As shown in FIG. 4A, the constructs with either the Rb1E or p15C element, but without β-actin promoter gave no d2EGFP signal at all. This indicates that the elements are no functional promoters. To further substantiate this notion we kept the transfected cells under Zeocin selection pressure. As shown in FIG. 4B, the constructs containing STAR elements, the Rb1E or p15C with the β-actin promoter induced 112, 275 and 154 colonies respectively. In contrast, the constructs with the Rb1E and p15C elements, but without β-actin promoter induced no colonies at all. Next, we tested whether the Rb1E or p15C elements might be enhancer elements. We tested this by placing the elements upstream of the SV40 minimal promoter and the combined TTG Zeo-d2EGFP gene. As control constructs we took the β-actin promoter upstream of the TTG Zeo-d2EGFP gene. We also placed the SV40 minimal promoter upstream of the TTG Zeo-d2EGFP gene. Finally, we placed the SV40 enhancer upstream of the SV40 minimal promoter. This is the natural occurring SV40 enhancer/promoter configuration. As shown in FIG. 5, only the constructs in which the β-actin promoter or the 'complete' SV40 enhancer/promoter combination was placed upstream of the reporter gene gave significant d2EGFP signals (arbitrarily put at 100). Neither construct with the SV40 minimal promoter gave any signal, indicating that the Rb1E nor p15C elements are no enhancers. Taken together these data show that the Rb1E and p15C elements are no functional promoters or enhancers.

We next tested whether stable transfection of the constructs harboring the Rb1E and p15C elements would in trans influence the endogenous CHO Rb1 or p15 expression. We devised a primer set that gave a positive mRNA signal, corresponding with the endogenous CHO Rb1 and p15 genes. The following primer sets were used:

```
                                          (SEQ ID NO: 80)
P15 Forward:        GGAGCAGAACCCAACTGCGC

                                          (SEQ ID NO: 81)
P15 Reverse:        CCAGGCGTCACACACATCCAG

                                          (SEQ ID NO: 82)
RB1 Forward:        GTGACAGAGTGCTCAAAAGAAGTGCTG

                                          (SEQ ID NO: 83)
RB1 Reverse:        GGACTCCGCTGGGAGATGTTTACTC
```

Subsequently, we measured the ratio of the β-actin and the Rb1 mRNA level or the β-actin and the p15 mRNA level, by real time PCR. We compared these ratios in CHO-DG44 versus Rb1E or p15C transfected colonies. We compared four independent clones of each element. In FIG. 6 we show the result for one clone. We found that transfection of a construct containing either the Rb1E or p15C element did not influence the ratio between the β-actin and respective endogenous Rb1 or p15 genes. This was the case in all four independent clones.

We conclude that transfection of the Rb1E or p15C elements do not have a positive or negative effect on the expression of the respective endogenous genes.

We also tested whether the Rb1E or p15C elements harbor STAR activity. This can be directly tested by placing the elements between targeted LexA-HP1 repressors and the Zeocin selection gene. When the elements have no STAR activity, the HP1-mediated gene repression will silence the Zeocin selection marker gene. Subsequent addition of Zeocin to the culture medium will result in cell death. On the other hand, when an element does contain STAR activity, the HP1-mediated gene repression is not strong enough to silence the Zeocin selection marker. Subsequent addition of Zeocin to the culture medium will result in survival of these cells. These experiments were performed in U2-OS cells, as was the original screen to identify and isolate STAR elements (Kwaks et al., 2003, Nature Biotech. 21: 553-558). As shown in FIG. 7, placing STAR 7 between the LexA-HP1 binding sites and the Zeocin marker gene does indeed result in cell survival and resulting, fast growing colonies. As shown in FIG. 7, neither the testing of the full-length Rb1E, Rb1F and p15C elements or shorter fragments resulted in the emergence of colonies. The smaller fragments corresponded with the fragments that were also tested for their ability to induce a high number of colonies with high protein expression levels (see example 5; FIGS. 14 and 15). We also tested the Rb1E/Rb1F combination (2425-3224 (Rb1F)-1-2018 (Rb1E)) for STAR activity and found no such activity (FIG. 7). We conclude from these results that neither Rb1E, Rb1F nor P15C contain STAR activity.

Finally, we tested the possibility that the Rb1E or p15C elements as sources of intergenic transcription. Rb1E and p15C harbor a striking ability to induce many colonies with high protein expression levels in the context of a stringent selection system. As shown above, they do not contain promoter, enhancer of STAR activity. We therefore tested whether they are regions in which intergenic transcription takes place.

To determine whether intergenic transcripts are associated with the Rb1E and p15C elements, we designed five primer sets for the Rb1E and p15C genomic elements.

TABLE 2

Primer sets for the performance of real time PCR and detection intergenic transcription (5' → 3' direction).

| primer | Sequence | SEQ ID NO |
|---|---|---|
| P15C 50 F | GATACACACTCCTCCCTGAGCTCTAGAC | 60 |
| P15C 232 R | AATGAGAGAGGTTGGGATCATGGTC | 61 |
| P15C 537 F | GTCCTAACATGGCCTATACAGCTCTACAAC | 62 |
| P15C 691 R | CAGAAGAAACTGCATGTGGCAAGC | 63 |
| P15C 1468 F | TCAACCTCTGCCTCCTGGGTTC | 64 |
| P15C 1613 R | TTCAAGACCAGCCTGACCAACATG | 65 |
| P15C 2317 F | TTGTGTGAAACGGGTAGGTTGAGC | 66 |
| P15C 2497 R | GCCAATATGGTGAAACCCCATCTC | 67 |
| P15C 3133 F | CTCTGTTTTGGTACCAGTACCATGCTG | 68 |
| P15C 3274 R | ATATGGAACCAAAAAGGAGCCCG | 69 |
| RB1 E 134-F | AAGCTTCCTGACTTCAGCCTAAAGATTC | 70 |
| RB1 E 292-R | CTTACCTGACATTTCTGTCATCTTCCTCTTC | 71 |
| RB1 E 941-F | CTCATACGCATATCATGTGGACAAAGTG | 72 |
| RB1 E 1112-R | GGCAACAGAGCGAGACTCAGTCTC | 73 |
| RB1 E 1714-F | ATCCCACTGAATTACTGAGAGGATTGATC | 74 |
| RB1 E 1886-R | CCATGTCCTTGTGTTGAGCTCTCTG | 75 |
| RB1 E 2561-F | ATAGCTAAACTGTCTTCTCAGGAGAGGAGC | 76 |
| RB1 E 2677-R | CTCTGCTTGGCATCTACCTCCAAAC | 77 |
| RB1 E 3374-F | GAACTTGCACTTGTCCCACATCCAG | 78 |
| RB1 E 3508-R | CAGGAACAGAATCAGTGCTTTTTCCTC | 79 |

F = forward primer; R = reverse primer

Using random hexamers we made cDNA from total RNA, isolated from U2-OS cells. We selected this human cell line to assess whether there were endogenous intergenic transcripts associated with the indicated genomic loci. With real time PCR we determined whether there was an elevated level of RNA, transcribed across the tested region. The real time PCR reactions were performed on the cDNA, created from U2-OS cells. As control, the total RNA from which the cDNA was made, was used as sample for the real time PCR reaction. Contamination with genomic DNA in the RNA sample would also give a background signal. The difference in the respective signal levels in the RNA or cDNA samples was taken as measure for the level of intergenic transcripts. As shown in FIGS. 8 and 9, we found with three out of five primer sets positive Rb1E signals and with four out of five primer sets p15C signals when using cDNA and RNA isolated from U2-OS cells (first columns in respectively FIGS. 8 and 9). The indicated factor is the difference in signal level in the cDNA sample versus the RNA sample. These data indicate that intergenic transcripts are associated with the Rb1E and p15C loci.

We next tested whether such positive signals could also be detected in CHO-DG44 colonies that were induced by constructs containing either the human Rb1E or p15C elements. As source for the RNA/cDNA we took the same four colonies in which we tested whether the elements had an in trans influence on the expression of the endogenous CHO Rb1 or p15 promoters (FIG. 5). As negative controls we included RNA or cDNA from four clones that were transfected with another construct. Hence RNA/cDNA from cells transfected with the p15C element served as negative control in the test for intergenic Rb1E transcripts (FIG. 8) and vice versa (FIG. 9). As shown in FIG. 8, there was substantial intergenic transcription at the same three of the five different locations within the Rb1E element as in U2-OS cells (second columns in FIG. 8). Importantly, no such positive signal was detected when p15C-transfected clones were taken as source for the RNA/cDNA samples (third columns in FIG. 8). It should be noted the absolute amount of detected transcripts was higher in the Rb1E transfected cells than in U2-OS cells, probably due to the fact that multiple copies harboring the Rb1E element are transfected, while the U2-OS cells have only two endogenous copies. However, the ratios between the cDNA and RNA signals were the same and these are indicated in FIGS. 8 and 9.

As shown in FIG. 9, there was also substantial intergenic transcription at the same four of the five different locations within the p15C element as in U2-OS cells (second columns in FIG. 9). Importantly, no such positive signal was detected when Rb1E-transfected clones were taken as source for the RNA/cDNA samples (third columns in FIG. 9).

As overall conclusion for this example we take it that the ability of Rb1E and p15C elements to induce a high number of colonies with high protein expression levels is not due to endogenous promoter, enhancer activity or STAR activity. Instead they appear to contain regions that are associated with intergenic transcriptions. A possibility is that due to this intergenic transcription the locus signifies an open chromatin structure that is pivotal enabling high transcription levels from the downstream promoter.

4. Example 4: Rb1E Induced High Colony Number and d2EGFP Values are not Due to an Increased Number of Plasmid Copies The Rb1E element induces more colonies than STAR elements and with at least equally high d2EGFP values. One possibility might be that inclusion of the Rb1E element might result in stable colonies that have more copies of the plasmid incorporated. We tested this by directly determining the copy numbers of the respective plasmid in a seven independently isolated stable colonies.

4.1 Results

We isolated DNA from seven clones that were transfected with either STAR 7/67/7 or Rb1E elements. The average d2EGFP values in the seven STAR-induced colonies was 156, and in the seven Rb1E-induced colonies 299. As shown in FIG. 10, the average copy number in STAR-induced colonies was 79, whereas the average copy number in Rb1E-induced colonies was 17. It therefore appears that the high d2EGFP values induced by Rb1E are not due to an increased copy number, but that, instead more d2EGFP is produced per copy.

We also placed the Rb1E and p15C sequences around an expression cassette harboring the CMV promoter, the TTG Zeo selectable marker and the d2EGFP reporter gene. The constructs containing the Rb1E or p15C induced 176 and 107 colonies, as compared to the 152 colonies induced by the STAR 7/67/7 combination (FIG. 11). Up to 24 independent colonies were isolated, propagated and d2EGFP was analyzed. As shown in FIG. 4, the Rb1E and p15C sequences induced average d2EGFP expression levels of 957 and 825 respectively, as compared to the average d2EGFP expression of 862 induced by STARs 7/67/7 (FIG. 11).

5. Example 5: Specific Combinations of Rb1E and p15C Sequences and Localization of Highest Activity within the DNA Stretches We tested the effects of employing different combinations of the Rb1E and p15C sequences. Also, we tested different portions of the elements to analyze whether there is a localized activity within these sequences.

5.1 Results

As shown in FIG. 12, we made constructs in which the Rb1E or p15C element was place only upstream or downstream, as well as flanking the entire expression cassette. Furthermore, we made constructs in which the Rb1E element was placed upstream and the p15C element downstream of the expression cassette. Vice versa, we placed the p15C upstream and the Rb1E element downstream of the expression cassette. FIG. 12 shows that when the Rb1E was placed downstream as single element, colony numbers were significantly higher than when the single Rb1E element was placed upstream of the expression cassette. However, most colonies were induced when two Rb1E elements were used to flank the entire expression cassette. In contrast, no such distinction was found with the p15C element (FIG. 12). Finally, when the Rb1E element was placed downstream and the p15C upstream of the expression cassette, more colonies were induced than when the order of the elements was reversed (FIG. 12). This again shows the dominance of the downstream position for the Rb1E element in a construct.

When we analyzed the d2EGFP expression levels in the respective clones, we found no major differences in the average d2EGFP expression levels (FIG. 13). Although the differences were not much, the highest d2EGFP levels were found with the Rb1E elements on both sides and with the p15C-Rb1E combination. We conclude from these data that both in terms of inducing a high number of colonies and of protein expression levels it is beneficial that two elements are used instead of one.

Next we analyzed different portions of the Rb1E and p15C elements. As shown in FIG. 14, the 1-3498 long by of the Rb1E element was compared to the 1-2018 bp and the 1482-3498 bp region of Rb1E. Likewise, the 1-3352 long by of the p15C element was compared to the 1-1500 bp and 822-3352 bp region of p15C. The most obvious result was that the 1450-3500 bp region of Rb1E did not induce a significant number of colonies, as compared to the full-length sequence and the 1-2018 bp region (FIG. 14). In fact, the 1-2018 bp region appears to harbor most of the ability of Rb1E to induce a high number of colonies in CHO-DG44. In contrast, no such striking result was found with the p15C element. Although the 1-1482 region gave less colonies than the 850-3352 bp region, this difference was less outspoken than with the Rb1E element (FIG. 14). When we analyzed the d2EGFP expression levels in the clones described above, we noted that there were no major differences between the full-length elements and the specific portions (FIG. 15). We conclude from these data that the best configuration of the Rb1E and P15C elements is when used as homologous pair to flank the expression cassette. Only the Rb1E element can be delineated into specific parts, particularly in terms of its ability to induce high numbers of colonies.

We further delineated the Rb1E (1-2018 bp) element to define the minimal sequence that gave both the highest number of colonies and the highest d2EGFP values. As shown in FIG. 16, reducing the Rb1E 1-2018 fragment to 1-1482 bp reduced the number of colonies significantly. Furthermore, the 1-1019 bp fragment gave very little colonies and 1-479 hardly any. Also a small reduction of the 1-2018 fragment from the other side (479-2018 bp) had a dramatic impact on the number of induced colonies. It appears that for optimal colony formation the entire 1-2018 bp region is essential; further shortening of this fragment from either side immediately makes the fragment less effective in inducing a large number of colonies. We next considered the Rb1F fragment. As described in Example 1 (FIG. 2), the Rb1F fragment also induced a significant number of stable colonies, although less than the Rb1E fragment. However, initially, these fragments are merely chosen on the basis of their sequential order in the genomic locus of Rb1. Simply, 3424 bp stretches of genomic Rb1 DNA are isolated and tested. It is well possible that some of the activity we define in the Rb1E fragment overlaps with the joining fragment, Rb1F. We therefore tested which parts of the Rb1F encompassed the highest activity and whether this is adjacent to the Rb1E fragment. We divided the Rb1F fragment into two fragments, 1-2425 and 2425-3424 the last being adjacent to the Rb1E fragment. As shown in FIG. 16, the 2425-3424 bp fragment induced the highest number of colonies, almost as many as the entire, 1-3424 bp fragment. We therefore joined the two fragments, Rb1F (2425-3424) with Rb1E (1-2018) and tested the activity of this combination. As shown in FIG. 16, the combination induced the highest number of colonies, even slightly more than the Rb1E (1-3498) fragment. We conclude that this specific combination encompasses the highest activity of the tested Rb1 locus to induce a high number of stable colonies.

When we analyzed the d2EGFP values in the described fragments, we found the following picture (FIG. 17). Of Rb1E, the entire Rb1E (1-3498) and the Rb1E (1-2018) fragments gave the highest d2EGFP values, as shown above. Of Rb1F, the entire Rb1F (1-3424) and Rb1F (2425-3424) fragments gave highest d2EGFP values (FIG. 17). However, highest d2EGFP values were achieved with the combined Rb1F (2425-3424)/Rb1E (1-2018) fragment. As with the induced number of colonies, the combined element is apparently the best combination, also for inducing high protein expression levels.

6. Example 6: The Rb1E and p15C Elements Induce High EPO Protein Expression Levels 6.1 Results As shown in FIG. 18, we placed the Rb1E or p15C elements upstream of the β-actin promoter, driving the human erythropoietin (EPO) reporter gene. As selectable marker we used the pp$^{8}$Zeo$^{EPP5}$ variant (SEQ ID NO: 16). This variant harbors a small peptide of 8 amino acids and is placed upstream of a Zeocin selectable marker mutant that is more stringent than the wild type Zeocin marker. This mutant is created by Error Prone PCR (EPP) and has been described previously (U.S. provisional application 61/187,022). The pp$^{8}$Zeo$^{EPP5}$ variant provides slightly higher selection stringency than the TTG Zeo selectable marker.

We found that both the Rb1E and p15C elements were able to induce large numbers of stable EPO producing colonies (50 and 46 respectively), as compared to the 22 colonies induced by the STAR 7/67/7 combination. When specific EPO production levels were analyzed in the clones, we found that the Rb1E and p15C elements induced similar EPO expression levels as the STAR 7/67/7 combination (FIG. 18A). When also cell growth was taken into account, allowing an assessment of the volumetric EPO production, we found that the Rb1E element gave slightly better values than either the STAR 7/67/7 or the p15C combinations (FIG. 18B). We conclude that the Rb1E and p15C elements are able to induce a higher number of EPO producing colonies with similar EPO expression. This is the same conclusion as with d2EFP as reporter gene.

The invention claimed is:

1. A nucleic acid construct comprising:

(i) a first nucleic acid fragment having:

(a) at least 98% nucleotide sequence identity over its entire length with a fragment consisting of nucleotide residues 1-1019, 1-1482, 1-2018, 1-3498, 479-1482 or 479-2018 of SEQ ID NO: 5;

(b) at least 98% nucleotide sequence identity over its entire length with a fragment consisting of nucleotide residues 1-2425, 1-2448, 1-3424 or 2425-3424 of SEQ ID NO: 6; or (c) at least 98% nucleotide sequence identity over its entire length with a fragment consisting of nucleotide residues 1-3064, 1-2500 or 1-2000 of SEQ ID NO: 7, and (ii) a nucleotide sequence encoding a selectable marker, which provides resistance against lethal or growth-inhibitory effects of a selection agent or wherein the marker complements a growth-inhibitory deficiency in the cell.

2. The nucleic acid construct according to claim 1, wherein the first nucleic acid fragment has:

(a) nucleotide residues 1-1019, 1-1482, 1-2018, 1-3498, 479-1482 or 479-2018 of SEQ ID NO: 5;

(b) nucleotide residues 1-2425, 1-2448, 1-3424 or 2425-3424 of SEQ ID NO: 6; or (c) nucleotide residues 1-3064, 1-2500 or 1-2000 of SEQ ID NO: 7.

3. The nucleic acid construct according to claim 1, wherein the first nucleic acid fragment is covalently linked to an expression cassette comprising a promoter operably linked to a nucleotide sequence encoding a gene product of interest.

4. The nucleic acid construct according to claim 3, further comprising a second nucleic acid fragment having:

(a) at least 98% nucleotide sequence identity over its entire length with a fragment consisting of nucleotide residues 1-1019, 1-1482, 1-2018, 1-3498, 479-1482 or 479-2018 of SEQ ID NO: 5;

(b) at least 98% nucleotide sequence identity over its entire length with a fragment consisting of nucleotide residues 1-2425, 1-2448, 1-3424 or 2425-3424 of SEQ ID NO: 6; or (c) at least 98% nucleotide sequence identity over its entire length with a fragment consisting of nucleotide residues 1-3064, 1-2500 or 1-2000 of SEQ ID NO: 7; and wherein the first nucleic acid fragment is upstream of the expression cassette and the second nucleic acid fragment is downstream of the expression cassette.

5. The nucleic acid construct according to claim 4, wherein the first nucleic acid is different from the second nucleic acid fragment.

6. The nucleic acid construct according to claim 3, wherein the expression cassette further comprises the nucleotide sequence encoding the selectable marker.

7. The nucleic acid construct according to claim 6, wherein the nucleotide sequence encoding the selectable marker is a least one of:

(a) a nucleotide sequence having a mutation in the start codon that decreases the translation initiation efficiency of the selectable marker polypeptide in a eukaryotic host cell;

(b) a nucleotide sequence that is part of a multicistronic transcription unit comprising (i) the nucleotide sequence encoding the selectable marker; and, (ii) a functional open reading frame comprising in a 5' to 3' direction a translation initiation codon, at least one amino acid codon and a translation stop codon; wherein the stop codon of functional open reading frame is present between 0 and 250 nucleotides upstream of the separate translation initiation codon of the nucleotide sequence encoding the selectable marker, and wherein the sequence separating the stop codon of functional open reading frame and the separate translation initiation codon of the nucleotide sequence encoding the selectable marker is devoid of translation initiation codons; and, (c) a nucleotide sequence encoding a selectable marker polypeptide comprising a mutation encoding at least one amino acid change that reduces the activity of the selectable marker polypeptide compared to its wild-type counterpart, wherein the selectable marker is selected from the group consisting of:

(I) mutated zeocin resistance polypeptide wherein the proline on position 9 is mutated to a threonine or phenylalanine;

(II) mutated neomycin resistance polypeptide wherein the aspartic acid on position 182 is mutated to a glutamic acid and/or the aspartic acid on position 261 is mutated to asparagine; and, (III) mutated zeocin resistance polypeptide having the amino acids sequence of SEQ ID NO: 14.

8. The nucleic acid construct according to claim 6, wherein the nucleotide sequence encoding a selectable marker and the nucleotide sequence encoding a gene product of interest are comprised in a single multicistronic transcription unit, wherein the multicistronic transcription unit is operably linked to the promoter and to a transcription termination sequence downstream of the multicistronic transcription unit.

9. The nucleic acid construct according to claim 3, wherein the promoter is a β-actin promoter, a CMV promoter, an SV40 promoter, a ubiquitin C promoter or an EF1-alpha promoter.

10. The nucleic acid construct according to claim 1, wherein the selectable marker provides resistance against lethal or growth-inhibitory effects of a selection agent selected from the group consisting of zeocin, puromycin, blasticidin, hygromycin, neomycin, methotrexate, methionine sulphoximine and kanamycin.

11. An expression vector comprising the nucleic acid construct according to claim 1.

12. A host cell comprising an expression vector according to claim 11.

13. The host cell according to claim 12, wherein the host cell is a plant cell or a mammalian cell.

14. The host cell according to claim 12, wherein the host cell is of a cell line.

15. The host cell according to claim 14, wherein the cell line is selected from the group consisting of a U-2 OS osteosarcoma, CHO, CHO-K1, CHO-DG44, CHO-DG44-S, human embryonic retinoblast, HEK 293, HuNS-1 myeloma, WERI-Rb-1 retinoblastoma, BHK, Vero, non-secreting mouse myeloma Sp2/0-Ag 14, non-secreting mouse myeloma NSO and NCI-H295R adrenal gland carcinoma cell line.

* * * * *